(12) United States Patent
Schaffer et al.

(10) Patent No.: US 9,193,956 B2
(45) Date of Patent: Nov. 24, 2015

(54) ADENO-ASSOCIATED VIRUS VIRIONS WITH VARIANT CAPSID AND METHODS OF USE THEREOF

(75) Inventors: David V. Schaffer, Danville, CA (US); Ryan R. Klimczak, San Francisco, CA (US); James T. Koerber, San Francisco, CA (US); John G. Flannery, Berkeley, CA (US); Deniz Dalkara Mourot, Berkeley, CA (US); Meike Visel, El Cerrito, CA (US); Leah C. T. Byrne, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/113,205

(22) PCT Filed: Apr. 20, 2012

(86) PCT No.: PCT/US2012/034413
§ 371 (c)(1),
(2), (4) Date: Jan. 22, 2014

(87) PCT Pub. No.: WO2012/145601
PCT Pub. Date: Oct. 26, 2012

(65) Prior Publication Data
US 2014/0294771 A1 Oct. 2, 2014

Related U.S. Application Data

(60) Provisional application No. 61/478,355, filed on Apr. 22, 2011.

(51) Int. Cl.
| | |
|---|---|
| A01N 63/00 | (2006.01) |
| A61K 48/00 | (2006.01) |
| C12N 7/00 | (2006.01) |
| C07K 14/005 | (2006.01) |
| C12N 15/86 | (2006.01) |
| C12Q 1/70 | (2006.01) |
| G01N 33/50 | (2006.01) |

(52) U.S. Cl.
CPC .............. *C12N 7/00* (2013.01); *C07K 14/005* (2013.01); *C12N 15/86* (2013.01); *C12Q 1/70* (2013.01); *C12Q 1/701* (2013.01); *G01N 33/5008* (2013.01); *A61K 48/0075* (2013.01); *C07K 2319/33* (2013.01); *C12N 2750/14121* (2013.01); *C12N 2750/14122* (2013.01); *C12N 2750/14145* (2013.01); *C12N 2810/40* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,096,548 A | 8/2000 | Stemmer | |
| 6,491,907 B1 | 12/2002 | Rabinowitz et al. | |
| 6,596,539 B1 | 7/2003 | Stemmer et al. | |
| 6,703,237 B2 | 3/2004 | Samulski et al. | |
| 6,710,036 B2 | 3/2004 | Kurtzman et al. | |
| 6,733,757 B2 | 5/2004 | Patel et al. | |
| 6,943,153 B1 | 9/2005 | Manning, Jr. et al. | |
| 6,962,815 B2 | 11/2005 | Bartlett | |
| 7,172,893 B2 | 2/2007 | Rabinowitz et al. | |
| 7,252,997 B1 | 8/2007 | Hallek et al. | |
| 7,285,381 B1 | 10/2007 | Hallek et al. | |
| 7,314,912 B1 | 1/2008 | Hallek et al. | |
| 7,556,965 B2 | 7/2009 | Hallek et al. | |
| 7,629,322 B2 | 12/2009 | Kleinschmidt et al. | |
| 7,749,492 B2 | 7/2010 | Bartlett et al. | |
| 7,968,340 B2 | 6/2011 | Hallek et al. | |
| 8,524,446 B2 | 9/2013 | Gao et al. | |
| 8,574,583 B2 | 11/2013 | Kay et al. | |
| 8,663,624 B2* | 3/2014 | Schaffer et al. | 424/93.6 |
| 2002/0136710 A1 | 9/2002 | Samulski et al. | |
| 2002/0192823 A1* | 12/2002 | Bartlett | 435/456 |
| 2003/0143732 A1 | 7/2003 | Fosnaugh et al. | |
| 2004/0180440 A1 | 9/2004 | Zolotukhin | |
| 2005/0053922 A1 | 3/2005 | Schaffer et al. | |
| 2005/0220766 A1 | 10/2005 | Amalfitano et al. | |
| 2005/0287122 A1* | 12/2005 | Bartlett et al. | 424/93.2 |
| 2006/0292117 A1 | 12/2006 | Loiler et al. | |
| 2007/0020624 A1 | 1/2007 | Rubenfield et al. | |
| 2007/0196338 A1 | 8/2007 | Samulski et al. | |
| 2008/0269149 A1 | 10/2008 | Bowles et al. | |
| 2009/0202490 A1 | 8/2009 | Schaffer et al. | |
| 2010/0172871 A1 | 7/2010 | Flannery et al. | |
| 2012/0093772 A1 | 4/2012 | Horsager et al. | |
| 2013/0323302 A1 | 12/2013 | Constable et al. | |
| 2014/0242031 A1* | 8/2014 | Schaffer et al. | 424/93.2 |
| 2014/0364338 A1 | 12/2014 | Schaffer et al. | |

FOREIGN PATENT DOCUMENTS

| | | |
|---|---|---|
| CA | 2 379 220 | 1/2001 |
| JP | 2002-518050 | 6/2002 |

(Continued)

OTHER PUBLICATIONS

Grieger et al. J Virol 2006;80:5199-210.*

(Continued)

*Primary Examiner* — Janice Li
(74) *Attorney, Agent, or Firm* — Bozicevic, Field & Francis LLP; Paula A. Borden; David C. Scherer

(57) ABSTRACT

The present disclosure provides adeno-associated virus (AAV) virions with altered capsid protein, where the AAV virions exhibit greater infectivity of retinal cells, when administered via intravitreal injection, compared to wild-type AAV. The present disclosure further provides methods of delivering a gene product to a retinal cell in an individual, and methods of treating ocular disease.

25 Claims, 22 Drawing Sheets

(56) References Cited

FOREIGN PATENT DOCUMENTS

| WO | WO 97/38723 A1 | 10/1997 |
| --- | --- | --- |
| WO | WO 99/67393 A2 | 12/1999 |
| WO | WO 00/28004 A1 | 5/2000 |
| WO | WO 03/023032 A2 | 3/2003 |
| WO | WO 03/054197 A2 | 7/2003 |
| WO | WO 03/093436 A2 | 11/2003 |
| WO | WO 2006/066006 A2 | 6/2006 |
| WO | WO 2008131951 A1 * | 11/2008 |
| WO | 2010/093784 A2 | 8/2010 |

OTHER PUBLICATIONS

Pechan et al. Gene Ther 2009;16:10-16.*
Rabinowitz et al. Virol 2000;278:301-8.*
Michelfelder et al. PLoS ONE 2009;4:e5122,pp. 1-13.*
Buning et al., "Receptor targeting of adeno-associated virus vectors", Gene Therapy, 2003, vol. 10, pp. 1142-1511.
Diprimio et al., "Surface loop dynamics in adeno-associated virus capsid assembly", Journal of Virology, 2008, vol. 82, No. 11, pp. 5178-5189.
Girod et al., "Genetic capsid modifications allow efficient re-targeting of adeno-associated virus type 2." Nat. Med., 1999, vol. 5, No. 9, pp. 1052-1056.
Grifman et al., "Incorporation of tumor-targeting peptides into recombinant adeno-associated virus capsids". Molecular Therapy, 2001, vol. 3, No. 6, pp. 964-975.
Koerber et al., "Molecular evolution of adeno-assoicated virus for enhanced glial gene delivery", Molecular Therapy, 2009, vol. 17, No. 12, pp. 2088-2095.
Li et al., "Generation of novel AAV variants by directed evolution for improved CFTR delivery to human ciliated airway epithelium", Molecular Therapy, 2009, vol. 17, No. 12, pp. 2067-2077.
Mitchell et al., "AAV's anatomy: Roadmap for optimizing vectors for translational success", Curr Gene Ther., 2010, vol. 10, No. 5, pp. 319-340.
Muller et al., "Random peptide libraries displayed on adeno-associated virus to select for targeted gene therapy vectors", Nat Biotechnol, 2003, vol. 21, No. 9, pp. 1040-1046.
Nicklin et al., "Efficient and selective AAV2-mediated gene transfer directed to human vascular endothelial cells", Molecular Therapy, 2001, vol. 4, No. 2, pp. 174-181.
Perabo et al., "Combinatorial engineering of a gene therapy vector: directed evolution of adeno-associated virus", The Journal of Gene Medicine, 2006, vol. 8, pp. 155-162.
Shi et al., "Insertional mutagenesis of the adeno-associated virus type 2 (AAV2) capsid gene and generation of AAV2 vectors targeted to alternative cell-surface receptors", Hum Gene Ther, 2001, vol. 12, No. 14, pp. 1697-1711.
Wu et al., "Mutational analysis of the adeno-associated virus type 2 (AAV2) capsid gene and construction of AAV2 vectors vitti altered tropism" Journal of Virology, 2000 vol. 71, No. 18, pp. 8635-8647.
Wu et al., "α2,3 and α2,6 n-linked sialic acids facilitate efficient binding and transduction by adeno-associated virus types 1 and 6", Journal of Virology, 2006, vol. 80, No. 18, pp. 9093-9103.
Allocca et al, "Novel adeno-associated virus serotypes efficiently transduce murine photoreceptors", Journal of Virology, Oct. 2007, 81(20):11372-11380.
Bichsel et al., "Bacterial delivery of nuclear proteins into pluripotent and differentiated cells", PLoS One, Jan. 2011, 6(1):e16465.
Boucas et al., "Engineering adeno-associated virus serotype 2-based targeting vectors using a new insertion site-position 453-and single point mutations", J Gene Med., Dec. 2009, 11(12):1103-1113.
Jang et al., "An evolved adeno-associated viral variant enhances gene delivery and gene targeting in neural stem cells", Mol Ther., Apr. 2011, 19(4):667-675.
Klimczak et al., "A novel adeno-associated viral variant for efficient and selective intravitreal transduction of rat muller cells", PLoS One, Oct. 2009, 4(10):e7467.
Lai et al., "Long-term evaluation of AAV-mediated sFlt-1 gene therapy for ocular neovascularization in mice and monkeys", Mol Ther., Oct. 2005, 12(4):659-668.
Padron et al., "Structure of adeno-associated virus type 4," Journal of Virology, Apr. 2005, 79(8): 5047-5058.
Petrs-Silva et al., "Novel properties of tyrosine-mutant AAV2 vectors in the mouse retina", Mol Ther., Feb. 2001, 19(2):293-301.
Ryals et al., "Quantifying transduction efficiencies of unmodified and tyrosine capsid mutant AAV vectors in vitro using two ocular cell lines," Mol Vision, Apr. 2011, 17:1090-1102.
Shen et al., "Characterization of the relationship of AAV capsid domain swapping to liver transduction efficiency", Mol Ther., 2007, 15(11):1955-1962.
Van Vliet et al., "Proteolytic mapping of the adeno-associated virus capsid", Mol Ther., Dec. 2006, 14(6):809-821.
Michelfelder, et al., "Vectors selected from adeno-associated viral display peptide libraries for leukemia cell-targeted cytotoxic gene therapy", Experimental Hematology; vol. 35, pp. 1766-1776 (2007).
Waterkamp, et al.; "Isolation of targeted AAV2 vectors from novel virus display libraries"; J. Gene. Med.; vol. 8, pp. 1307-1319 (Sep. 6, 2006).
U.S. Appl. No. 14/444,347, filed Jul. 28, 2014, Schaffer et al.
U.S. Appl. No. 14/606,543, filed Jan. 27, 2015, Schaffer et al.
Attached Score Report Result Per SEQ ID No. 17 per US2002/0192823 to Bartlett Published Dec. 19, 2002.
Blacklow, et al.; "A Seroepidemiologic Study of Adenovirus-Associated Virus Infection in Infants and Children"; Am J Epidemiol.; vol. 94, No. 4, pp. 359-366 (Oct. 1971).
Buch, et al., "In Contrast to AAC-Mediated Cntf Expression. AAV-Mediated Gdnf Expression Enhances Gene Replacement Therapy in Rodent Models of Retinal Degeneration"; Molecular Therapy; vol. 14, No. 5, pp. 700-709 (Nov. 2006).
Choi, et al.; "AAV Hybrid Serotypes: Improved Vectors for Gene Delivery."; Current Gene Therapy; vol. 5, No. 3, pp. 299-310 (Jun. 2005).
Davidson, et al.; "Recombinant adeno-associated virus type 2, 4, and 5 vectors: transduction of variant types and regions in the mammalian central nervous system."; Proc Natl Acad Sci USA; vol. 97, No. 7, pp. 3428-3432 (Mar. 28, 2000).
Den Dunnen, et al.; "Mutation nomenclature extensions and suggestions to describe complex mutations: a discussion."; Human Mutation; vol. 15, pp. 7-12 (2000).
Erles, et al.; "Update on the prevalence of serum antibodies (IgG and IgM) to adeno-associated virus (AAV)."; J Med Virol.; vol. 59, No. 3, pp. 406-411 (Nov. 1999).
Excoffon, et al.; "Directed evolution of adeno-associated virus to an infectious respiratory virus"; Proc Natl Acad Sci USA; vol. 106, No. 10, pp. 3865-3870 (Mar. 10, 2009).
Flotte, et al.; "Gene expression from adeno-associated virus vectors in airway epithelial cells"; Am J Respir Cell Mol Biol.; vol. 7, No. 3, pp. 7349-356 (Sep. 1992).
GenBank accession No. ABZ10812; AAV13 capsid protein sequence downloaded from NBCI; downloaded on Nov. 3, 2008.
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grieger, et al.; "Seperate basic region motifs within the adeno-associated virus capsid proteins are essential for infectivity and assembly"; Journal of Virology; vol. 80, No. 11, pp. 5199-5210 (2006).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Halbert, et al.; "Repeat transduction in the mouse lung by using adeno-associated virus vectors with different serotypes." J. Virol.; vol. 74, No. 3, pp. 1524-1532 (Feb. 2000).

(56) References Cited

OTHER PUBLICATIONS

Hirsch, et al.; "Directed Evolution of the AAV Capsid for Human Embryonic Stem Cell Transduction"; Molecular Therapy; vol. 17, Supp. 1, S177-S178 (May 2009).
Huttner, et al.; "Genetic modifications of the adeno-associated virus type 2 capsid reduce the affinity and the neutralizing effects of human serum antibodies."; Gene Ther; vol. 10, No. 26, pp. 139-147 (Dec. 2003).
Karp, et al.; "An in vitro model of differentiated human airway epithelia. Methods for establishing primary cultures"; Methods Mol Biol.; vol. 188, pp. 115-137 (2002).
Kern, et al.; "Identification of a heparin-binding motif on adeno-associated virus type 2 capsids"; Journal of Virology; vol. 77, No. 20, pp. 11072-11081 (Oct. 2003).
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Li, et al.; "Engineering and Selection of Shuffled AAV Genomes: A New Strategy for Producing Targeted Biological Nanoparticles"; Molecular Therapy; vol. 15, No. 7, pp. 1252-1260 (Jul. 2008).
Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).
Loiler, et al.; "Targeting recombinant adeno-associated virus vectors to enhance gene transfer to pancreatic islets and liver"; Gene Ther.; vol. 10, pp. 1551-1558 (2003).
Maguire, et al.; "Directed evolution of adeno-associated virus for glioma cell transduction"; J. Neurooncol.; vol. 96, pp. 337-347 (2010).
Maheshri, et al.; "Directed evolution of adeno-associated virus yields enhanced gene delivery vectors"; Nature Biotechnology; vol. 24, No. 2, pp. 198-204 (Feb. 2006).
McGee, et al., "Glial Cell Line Derived Neurotrophic Factor Delays Photoreceptor in a Transgenic Rat Model of Retinitis Pigmentosa"; Molecular Therapy; vol. 4, No. 6, pp. 622-629 (Dec. 2001).
Moskalenko, et al; "Epitope mapping of human anti-adeno-associated virus type 2 neutralizing antibodies: Implications for gene therapy and virus structure,"; J. Virol.; vol. 74, No. 4, pp. 1761-1766 (Feb. 2000).
Nguyen, et al.; "Convection-enhanced delivery of AAV-2 combined with heparin increases TK gene transfer in the rat brain."; Neuroreport; vol. 12, No. 9, pp. 1961-1964 (Jul. 3, 2001).
Opie, et al.; "Identification of Amino Acid Residues in the Capsid Proteins of Adeno-Associated Virus Type 2 that Contribute to Heparan Sulfate Proteoglycan Binding"; Journal of Virology; vol. 77, No. 12, pp. 6995-7006 (Jun. 2003).
Paddison, et al.; "Stable suppression of gene expression by RNAI in mammalian cells"; Proc. Nat'l Acad. Sci. USA; vol. 99, No. 3, pp. 1443-1448 (Feb. 5, 2002).
Perabo, et al.; "Heparan Sulfate Proteoglycan Binding Properties of Adeno-Associated Virus Retargeting Mutants and Consequences for Their In Vitro Tropism"; Journal of Virology; vol. 80, No. 14, pp. 7265-7269 (Jul. 2006).
Rabinowitz, et al.;"Insertional mutagenesis of AAV2 capsid and the production of recombinant virus."; Virology; vol. 265, No. 2, pp. 274-285 (Dec. 20, 1999).
Ried, et al.; "Adeno-associated virus capsids displaying immunoglobulin-binding domains permit anitbody-mediated vector retargeting to specific cell surface receptors"; J. Virol.; vol. 76, No. 9, pp. 4559-4566 (May 2002).
Schaffer, et al.; "Directed evolution of AAV vector mutants for enhanced gene delivery"; Abstracts of Papers American Chemical Society; vol. 227, Part 1, p. U214 (Mar. 2004).
Shi, et al.; "RGD inclusion in VP3 provides adeno-associated virus type 2 (AAV2)-based vectors with a heparan sulfate-independent cell entry mechanism"; Mol. Ther.; vol. No. 4, pp. 515-525 (Apr. 2003).

Shi, et al.; "Capsid modifications overcome low heterogeneous expression of heparan sulfate proteoglycan that limits AAV2-mediated gene transfer and therapeutic efficacy in human ovarian carinoma"; Gynecol. Oneal.; vol. 103, pp. 1054-1062 (2006).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1597-1711 (Sep. 20, 2001).
Sonntag, et al.; "Adeno-associated virus type 2 capids with externalized VP1/VP2 trafficking domains are generated prior to passage through the cytoplasm and are maintained until uncoating occurs in the nucleus"; Journal of Virologuy; vol. 80, No. 22, pp. 11040-11054 (Nov. 2006).
Steinbach, et al.; "Assembly of adeno-associated virus type 2 capsids in vitro" J of Gen Virology; vol. 78, pp. 1453-1462 (1997).
Sun, et al.; "Immune response to adeno-associated virus and its recombinant vectors"; Gene Therapy; vol. 10, pp. 964-976 (2003).
Tal; "Adeno-Associated Virus-Based Vectors in Gene Therapy"; Journal of Biomedical Science; vol. 7, No. 4, pp. 279-291 (Jul. 2000).
Tomar, et al.; "Use of Adeno-Associated Viral Vector for Delivery of Small Interfering RNA"; Oncogene; vol. 22, No. 36, pp. 5712-5715 (Aug. 28, 2003).
White, et al.; "Targeted gene delivery to vascular tissue in vivo by tropism-modified adeno-associated virus vectors"; Circulation; vol. 109, pp. 513-519 (Feb. 3, 2004).
Wickham, et al.; "Increased in vitro and in vivo gene tranfer be adenovirus vectors containing chimeric fiber proteins"; Journal of Virology; vol. 71, No. 11, pp. 8221-8229 (Nov. 1997).
Wobus, et al.; "Monoclonal antibodies against the adeno-associated virus type 2 (AAV-2) capsid: epitope mapping and identification of capsid domains involved in AAV-2-cell interaction and neutralization of AAV-2 infection."; J. Virol.; vol. 74, No. 19, pp. 9281-9293 (Oct. 2000).
Work, et al.; "Vascular bed-targeted in vivo gene delivery using tropism-modified adeno-associated viruses"; Mol. Ther.; vol. 13, No. 4, pp. 683-693 (Apr. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Zabner, et al.; "Adeno-associated virus type 5 (AAV5) but not AAV2 binds to the apical surfaces of airway epithelia and facilitates gene transfer"; J Virol.; vol. 74, No. 8, pp. 3852-3858 (Apr. 2000).
Zhao, et al.; "Molecular evolution by staggered extenstion process (StEP) in vitro recombination"; Nat Biotechnol; vol. 16, No. 3, pp. 258-261 (Mar. 1998).
Zolotukhin, et al.; "Recombinant adeno-associated virus purification using novel methods improves infectious titer and yield"; Gene Therapy; vol. 6, pp. 973-985 (1999).
Surace, et al.; "Delivery of Adeno-Associated Virus Vectors to the Fetal Retina: Impact of Viral Capsid Proteins on Retinal Neuronal Progenitor Transduction"; Journal of Virology; vol. 77, No. 14, pp. 7957-7963 (Jul. 2003).
Asokan et al., "Reengineering a receptor footprint of adeno-associated virus enables selective and systemic gene transfer to muscle", Nat Biotechnol, 2010, 28(1):79-82.
Park et al., "Intravitreal delivery of AAV8 retinoschisin results in cell type-specific gene expression and retinal rescue in the Rs1-KO mouse", Gene Therapy, 2009, 16:916-926.
Petrs-Silva et al., "High-efficiency transduction of the mouse retina by tyrosine-mutant AAV serotype vectors", Molecular Therapy, 2009, 17(3):463-471.

\* cited by examiner

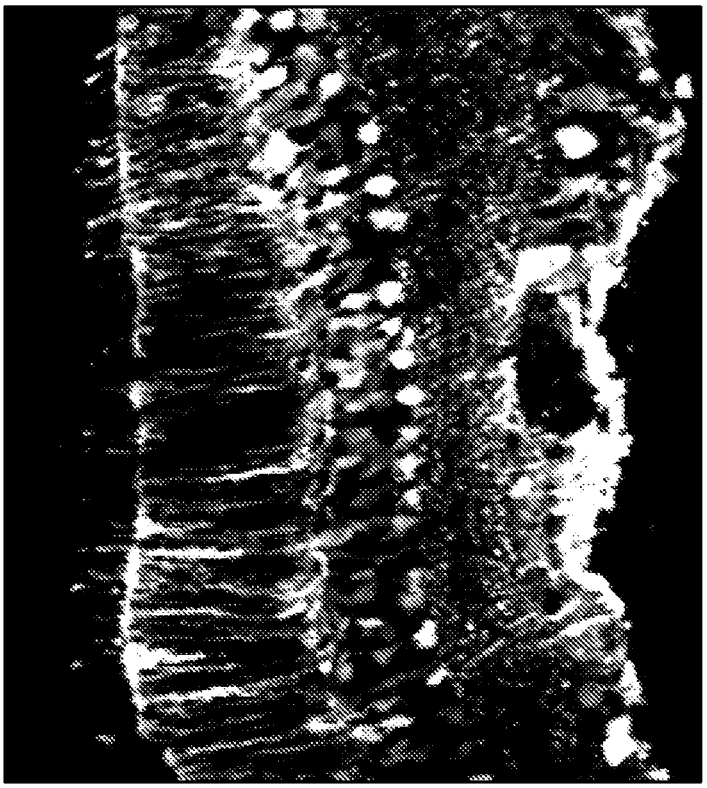
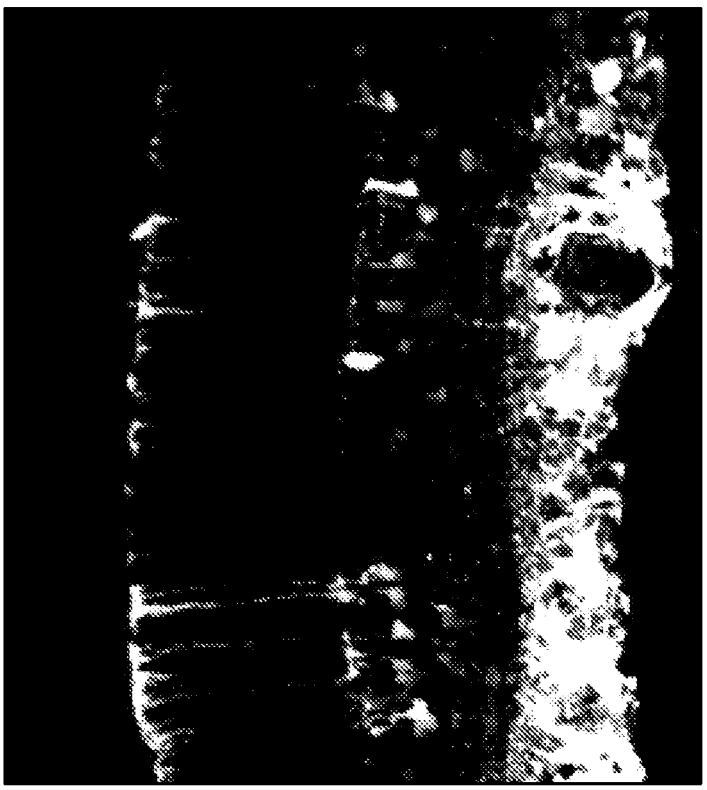
7m8.CAG.GFP
(variant enhanced for PR transduction by directed evolution)
AAV2.CAG.GFP
(parental serotype)
FIG. 2

```
AAV2 VP1    1  MAADGYLPDWLEDTLSEGIRQWWKLKPGPPPPKPAERHKDDSRGLVLPGYKYLGPFNGLD
AAV2 VP1   61  KGEPVNEADAAALEHDKAYDRQLDSGDNPYLKYNHADAEFQERLKEDTSFGGNLGRAVFQ
AAV2 VP1  121  AKKRVLEPLGLVEEPVKTAPGKKRPVEHSPVEPDSSSGTGKAGQQPARKRLNFGQTGDAD
AAV2 VP1  181  SVPDPQPLGQPPAAPSGLGTNTMATGSGAPMADNNEGADGVGNSSGNWHCDSTWMGDRVI
AAV2 VP1  241  TTSTRTWALPTYNNHLYKQISSQSGASNDNHYFGYSTPWGYFDFNRFHCHFSPRDWQRLI
AAV2 VP1  301  NNNWGFRPKRLNFKLFNIQVKEVTQNDGTTTIANNLTSTVQVFTDSEYQLPYVLGSAHQG
AAV2 VP1  361  CLPPFPADVFMVPQYGYLTLNNGSQAVGRSSFYCLEYFPSQMLRTGNNFTFSYTFEDVPF
AAV2 VP1  421  HSSYAHSQSLDRLMNPLIDQYLYYLSRTNTPSGTTTQSRLQFSQAGASDIRDQSRNWLPG
AAV2 VP1  481  PCYRQQRVSKTSADNNNSEYSWTGATKYHLNGRDSLVNPGPAMASHKDDEEKFFPQSGVL
AAV2 VP1  541  IFGKQGSEKTNVDIEKVMITDEEEIRTTNPVATEQYGSVSTNLQRGNRQAATADVNTQGV
AAV2 VP1  601  LPGMVWQDRDVYLQGPIWAKIPHTDGHFHPSPLMGGFGLKHPPPQILIKNTPVPANPSTT
AAV2 VP1  661  FSAAKFASFITQYSTGQVSVEIEWELQKENSKRWNPEIQYTSNYNKSVNVDFTVDTNGVY
AAV2 VP1  721  SEPRPIGTRYLTR    (SEQ ID NO:1)
```

FIG. 5

| | | | |
|---|---|---|---|
| AAV-2 | 570 | PVATEQYGSVSTNLQRGNNRQAATADVNTQGVLPGMVWQDRDV 611 | (SEQ ID NO:2) |
| AAV-1 | 571 | PVATERFGTVAVNFQSSSTDPATGDVHAMGALPGMVWQDRDV 612 | (SEQ ID NO:3) |
| AAV-5 | 560 | RVAYNVGGQMATNNQSSTTAPATGTYNLQEIVPGSVWMERDV 601 | (SEQ ID NO:4) |
| AAV-6 | 571 | PVATERFGTVAVNLQSSSTDPATGDVHVMGALPGMVWQDRDV 612 | (SEQ ID NO:5) |
| AAV-7 | 572 | PVATEEYGIVSSNLQAANTAAQTQVVNNQGALPGMVWQNRDV 613 | (SEQ ID NO:6) |
| AAV-8 | 573 | PVATEEYGIVADNLQQQNTAPQIGTVNSQGALPGMVWQNRDV 614 | (SEQ ID NO:7) |
| AAV-9 | 571 | PVATESYGQVATNHQSAQAQAQTGWVQNQGILPGMVWQDRDV 612 | (SEQ ID NO:8) |
| AAV-10 | 573 | PVATEQYGVVADNLQQQANTGPIVGNVNSQGALPGMVWQNRDV 614 | (SEQ ID NO:9) |

FIG. 6

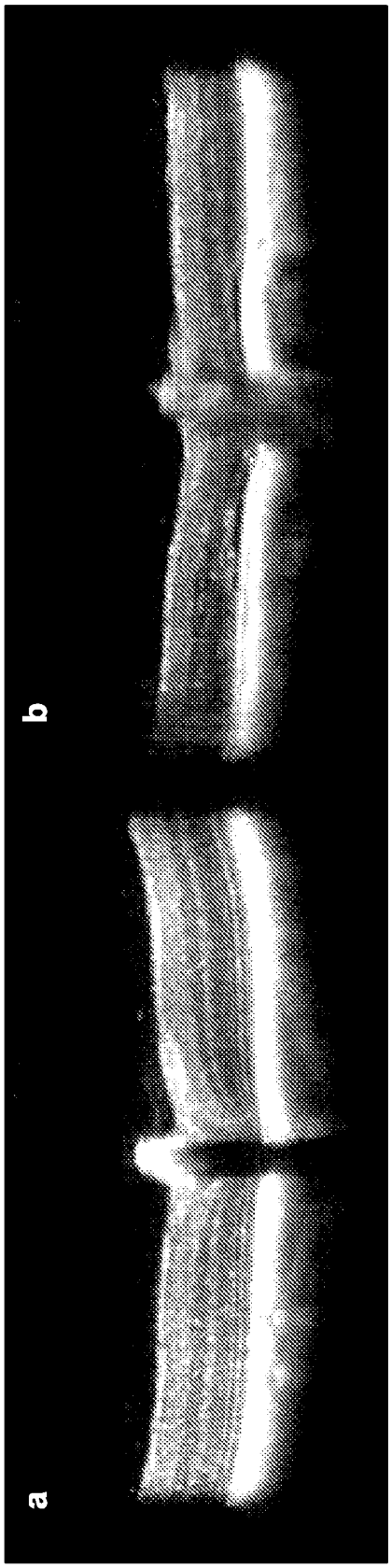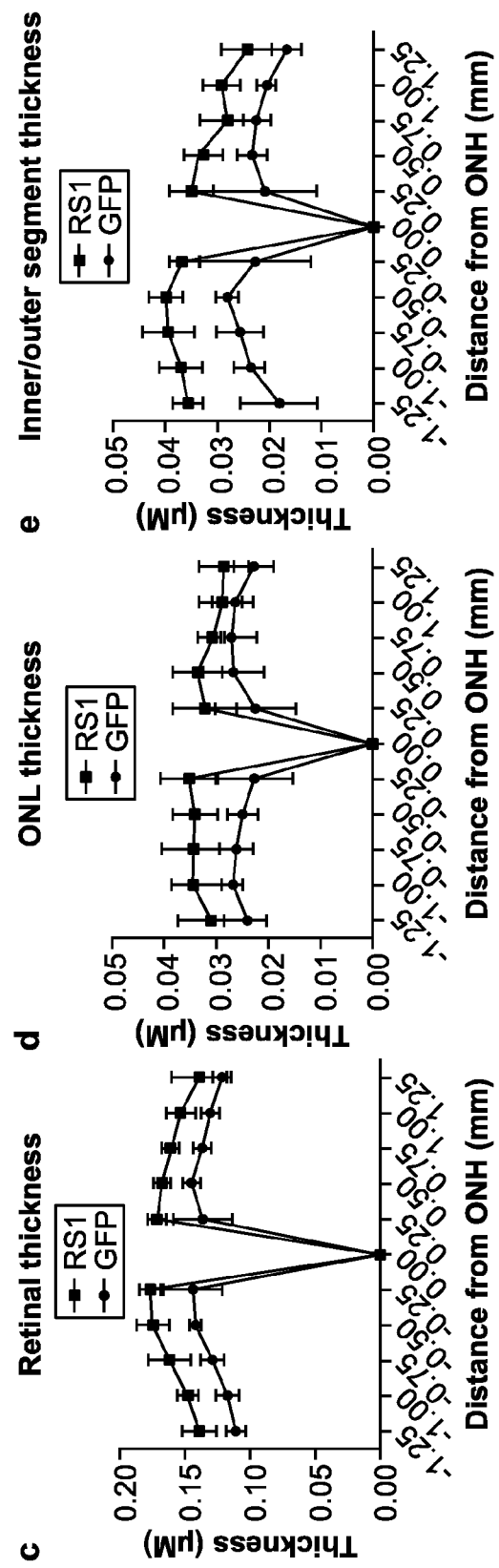
FIG. 9

Retinoschisin-1
*Homo sapiens*
GenBank CAI42483

```
  1 msrkiegfll lllfgyeatl glsstedege dpwyqkackc dcqggpnalw sagatsldci
 61 pecpyhkplg fesgevtpdq itcsnpeqyv gwysswtank arlnsqgfgc awlskfqdss
121 qwlqidlkei kvisgiltqg rcdidewmtk ysvqyrtder lnwiyykdqt gnnrvfygns
181 drtstvqnll rppiisrfir liplgwhvri airmellecv skca (SEQ ID NO:10)
```

FIG. 10

Brain-derived neurotrophic factor
*Homo sapiens*
GenBank CAA62632

```
  1 mtilfltmvi syfgcmkaap mkeanirgqg glaypgvrth gtlesvngpk agsrgltsla
 61 dtfehvieel ldedhkvrpn eennkdadly tsrvmlssqv plepplfll eeyknyldaa
121 nmsmmvlrhs dparrgelsv cdsisewvta adkktavdms ggtvtvlekv pvskgqlkqy
181 fyetkcnpmg ytkegcrgid krhwnsqcrt tqsyvraltm dskkrigwrf iridtscvct
241 ltikrgr (SEQ ID NO:11)
```

FIG. 11

RPE65
*Homo sapiens*
GenBank AAC39660

```
  1 msiqvehpag gykklfetve elsspltahv tgriplwltg sllrcgpglf evgsepfyhl
 61 fdgqallhkf dfkeghvtyh rrfirtdayv ramtekrivi tefgtcafpd pcknifsrff
121 syfrgvevtd nalvnvypvg edyyactetn fitkinpetl etikqvdlcn yvsvngatah
181 phiendgtvy nigncfgknf siaynivkip plqadkedpi skseivvqfp csdrfkpsyv
241 hsfgltpnyi vfvetpvkin lfkflssswsl wganymdcfe snetmgvwlh iadkkrkkyl
301 nnkyrtspfn lfhhintyed ngflivdlcc wkgfefvyny lylanlrenw eevkknarka
361 pqpevrryvl plnidkadtg knlvtlpntt atailcsdet iwlepevlfs gprqafefpq
421 inyqkycgkp ytyayglgln hfvpdrlckl nvktketwvw qepdsypsep ifvshpdale
481 eddgvvlsvv vspgagqkpa yllilnakdl sevaraevei nipvtfhglf kks (SEQ ID NO:12)
```

FIG. 12

```
   1 agcttggatc caatcaacct ctggattaca aaatttgtga aagattgact ggtattctta
  61 actatgttgc tccttttacg ctatgtggat acgctgcttt aatgcctttg tatcatgcta
 121 ttgcttcccg tatgctttc  attttctcct cctgtataa  atcctggttg ctgtctcttt
 181 atgagaagtt gtggcccgtt gtcaggcaac gtggcgtggt gtgcactgtg tttgctgacg
 241 caaccccac  tggttggggc attgccacca cctgtcagct cctttccgg  actttcgctt
 301 tccccctccc tattgccacg gcgaaactca tcgccgcctg cctgcccgc  tgctggacag
 361 gggctcggct gttgggcact gacaattccg tgttgttgtc ggggaagctg acgtccttc
 421 catggctgct cgcctgtgtt gccacctgga ttctgcgcgg gacgtccttc tgctacgtcc
 481 cttccgccct caatccagcg gaccttcctt cccgcggcct gctgccggct ctgcggcctc
 541 ttccgcgtct tcgagatctg cctcgactgt gcctctagt  tgccagccat ctgttgtttg
 601 cccctccccc gtgccttcct tgaccctgga agtgccact  cccactgtcc tttcctaata
 661 aaatgaggaa attgcatcgc attgtctgag taggtgtcat tctattctgg ggggtgggt
 721 gggcaggac  agcaaggggg aggattggga agacaatagc aggcatgctg gggactgag
 781 ttaagggcga attcccgatt aggatcttcc tagagcatgg ctacgtagat aagtagcatg
 841 gcggtttaat cattaactac aaggaacccc tagtgatgga gttgccact  ccctcctcgc
 901 gcgctcgctc gctcactgag gccggcgcgc gccgggcgac caaaggtcgc ccgacgcccg
 961 ggcggcctc  agtgagcgag cgagcgcgca gccttaatta acctaattca ctgcccgtcg
1021 ttttacaacg tcgtgactgg gaaaaccctg gcgttaccca acttaatcgc cttgcagcac
1081 atccccctt  cgccagctgg cgtaatagcg aagaggcccg caccgatcgc ccttcccaac
1141 agttgcgcag cctgaatggc gaatgggacg cgccctgtag cggcgcatta gcgcggcgg
1201 gtgtggtggt tacgcgcagc gtgaccgcta cacttgccag cgccctagcg cccgctcctt
1261 tcgctttctt cccttcctt  ctcgccacgt tcgccggctt tccccgtcaa gctctaaatc
1321 ggggctccc  tttaggttc  cgatttagtg ctttacggca cctcgaccc  aaaaacttg
1381 attagggtga tggttcacgt agtggccat  cgccccgata cggttttt   cgccctttga
1441 cgctgagtt  cacgttcctc aatagtggac tcttgttcca aactgaaca  acactcaacc
1501 ctatctcggt ctattcttt  gatttataag ggattttcc  gatttcggcc tattgttaa
1561 aaatgagct  gatttaacaa aaatttaacg cgaattttaa caaatttta  acgtttataa
1621 tttcaggtgg catctttcgg ggaaatgtgc gcggaaccc  tatttgttta tttttctaaa
1681 tacattcaaa tatgtatccg ctcatgagac aataaccctg ataaatgctt caataatatt
1741 gaaaaaggaa gagtatgagt attcaacatt tccgtgtcgc ccttattccc ttttttgcgg
1801 cattttgcct tcctgttttt gctcacccag aaacgctggt gaaagtaaaa gatgctgaag
```

FIG. 13A

```
1861  atcagttggg  tgcacgagtg  ggttacatcg  aactggatct  caatagtggt  aagatccttg
1921  agagttttcg  cccgaagaa   cgttttccaa  tgatgagcac  ttttaaagtt  ctgctatgtg
1981  gcgcggtatt  atcccgtatt  gacgccgggc  aagagcaact  cggtcgcgc   atacactatt
2041  ctcagaatga  cttggttgag  tactcaccag  tcacagaaaa  gcatcttacg  gatgcatga
2101  cagtaagaga  attatgcagt  gctgccataa  ccatgagtga  taacactgcg  gccaacttac
2161  ttctgacaac  gatcggagga  ccgaaggagc  taaccgcttt  tttgcacaac  atggggatc
2221  atgtaactcg  ccttgatcgt  tgggaaccgg  agctgaatga  agccatacca  aacgacgagc
2281  gtgacaccac  gatgcctgta  gtaatggtaa  caacgttgcg  caaacttgcg  actggcgaac
2341  tacttactct  agcttcccgg  caacaattaa  tagactggat  ggaggcggat  aaagttgcag
2401  gaccacttct  gcgctccgc   cttccggctg  gctggttat   tgctgataaa  tctggagccg
2461  gtgagcgtgg  gtctcgcggt  atcattgcag  cactgggcc   agatggtaag  ccctcccgta
2521  tcgtagttat  ctacacgacg  gggagtcagg  caactatgga  tgaacgaaat  agacagatcg
2581  ctgagatagg  tgcctcactg  attaagcatt  ggtaactgtc  agaccaagtt  tactcatata
2641  tactttagat  tgatttaaaa  cttcatttt   aattaaaag   gatctaggtg  aagatccttt
2701  ttgataatct  catgaccaaa  atccccttaac gtgagtttc   gttccactga  gcgtcagacc
2761  ccgtagaaaa  gatcaaagga  tcttcttgag  atccttttt   tctgcgcgta  atctgctgct
2821  tgcaaacaaa  aaaaccaccg  ctaccagcgg  tggtttgttt  gccgatcaa   gagctaccaa
2881  ctctttttcc  gaaggtaact  ggcttcagca  gagcgcagat  accaaatact  gtccttctag
2941  tgtagccgta  gttaggccac  cacttcaaga  actctgtagc  accgcctaca  tacctcgctc
3001  tgctaatcct  gttaccagtg  gctgctgcca  gtggcgataa  gtcgtgtctt  accgggttgg
3061  actcaagacg  atagttaccg  gataaggcgc  agcggtcggg  ctgaacgggg  ggttcgtgca
3121  cacagcccag  cttggagcga  acgacctaca  ccgaactgag  atacctacag  cgtgagctat
3181  gagaaagcgc  cacgcttccc  gaagggagaa  agcggacag   aggcggacag  agcggcaggg
3241  tcggaacagg  agagcgcacg  agggagcttc  caggggaaa   cgcttatacg  ctttatagtc
3301  ctgtcgggtt  tcgccacctc  tgacttgagc  gtcgatttt   gtgatgctcg  tcaggggggc
3361  ggagctatg   gaaaaacgcc  agcaacgcgg  cctttttacg  gttcctggcc  ttttgctgcg
3421  gtttgctca   catgttcttt  cctgcgttat  ccctgattc   gtgataaac   cgtattaccg
3481  cctttgagtg  agctgatacc  gctcgccgca  gccgaacgac  cgagcgcagc  gagtcagtga
3541  gcgaggaagc  ggaagagcgc  ccaatacgca  aaccgcctct  ccccgcgcgt  tggccgattc
3601  attaatgcag  ctggcacgac  aggtttcccg  actgaaagc   actgaaaagc  cgcaacgcaa
3661  ttaatgtgag  ttagctcact  cattaggcac  cccaggcttt  acactttatg  cttccggctc
```

```
3721  gtatgttgtg tggaattgtg agcggataac aatttcacac aggaaacagc tatgaccatg
3781  attacgccag atttaattaa ggctgcgcgc tcgctcgctc actgaggccg cccggcaaa
3841  gcccgggcgt cgggcgacct ttgtcgccc ggcctcagtg agcgagcgag cgcgcagaga
3901  gggagtggcc aactccatca ctaggggttc cttgtagtta atgattaacc cgccatgcta
3961  cttatctacg tagccatgct ctaggaagat cggaattcgc ccttaagcta gcagatcttc
4021  ccaccctagc cacctgcaa actgctcctt ctctcaaagg cccaaacatg gcctccaga
4081  ctgcaacccc caggcagtca ggccctgtct ccacaacctc acagccaccc tggacggaat
4141  ctgcttcttc ccacattga gtcctcctca gccccctgagc tcctctgggc agggctgttt
4201  ctttccatct ttgtattccc agggggcctgc aataaatgt ttaatgaacg aacaagagag
4261  tgaattccaa ttccatgcaa caaggattgg gctcctgggc cctaggctat gtgtctggca
4321  ccagaaacgg aagctgcagg ttgcagcccc tgccctcatg gagctcctcc tgtcagagga
4381  gtgtggggac tggatgactc cagaggtaac ttgtggggga acgaacaggt aagggctgt
4441  gtgacagagat gagagactgg gagaataaaac cagaaagtct ctagctgtcc agaggacata
4501  gcacagaggc ccatggtccc tatttcaaac ccaggccacc agactgagct gggaccttgg
4561  gacagacaag tcatgcagaa gttaggggac cttctcctcc cttttcctg atggatcctg
4621  agtaccttct cctccctgac ctcaggcttc ctcagtgt caccttggcc cctcttagaa
4681  gccaattagg ccctcagttt ctgcagcggg gattaatatg attatgaaca cccccaatct
4741  ccagatgct gattcagcca ggagcttagg aggggaggt cactttataa gggtctgggg
4801  gggtcagaac ccagagtcat ccctgaatt ctgcagatat ccatcacact gcggccgcg
4861  ccaccatgtc acgcaagata gaaggctttt tgttattact tctctttggc tatgaagcca
4921  cattggatt atcgtctacc gaggatgaag gcgagaccc ctggtaccaa aaagcatgca
4981  agtgcgattg ccaaggagga cccaatgctc tgtggtctgc agtgccacc tccttggact
5041  gtataccaga atgccctcta ccaagcctc tgggtttcga gtgtgtgctg gtcacacgg
5101  accagatcac ctgctctaac ccggagcagt caaggcttg gtattcttcg tggactgcaa
5161  acaaggcccg gctcaacagt gttcgaagg agatcaaagt gctctccaag ttccaggaca
5221  gtagccagtg gttacagata gatctgaagg agatcaaagt gatttcaggg atcctcaccc
5281  agggcgctg tgacatcgat gagtggatga ccaagtacag cgtgcagtac aggaccgatg
5341  agccctgaa ctggatttac tacaaggacc gttcagaacc tgctgcggcc ccccatcatc tcccgcttca
5401  actcgaccg cacctccacg gttcagaacc tgctgcggcc cccatcatc tcccgcttca
5461  tccgcctcat cccgctggc tggcacgtcc gcattgccat ccggatggag ctgctggagt
5521  gcgtcagcaa gtgtgcctga a (SEQ ID NO:18)
```

Peripherin-2

```
  1 mallkvkfdq kkrvklaqgl wlmnwfsvla giiifslglf lkielrkrsd vmnnseshfv
 61 pnsligmgvl scvfnslagk icydaldpak yarwkpwlkp ylaicvlfni ilflvalccf
121 llrgslentl ggglkngmky yrdtdtpgrc fmkktidmlq iefkccgnng frdwfeiqwi
181 snryldfssk evkdriksnv dgrylvdgvp fsccnpsspr pciqyqitnn sahysydhqt
241 eelnlwvrgc raallsyyss lmnsmgvvtl liwlfevtit iglrylqtsl dgvsnpeese
301 sesqgwller svpetwkafl esvkklgkgn qveaegadag qapeag (SEQ ID NO:19)
```

FIG. 14

Peripherin

```
  1 mshhpsglra gfsststsyrrt fgpppslspg afsysssssrf sssrllgsas psssvrlgsf
 61 rspragagal lrlpserldf smaealnqef lqelndrfan fiekvrfleq
121 qnaalrgels qargqepara dqlcqqelre lrrelellgr erdrvqverd glaedlaalk
181 qrleeetrkr edaehnlvlf rkdvddatls rlelerkies lmdeieflkk lheeelrdlq
241 vsvesqqvqq veveatvkpe ltaalrdira qyesiaaknl qeaeewyksk yadlsdaanr
301 nhealrqakq emnesrrqiq sltcevdglr gtneallrql releeqfale aggyqagaar
361 leeelrqlke emarhlreyq elnvkmald ieiatyrkll egeesrisvp vhsfaslnik
421 ttvpeveppq dshsrktvli ktietrngev vtesqkeqrs eldkssahsy (SEQ ID NO:20)
```

FIG. 15

RPGR-interacting protein-1

```
   1  mshlvdptsg  dlpvrdidai  plvlpaskgk  nmktqpplsr  mnreeledsf  frlredhmlv
  61  kelswkqqde  ikrlrttllr  ltaagrdlrv  aeeaaplset  arrgqkagwr  qrlsmhqrpq
 121  mhrlqghfhc  vgpasprraq  prvqvghrql  htagapvpek  pkrgprdrls  ytappsfkeh
 181  atnenrgeva  skpselvsgs  nsiisfssvi  smakpiglcm  pnsahimasn  tmqveeppks
 241  pekmwpkden  feqrssleca  qkaaelrasi  kekvelirlk  kllhernasl  vmtkaqltev
 301  qeayetllqk  nqgilsaahe  allkqvnelr  aelkeeskka  vslksqledv  silqmtlkef
 361  qervedleke  rkllndnydk  llesmldssd  sssqphwsne  liaeqlqqqv  sqlqdqldae
 421  ledkrkvlle  lsrekaqned  lklevtnilq  khkqevellq  kqevellq    naatisqppd  rqsepathpa
 481  vlqentqiep  sepknqeeek  lsqvlnelqv  shaettlele  ktrdmlilqr  kinvcyqeel
 541  eammtkadnd  nrdhkekler  ltrlldlknn  rikqlegilr  shdlptseql  kdvaygtrpl
 601  slcletlpah  gdedkvdisl  lhqgenlfel  hihqafltsa  alaqagdtqp  ttfctysfyd
 661  fethctplsv  gpqplydfts  qyvmetdslf  lhylqeasar  ldihqamase  hstlaagwic
 721  fdrvletvek  vhglatliga  ggeefgvley  wmrlrfpikp  slqacnkrkk  aqvylstdvl
 781  ggrkaqeeef  rseswepqne  lwieitkccg  lrsrwlgtqp  spyavyrfft  fsdhdtaiip
 841  asnnpyfrdq  arfpvlvtsd  ldhylrreal  sihvfdded1  epgsylgrar  vpllplakne
 901  sikgdfnltd  paekpngsiq  vqldwkfpyi  ppesflkpea  qtkgkdtkds  skisseeeka
 961  sfpsqdqmas  pevpieaggy  rskrkpphgg  erkekehqvv  sysrrkhgkr  igvqgknrme
1021  ylslnilngn  tpeqvnytew  kfsetnsfig  dgfknqheee  emtlshsalk  qkeplhpvnd
1081  kesseqgsev  seaqttdsdd  vivppmsqky  pkadsekmci  eivslafype  aevmsdenik
1141  qvyveykfyd  lplsetetpv  slrkpragee  ihfhfskvid  ldpqeqqgrr  rflfdmlnqq
1201  dpdqghlkft  vvsdpldeek  keceevgyay  lqlwqilesg  rdileqeldi  vspedlatpi
1261  grlkvslqaa  avlhaiykem  tedlfs  (SEQ ID NO:21)
```

FIG. 16

```
AAV1      --TFSYTFEEVPFHSSYAHSQSLDRLMNPLIDQYLYYLNRTQ-NQSGSAQNKDLLFSRGS  467
AAV6      --TFSYTFEDVPFHSSYAHSQSLDRLMNPLIDQYLYYLNRTQ-NQSGSAQNKDLLFSRGS  467
AAV3      ---FSYTFEDVPFHSSYAHSQSLDRLMNPLIDQYLYYLNRTQGTTSGTTNQSRLLFSQAG  467
AAV2      ---FSYTFEDVPFHSSYAHSQSLDRLMNPLIDQYLYYLNRTN-TPSGTTTQSRLQFSQAG  466
AAV8      NFQFTYTFEDVPFHSSYAHSQSLDRLMNPLIDQYLYYLSRTQT--GGTANTQTLGFSQGG  469
AAV8.1    NFQFTYTFEDVPFHSSYAHSQSLDRLMNPLIDQYLYYLSRTQT--GGTANTQTLGFSQGG  469
AAV8 rh8  FQFSYTFEDVPFHSSYAHSQSLDRLMNPLIDQYLYYLVRTQTTGTGGTQTLAFSQAGPS  469
AAV10     NFEFSYTFEDVPFHSSYAHSQSLDRLMNPLIDQYLYYLSRTQST-GGTQGTQQLLFSQAG  469
AAV7      -FEFSYSFEDVPFHSSYAHSQSLDRLMNPLIDQYLYYLARTQSNPGGTAGNRELQFYQGG  469
AAV9      -FQFSYEFENVPFHSSYAHSQSLDRLMNPLIDQYLYYLSKTI--NGSGQNQQTLKFSVAG  467
AAV9.1    -FQFSYEFENVPFHSSYAHSQSLDRLMNPLIDQYLYYLSKTI--NGSGQNQQTLKFSVAG  467
AAV5      NFEFTYNFEEVPFHSSFAPSQNLFKLANPLVDQYLYRFVSTN----NTGGVQFNKNL    453
              *   *:*******:.  *.*:   ** **:*** :                *

AAV1      PAGMSVQPKNWLPGPCYRQQRVSKTKTDNNNSNFTWTGASKYNLNGRESIINPGTAMASH  527
AAV6      PAGMSVQPKNWLPGPCYRQQRVSKTKTDNNNSNFTWTGASKYNLNGRESIINPGTAMASH  527
AAV3      PQSMSLQARNWLPGPCYRQQRLSKTANDNNNSNFPWTAASKYHLNGRDSLVNPGTAMASH  527
AAV2      ASDIRDQSRNWLPGPCYRQQRVSKTSADNNNSEYSWTGATKYHLNGRDSLVNPGPAMASH  526
AAV8      PNTMANQAKNWLPGPCYRQQRVSTTTGQNNNSNFAWTAGTKYHLNGRNSLANPGIAMATH  529
AAV8.1    PNTMANQAKNWLPGPCYRQQRVSTTTGQNNNSNFAWTAGTKYHLNGRNSLANPGIAMATH  529
AAV8 rh8  S--MANQARNWVPGPCYRQQRVSTTTNQNNNSNFAWTGAAKFKLNGRDSLMNPGVAMASH  527
AAV10     PANMSAQAKNWLPGPCYRQQRVSTTLSQNNNNSNFAWTGATKYHLNGRDSLVNPGVAMATH  529
AAV7      PSTMAEQAKNWLPGPCFRQQRVSKTLDQNNNNSNFAWTGATKYHLNGRNSLVNPGVAMATH  529
AAV9      PSNMAVQGRNYIPGPSYRQQRVSTTVTQNNNSEFAWPGASSWALNGRNSLMNPGPAMASH  527
AAV9.1    PSNMAVQGRNYIPGPSYRQQRVSTTVTQNNNSEFAWPGASSWALNGRNSLMNPGPAMASH  527
AAV5      AGRYANTYKNWFPGPMGRTQGWNLGSGVNRASVSAFATTNRMELEGASYQVPPQPNGMTN  513
            :   *.: .**  **  *.   .   :   .       :    *     .*

| | | |
|---|---|---|
| AAV1 | PQILIK- 650 | (SEQ ID NO:22) |
| AAV6 | PQILIK- 650 | (SEQ ID NO:23) |
| AAV3 | PQIMIK- 650 | (SEQ ID NO:24) |
| AAV2 | PQILIKN 650 | (SEQ ID NO:25) |
| AAV8 | PQILIKN 653 | (SEQ ID NO:26) |
| AAV8.1 | PQILIKN 653 | (SEQ ID NO:27) |
| AAV8 rh8 | PQILIKN 651 | (SEQ ID NO:28) |
| AAV10 | PQILIKN 653 | (SEQ ID NO:29) |
| AAV7 | PQILIKN 652 | (SEQ ID NO:30) |
| AAV9 | PQILIK- 650 | (SEQ ID NO:31) |
| AAV9.1 | PQILIK- 650 | (SEQ ID NO:32) |
| AAV5 | PMMLIKN 640 | (SEQ ID NO:33) |
| | * ::** | |

FIG. 17C

| | | |
|---|---|---|
| AAV1 | ---TFSYTFEEVPFHSSYAHSQSLDRLMNPLIDQYLYYLNRTQ-NQSGSAQNKDLLFSRGS | 467 |
| AAV6 | ---TFSYTFEDVPFHSSYAHSQSLDRLMNPLIDQYLYYLNRTQ-NQSGSAQNKDLLFSRGS | 467 |
| AAV3 | ---FSYTFEDVPFHSSYAHSQSLDRLMNPLIDQYLYYLNRTQGTTSGTTNQSRLLFSQAG | 467 |
| AAV2 | ---FSYTFEDVPFHSSYAHSQSLDRLMNPLIDQYLYYLNRSRTN-TPSGTTTQSRLQFSQAG | 466 |
| AAV8 | NFQFTYTFEDVPFHSSYAHSQSLDRLMNPLIDQYLYYLSRTQTT-GGTANTQTLGFSQGG | 469 |
| AAV8.1 | NFQFTYTFEDVPFHSSYAHSQSLDRLMNPLIDQYLYYLSRTQTT-GGTANTQTLGFSQGG | 469 |
| AAV8 rh8 | FQFSYTFEDVPFHSSYAHSQSLDRLMNPLIDQYLYYLVRTQTTGGTQTLAFSQAGPS | 469 |
| AAV10 | NFEFSYTFEDVPFHSSYAHSQSLDRLMNPLIDQYLYYLSRTQST-GGTQGTQQLLFSQAG | 469 |
| AAV7 | -FEFSYSFEDVPFHSSYAHSQSLDRLMNPLIDQYLYYLARTQSNPGGTAGNRELQFYQGG | 469 |
| AAV9 | -FQFSYEFENVPFHSSYAHSQSLDRLMNPLIDQYLYYLSKTI--NGSGQNQQTLKFSVAG | 467 |
| AAV9.1 | -FQFSYEFENVPFHSSYAHSQSLDRLMNPLIDQYLYYLSKTI--NGSGQNQQTLKFSVAG | 467 |
| AAV5 | NFEFTYNFEEVPFHSSFAPSQNLFKLANPLVDQYLYRFVSTN-------NTGGVQFNKNL | 453 |
| | | |
| AAV1 | PAGMSVQPKNWLPGPCYRQQRVSKTKTDNNNSNFTWTGASKYNLNGRESIINPGTAMASH | 527 |
| AAV6 | PAGMSVQPKNWLPGPCYRQQRVSKTKTDNNNSNFTWTGASKYNLNGRESIINPGTAMASH | 527 |
| AAV3 | PQSMSLQARNWLPGPCYRQQRVSKTKTDNNNSNFPWTAASKYHLNGRESIINPGTAMASH | 527 |
| AAV2 | ASDIRDQSRNWLPGPCYRQQRVSKTSADNNNSEYSWTGATKYHLNGRDSLVNPGPAMASH | 526 |
| AAV8 | PNTMANQAKNWLPGPCYRQQRVSTTTGQNNNSNFAWTAGTKYHLNGRNSLANPGIAMATH | 529 |
| AAV8.1 | PNTMANQAKNWLPGPCYRQQRVSTTTGQNNNSNFAWTAGTKYHLNGRNSLANPGIAMATH | 529 |
| AAV8 rh8 | S--MANQARNWVPGPCYRQQRVSTTTNQNNNSNFAWTGAAKFKLNGRDSLMNPGVAMASH | 527 |
| AAV10 | PANMSAQAKNWLPGPCYRQQRVSTTLSQNNNNSNFAWTGATKYHLNGRDSLVNPGVAMATH | 529 |
| AAV7 | PSTMAEQAKNWLPGPCFRQQRVSKTLDQNNNNSNFAWTGATKYHLNGRNSLVNPGVAMATH | 529 |
| AAV9 | PSNMAVQGRNYIPGPSYRQQRVSTTVTQNNNSEFAWPGASSWALNGRNSLMNPGPAMASH | 527 |
| AAV9.1 | PSNMAVQGRNYIPGPSYRQQRVSTTVTQNNNSEFAWPGASSWALNGRNSLMNPGPAMASH | 527 |
| AAV5 | AGRYANTYKNWFPGPMGRTQGWNLGSGVNRASVSAFATTNRMELEGASYQVPPQPNGMTN | 513 |

FIG. 18A

```
AAV1       KDDEDKFFPMSGVMIFGK--ESAGASNTALD-NVMITDEEEIKATNPVATERFGTVAVNF 584
AAV6       KDDKDKFFPMSGVMIFGK--ESAGASNTALD-NVMITDEEEIKATNPVATERFGTVAVNL 584
AAV3       KDDEEKFFPMHGNLIFGK--EGTTASNAELD-NVMITDEEEIRTTNPVATEQYGTVANNL 584
AAV2       KDDEEKFFPQSGVLIFGK--QGSEKTNVDIE-KVMITDEEEIRTTNPVATEQYGSVSTNL 583
AAV8       KDDEERFFPSNGILIFGK--QNAARDNADYS-DVMLTSEEEIKTTNPVATEEYGIVADNL 586
AAV8.1     KDDEERFFPSNGILIFGK--QNAARDNADYS-DVMLTSEEEIKTTNPVATEEYGIVADNL 586
AAV8 rh8   KDDDDRFFPSSGVLIFGK--QGAGNDGVDYS-QVLITDEEEIKATNPVATEEYGAVAINN 584
AAV10      KDDEERFFPSSGVLIFGK--QGAGRDNVDYS-SVMLTSEEEIKTTNPVATEQYGVVADNL 586
AAV7       KDDEDRFFPSSGVLMFGK--QGAT-NKTTLE-NVLMTNEEEIRPTNPVATEEYGIVSSNL 585
AAV9       KEGEDRFFPLSGSLIFGK--QGTGRDNVDAD-KVMITNEEEIKTTNPVATESYGQVATNH 584
AAV9.1     KEGEDRFFPLSGSLIFGK--QGTGRDNVDAD-KVMITNEEEIKTTNPVATESYGQVATNH 584
AAV5       NLQGSNTYALENTMIFNSQPANPGTTATYLEGNMLITSESETQPVNRVAYNVGGQMATNN 573

AAV1       QSSSTDLALGETTRPAPATGDVHAMGALPGMVWQDRDVYLQGPIWAKIPHTDGHFHPSPLMGGFGLKNPP
AAV6       QSSSTDLALGETTRPAPATGDVHVMGALPGMVWQDRDVYLQGPIWAKIPHTDGHFHPSPLMGGFGLKHPP
AAV3       QSSNTAPTTGTVNHQGALPGMVWQDRDVYLQGPIWAKIPHTDGHFHPSPLMGGFGLKHPP 644
AAV2       QRGNLALGETTRPARQAATADVNTQGVLPGMVWQDRDVYLQGPIWAKIPHTDGHFHPSPLMGGFGLKHPP
AAV8       QQQNLALGETTRPATAPQIGTVNSQGALPGMVWQNRDVYLQGPIWAKIPHTDGNFHPSPLMGGFGLKHPP
AAV8.1     QGQRGLGETTRPAQAAQIGTVNSQGALPGMVWQNRDVYLQGPIWAKIPHTDGNFHPSPLMGGFGLKHPP
AAV8 rh8   QAANLALGETTRPATQAQTGLVHNQGVIPGMVWQNRDVYLQGPIWAKIPHTDGNFHPSPLMGGFGLKHPP
AAV10      QQLALGETTRPAANTGPIVGNVNSQGALPGMVWQNRDVYLQGPIWAKIPHTDGNFHPSPLMGGFGLKHPP
AAV7       QAANLALGETTRPATAAQTQVVNNQGALPGMVWQNRDVYLQGPIWAKIPHTDGNFHPSPLMGGFGLKHPP
AAV9       QSAQLALGETTRPAQAQTGWVQNQGILPGMVWQDRDVYLQGPIWAKIPHTDGNFHPSPLMGGFGMKHPP
AAV9.1     QSGQLALGETTRPAQAATGWVQNQGILPGMVWQDRDVYLQGPIWAKIPHTDGNFHPSPLMGGFGMKHPP
AAV5       QSLALGETTRPASTTAPATGTYNLQEIVPGSVWMERDVYLQGPIWAKIPETGAHFHPSPAMGGFGLKHPP
```

FIG. 18B

| | | |
|---|---|---|
| AAV1 | PQILIK- | (SEQ ID NO:34) |
| AAV6 | PQILIK- | (SEQ ID NO:35) |
| AAV3 | PQIMIK- | (SEQ ID NO:24) |
| AAV2 | PQILIKN | (SEQ ID NO:36) |
| AAV8 | PQILIKN | (SEQ ID NO:37) |
| AAV8.1 | PQILIKN | (SEQ ID NO:38) |
| AAV8.1 rh8 | PQILIKN | (SEQ ID NO:39) |
| AAV10 | PQILIKN | (SEQ ID NO:40) |
| AAV7 | PQILIKN | (SEQ ID NO:41) |
| AAV9 | PQILIK- | (SEQ ID NO:42) |
| AAV9.1 | PQILIK- | (SEQ ID NO:43) |
| AAV5 | PMMLIKN | (SEQ ID NO:44) |

FIG. 18C

ADENO-ASSOCIATED VIRUS VIRIONS WITH VARIANT CAPSID AND METHODS OF USE THEREOF

CROSS-REFERENCE

This application claims the benefit of U.S. Provisional Patent Application No. 61/478,355, filed Apr. 22, 2011, which application is incorporated herein by reference in its entirety.

STATEMENT REGARDING FEDERALLY SPONSORED RESEARCH

This invention was made with government support under Grant Nos. EY016994-02 and EY018241 awarded by the National Eye Institute of the National Institutes of Health. The government has certain rights in the invention.

BACKGROUND

Photoreceptors are the first neurons in the retina to receive and process visual information, converting visible electromagnetic radiation into hyperpolarized responses through phototransduction. The overwhelming majority of inherited retinal diseases result in the loss of these cells, either directly, such as in dominant mutations that affect rhodopsin protein folding, or indirectly, such as in recessive mutations that affect retinal recycling pathways in the retinal pigment epithelium (RPE).

AAV belongs to the Parvoviridae family and *Dependovirus* genus, whose members require co-infection with a helper virus such as adenovirus to promote replication, and AAV establishes a latent infection in the absence of a helper. Virions are composed of a 25 nm icosahedral capsid encompassing a 4.9 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of viral transduction—including cell surface receptor binding, endocytosis, intracellular trafficking, and unpackaging in the nucleus.

LITERATURE

U.S. Patent Publication No. 2005/0053922; U.S. Patent Publication No. 2009/0202490; Allocca et al. (2007) *J. Virol.* 81:11372; Boucas et al. (2009) *J. Gene Med.* 11:1103.

SUMMARY OF THE INVENTION

The present disclosure provides adeno-associated virus (AAV) virions with altered capsid protein, where the AAV virions exhibit greater infectivity of a retinal cell, when administered via intravitreal injection, compared to wild-type AAV. The present disclosure further provides methods of delivering a gene product to a retinal cell in an individual, and methods of treating ocular disease.

BRIEF DESCRIPTION OF THE DRAWINGS

FIG. 2 depicts greater levels of intravitreal transduction by AAV2 7M8 variant (right), relative to AAV2 (left).

FIG. 5 provides an amino acid sequence of AAV2 VP1 (SEQ ID NO:1).

FIG. 6 provides amino acid sequences corresponding to amino acids 570-610 of AAV2 (FIG. 5) of AAV capsid protein VP1 of various AAV serotypes.

FIGS. 9A-E depict sustained improvements in retinal thickness measured at 10 months post 7m8-rho-RS1 treatment.

FIG. 10 provides an amino acid sequence of retinoschisin.

FIG. 11 provides an amino acid sequence of brain derived neurotrophic factor.

FIG. 12 provides an amino acid sequence of RPE65.

FIGS. 13A-C provide the nucleotide sequence of the 7m8-rho-RS1 construct.

FIG. 14 provides an amino acid sequence of peripherin-2.

FIG. 15 provides an amino acid sequence of peripherin.

FIG. 16 provides an amino acid sequence of retinitis pigmentosa GTPase regulator-interacting protein-1.

FIGS. 17A-C provide an alignment of amino acid sequences of AAV capsid protein loop IV (GH loop) regions. Insertion sites are shown in bold and underlining.

FIGS. 18A-C provide an alignment of amino acid sequences of AAV capsid protein GH loop regions, with heterologous peptide insertions.

DEFINITIONS

Figure 1:
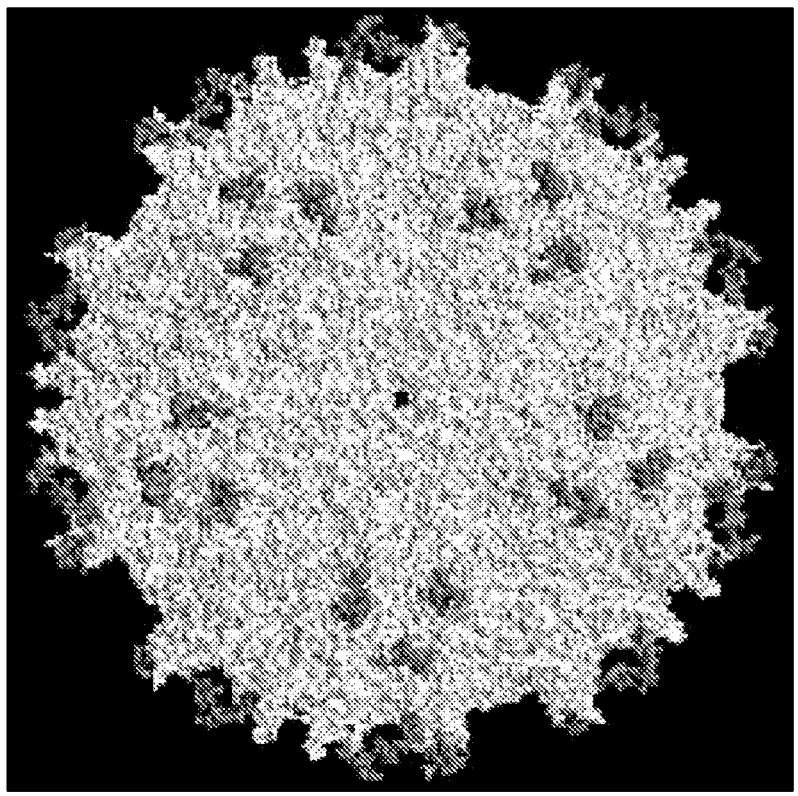
FIG. 1 provides a representative three-dimensional model of AAV2 containing a random heptamer following amino acid 587.

The term "retinal cell" can refer herein to any of the cell types that comprise the retina, such as retinal ganglion cells, amacrine cells, horizontal cells, bipolar cells, and photoreceptor cells including rods and cones, Müller glial cells, and retinal pigmented epithelium.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077 (AAV-1), AF063497 (AAV-1), NC_001401 (AAV-2), AF043303 (AAV-2), NC_001729 (AAV-3), NC_001829 (AAV-4), U89790 (AAV-4), NC_006152 (AAV-5), AF513851 (AAV-7), AF513852 (AAV-8), and NC_006261 (AAV-8); the disclosures of which are incorporated by reference herein for teaching AAV nucleic acid and amino acid sequences. See also, e.g., Srivistava et al. (1983) *J. Virology* 45:555; Chiorini et al. (1998) *J. Virology* 71:6823; Chiorini et al. (1999) *J. Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al. (1986) *J. Virol.* 58:921; Gao et al. (2002) *Proc. Nat. Acad. Sci. USA* 99:11854; Moris et al. (2004) *Virology* 33:375-383; international patent publications WO 00/28061, WO 99/61601, WO 98/11244; and U.S. Pat. No. 6,156,303.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids. An rAAV vector may either be single-stranded (ssAAV) or self-complementary (scAAV).

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

An "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11:S337 (describing a TCID50 infectious titer assay); and Zolotukhin et al. (1999) *Gene Ther.* 6:973. See also the Examples.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

Nucleic acid hybridization reactions can be performed under conditions of different "stringency". Conditions that increase stringency of a hybridization reaction of widely known and published in the art. See, e.g., Sambrook et al. *Molecular Cloning, A Laboratory Manual*, 2nd Ed., Cold Spring Harbor Laboratory Press, Cold Spring Harbor, N.Y., 1989, herein incorporated by reference. For example, see page 7.52 of Sambrook et al. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where 1×SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. As another example, stringent hybridization conditions comprise: prehybridization for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.2×SSC and 0.1% SDS (sodium dodecyl sulfate).

Stringent hybridization conditions are hybridization conditions that are at least as stringent as the above representative conditions. Other stringent hybridization conditions are known in the art and may also be employed to identify nucleic acids of this particular embodiment of the invention.

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log [X^+] + 0.41(\% G/C) - 0.61(\% F) - 600/L$$

where [$X^+$] is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

A "gene product" is a molecule resulting from expression of a particular gene. Gene products include, e.g., a polypeptide, an aptamer, an interfering RNA, an mRNA, and the like.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

A "short hairpin RNA," or shRNA, is a polynucleotide construct that can be made to express an interfering RNA such as siRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a recombinant AAV virion" includes a plurality of such virions and reference to "the photoreceptor cell" includes reference to one or more photoreceptor cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides adeno-associated virus (AAV) virions with altered capsid protein, where the AAV virions exhibit greater infectivity of a retinal cell, when administered via intravitreal injection, compared to wild-type AAV when administered via intravitreal injection. The present disclosure further provides methods of delivering a gene product to a retinal cell in an individual, and methods of treating ocular disease.

The retinal cell can be a photoreceptor (e.g., rods; cones), a retinal ganglion cell (RGC), a Müller cell (a Müller glial cell), a bipolar cell, an amacrine cell, a horizontal cell, or a retinal pigmented epithelium (RPE) cell.

Variant AAV Capsid Polypeptides

The present disclosure provides a variant AAV capsid protein, where the variant AAV capsid protein comprises an insertion of from about 5 amino acids to about 11 amino acids in an insertion site in the capsid protein GH loop or loop IV, relative to a corresponding parental AAV capsid protein, and where the variant capsid protein, when present in an AAV virion, confers increased infectivity of a retinal cell compared to the infectivity of the retinal cell by an AAV virion comprising the corresponding parental AAV capsid protein. In some cases, the retinal cell is a photoreceptor cell (e.g., rods; cones). In other cases, the retinal cell is an RGC. In other cases, the retinal cell is an RPE cell. In other cases, the retinal cell is a Müller cell. Other retinal cells include amacrine cells, bipolar cells, and horizontal cells. An "insertion of from about 5 amino acids to about 11 amino acids" is also referred to herein as a "peptide insertion" (e.g., a heterologous peptide insertion). A "corresponding parental AAV capsid protein" refers to an AAV capsid protein of the same AAV serotype, without the peptide insertion.

The insertion site is in the GH loop, or loop IV, of the AAV capsid protein, e.g., in a solvent-accessible portion of the GH loop, or loop IV, of the AAV capsid protein. For the GH loop/loop IV of AAV capsid, see, e.g., van Vliet et al. (2006) Mol. Ther. 14:809; Padron et al. (2005) J. Virol. 79:5047; and Shen et al. (2007) Mol. Ther. 15:1955. For example, the insertion site can be within amino acids 411-650 of an AAV capsid protein, as depicted in FIGS. 17A and 17B. For example, the insertion site can be within amino acids 570-611 of AAV2, within amino acids 571-612 of AAV1, within amino acids 560-601 of AAV5, within amino acids 571 to 612 of AAV6, within amino acids 572 to 613 of AAV7, within amino acids 573 to 614 of AAV8, within amino acids 571 to 612 of AAV9, or within amino acids 573 to 614 of AAV10, as depicted in FIG. 6.

In some cases, from about 5 amino acids to about 11 amino acids are inserted in an insertion site in the GH loop or loop IV of the capsid protein relative to a corresponding parental AAV capsid protein. For example, the insertion site can be between amino acids 587 and 588 of AAV2, or the corresponding positions of the capsid subunit of another AAV serotype. It should be noted that the insertion site 587/588 is based on an AAV2 capsid protein. From about 5 amino acids to about 11 amino acids can be inserted in a corresponding site in an AAV serotype other than AAV2 (e.g., AAV8, AAV9, etc.). Those skilled in the art would know, based on a comparison of the amino acid sequences of capsid proteins of various AAV serotypes, where an insertion site "corresponding to amino acids 587-588 of AAV2" would be in a capsid protein of any given AAV serotype. Sequences corresponding to amino acids 570-611 of capsid protein VP1 of AAV2 (see FIG. 5) in various AAV serotypes are shown in FIG. 6. See, e.g., GenBank Accession No. NP_049542 for AAV1; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9 and GenBank Accession No. AAT46337 for AAV10.

In some embodiments, the insertion site is a single insertion site between two adjacent amino acids located between amino acids 570-614 of VP1 of any AAV serotype, e.g., the insertion site is between two adjacent amino acids located in amino acids 570-610, amino acids 580-600, amino acids 570-575, amino acids 575-580, amino acids 580-585, amino acids 585-590, amino acids 590-600, or amino acids 600-614, of VP1 of any AAV serotype or variant. For example, the insertion site can be between amino acids 580 and 581, amino acids 581 and 582, amino acids 583 and 584, amino acids 584 and 585, amino acids 585 and 586, amino acids 586 and 587, amino acids 587 and 588, amino acids 588 and 589, or amino acids 589 and 590. The insertion site can be between amino acids 575 and 576, amino acids 576 and 577, amino acids 577 and 578, amino acids 578 and 579, or amino acids 579 and 580. The insertion site can be between amino acids 590 and 591, amino acids 591 and 592, amino acids 592 and 593, amino acids 593 and 594, amino acids 594 and 595, amino acids 595 and 596, amino acids 596 and 597, amino acids 597 and 598, amino acids 598 and 599, or amino acids 599 and 600.

For example, the insertion site can be between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

As another example, the insertion site can be between amino acids 450 and 460 of an AAV capsid protein, as shown in FIG. 17A. For example, the insertion site can be at (e.g., immediately N-terminal to) amino acid 453 of AAV2, at amino acid 454 of AAV1, at amino acid 454 of AAV6, at amino acid 456 of AAV7, at amino acid 456 of AAV8, at amino acid 454 of AAV9, or at amino acid 456 of AAV10, as shown in FIG. 17A.

In some embodiments, a subject capsid protein includes a GH loop comprising an amino acid sequence having at least about 85%, at least about 90%, at least about 95%, at least about 98%, at least about 99%, or 100%, amino acid sequence identity to an amino acid sequence set forth in FIG. 18A-C.

Insertion Peptides

As noted above, a peptide of from about 5 amino acids to about 11 amino acids in length is inserted into the GH loop of an AAV capsid. The insertion peptide has a length of 5 amino acids, 6 amino acids, 7 amino acids, 8 amino acids, 9 amino acids, 10 amino acids, or 11 amino acids.

The insertion peptide can comprise an amino acid sequence of any one of the formulas set forth below.

For example, an insertion peptide can be a peptide of from 5 to 11 amino acids in length, where the insertion peptide is of Formula I:

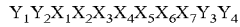

where:
each of $Y_1$-$Y_4$, if present, is independently selected from Ala, Leu, Gly, Ser, and Thr;
$X_1$, if present, is selected from Leu, Asn, and Lys;
$X_2$ is selected from Gly, Glu, Ala, and Asp;
$X_3$ is selected from Glu, Thr, Gly, and Pro;
$X_4$ is selected from Thr, Ile, Gln, and Lys;
$X_5$ is selected from Thr and Ala;
$X_6$ is selected from Arg, Asn, and Thr;
$X_7$, if present, is selected from Pro and Asn.

As another example, an insertion peptide can be a peptide of from 5 to 11 amino acids in length, where the insertion peptide is of Formula IIa:

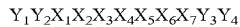

where:
each of $Y_1$-$Y_4$, if present, is independently selected from Ala, Leu, Gly, Ser, and Thr;
each of $X_1$-$X_4$ is any amino acid;
$X_5$ is Thr;
$X_6$ is Arg; and
$X_7$ is Pro.

As another example, an insertion peptide can be a peptide of from 5 to 11 amino acids in length, where the insertion peptide is of Formula IIb:

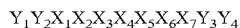

where:
each of $Y_1$-$Y_4$, if present, is independently selected from Ala, Leu, Gly, Ser, and Thr;

$X_1$, if present, is selected from Leu and Asn;
$X_2$, if present, is selected from Gly and Glu;
$X_3$ is selected from Glu and Thr;
$X_4$ is selected from Thr and Ile;
$X_5$ is Thr;
$X_6$ is Arg; and
$X_7$ is Pro.

As another example, an insertion peptide can be a peptide of from 5 to 11 amino acids in length, where the insertion peptide is of Formula III:

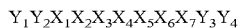

where:
each of $Y_1$-$Y_4$, if present, is independently selected from Ala, Leu, Gly, Ser, and Thr;
$X_1$, if present, is Lys;
$X_2$ is selected from Ala and Asp;
$X_3$ is selected from Gly and Pro;
$X_4$ is selected from Gln and Lys;
$X_5$ is selected from Thr and Ala;
$X_6$ is selected from Asn and Thr;
$X_7$, if present, is Asn.

As another example, an insertion peptide can be a peptide of from 5 to 11 amino acids in length, where the insertion peptide is of Formula IV:

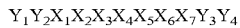

where:
each of $Y_1$-$Y_4$, if present, is independently selected from Ala, Leu, Gly, Ser, and Thr;
$X_1$, if present, is a positively charged amino acid or an uncharged amino acid; or is selected from Leu, Asn, Arg, Ala, Ser, and Lys;
$X_2$ is a negatively charged amino acid or an uncharged amino acid; or is selected from Gly, Glu, Ala, Val, Thr, and Asp;
$X_3$ is a negatively charged amino acid or an uncharged amino acid; or is selected from Glu, Thr, Gly, Asp, or Pro;
$X_4$ is selected from Thr, Ile, Gly, Lys, Asp, and Gln;
$X_5$ is a polar amino acid, an alcohol (an amino acid having a free hydroxyl group), or a hydrophobic amino acid; or is selected from Thr, Ser, Val, and Ala;
$X_6$ is a positively charged amino acid or an uncharged amino acid; or is selected from Arg, Val, Lys, Pro, Thr, and Asn; and
$X_7$, if present, is a positively charged amino acid or an uncharged amino acid; or is selected from Pro, Gly, Phe, Asn, and Arg.

As non-limiting examples, the insertion peptide can comprise an amino acid sequence selected from LGETTRP (SEQ ID NO:13), NETITRP (SEQ ID NO:14), KAGQANN (SEQ ID NO:15), KDPKTTN (SEQ ID NO:16), KDTDTTR (SEQ ID NO:57), RAGGSVG (SEQ ID NO:58), AVDTTKF (SEQ ID NO:59), and STGKVPN (SEQ ID NO:60).

In some cases, the insertion peptide has from 1 to 4 spacer amino acids ($Y_1$-$Y_4$) at the amino terminus and/or at the carboxyl terminus of any one of LGETTRP (SEQ ID NO:13), NETITRP (SEQ ID NO:14), KAGQANN (SEQ ID NO:15), KDPKTTN (SEQ ID NO:16), KDTDTTR (SEQ ID NO:57), RAGGSVG (SEQ ID NO:58), AVDTTKF (SEQ ID NO:59), and STGKVPN (SEQ ID NO:60). Suitable spacer amino acids include, but are not limited to, leucine, alanine, glycine, and serine.

For example, in some cases, an insertion peptide has one of the following amino acid sequences: LALGETTRPA (SEQ ID NO:45); LANETITRPA (SEQ ID NO:46), LAKAGQANNA (SEQ ID NO:47), LAKDPKTTNA (SEQ ID NO:48), LAKDTDTTRA (SEQ ID NO:61), LARAGGS- VGA (SEQ ID NO:62), LAAVDTTKFA (SEQ ID NO:63), and LASTGKVPNA (SEQ ID NO:64). As another example, in some cases, an insertion peptide has one of the following amino acid sequences: AALGETTRPA (SEQ ID NO:49); AANETITRPA (SEQ ID NO:50), AAKAGQANNA (SEQ ID NO:51), and AAKDPKTTNA (SEQ ID NO:52). As yet another example, in some cases, an insertion peptide has one of the following amino acid sequences: GLGETTRPA (SEQ ID NO:53); GNETITRPA (SEQ ID NO:54), GKAGQANNA (SEQ ID NO:55), and GKDPKTTNA (SEQ ID NO:56). As another example, in some cases, an insertion peptide comprises one of KDTDTTR (SEQ ID NO:57), RAGGSVG (SEQ ID NO:58), AVDTTKF (SEQ ID NO:59), and STGKVPN (SEQ ID NO:60), flanked on the C-terminus by AA and on the N-terminus by A; or comprises one of KDTDTTR (SEQ ID NO:57), RAGGSVG (SEQ ID NO:58), AVDTTKF (SEQ ID NO:59), and STGKVPN (SEQ ID NO:60) flanked on the C-terminus by G and on the N-terminus by A.

In some embodiments, a subject variant AAV capsid does not include any other amino acid substitutions, insertions, or deletions, other than an insertion of from about 5 amino acids to about 11 amino acids in the GH loop or loop IV relative to a corresponding parental AAV capsid protein. In other embodiments, a subject variant AAV capsid includes from 1 to about 25 amino acid insertions, deletions, or substitutions, compared to the parental AAV capsid protein, in addition to an insertion of from about 5 amino acids to about 11 amino acids in the GH loop or loop IV relative to a corresponding parental AAV capsid protein. For example, in some embodiments, a subject variant AAV capsid includes from 1 to about 5, from about 5 to about 10, from about 10 to about 15, from about 15 to about 20, or from about 20 to about 25 amino acid insertions, deletions, or substitutions, compared to the parental AAV capsid protein, in addition to an insertion of from about 5 amino acids to about 11 amino acids in the GH loop or loop IV relative to a corresponding parental AAV capsid protein.

In some embodiments, a subject variant capsid polypeptide does not include one, two, three, or four, of the following amino acid substitutions: Y273F, Y444F, Y500F, and Y730F.

In some embodiments, a subject variant capsid polypeptide comprises, in addition to an insertion peptide as described above, one, two, three, or four, of the following amino acid substitutions: Y273F, Y444F, Y500F, and Y730F.

In some embodiments, a variant AAV capsid polypeptide is a chimeric capsid, e.g., the capsid comprises a portion of an AAV capsid of a first AAV serotype and a portion of an AAV capsid of a second serotype; and comprises an insertion of from about 5 amino acids to about 11 amino acids in the GH loop or loop IV relative to a corresponding parental AAV capsid protein.

In some embodiments, a subject variant capsid protein comprises an amino acid sequence having at least about 85%, at least about 90%, at least about 95%, at least about 98%, or at least about 99%, amino acid sequence identity to the amino acid sequence provided in FIG. 5; and an insertion of from about 5 amino acids to about 11 amino acids in the GH loop or loop IV relative to a corresponding parental AAV capsid protein.

In some embodiments, a subject variant capsid protein is isolated, e.g., purified. In some cases, a subject variant capsid protein is included in an AAV vector, which is also provided. As described in detail below, a subject variant capsid protein can be included in a recombinant AAV virion.

Recombinant AAV Virion

The present disclosure provides a recombinant adeno-associated virus (rAAV) virion comprising: a) a variant AAV capsid protein, where the variant AAV capsid protein comprises an insertion of from about 5 amino acids to about 11 amino acids in an insertion site in the capsid protein GH loop or loop IV, relative to a corresponding parental AAV capsid protein, and where the variant capsid protein confers increased infectivity of a retinal cell compared to the infectivity of the retinal cell by an AAV virion comprising the corresponding parental AAV capsid protein; and b) a heterologous nucleic acid comprising a nucleotide sequence encoding a gene product. In some cases, the retinal cell is a photoreceptor cell (e.g., rods and/or cones). In other cases, the retinal cell is an RGC cell. In other cases, the retinal cell is an RPE cell. In other cases, the retinal cell is a Müller cell. In other cases, retinal cells may include amacrine cells, bipolar cells, and horizontal cells. An "insertion of from about 5 amino acids to about 11 amino acids" is also referred to herein as a "peptide insertion" (e.g., a heterologous peptide insertion). A "corresponding parental AAV capsid protein" refers to an AAV capsid protein of the same AAV serotype, without the peptide insertion.

The insertion site is in the GH loop, or loop IV, of the AAV capsid protein, e.g., in a solvent-accessible portion of the GH loop, or loop IV, of the AAV capsid protein. For the GH loop, see, e.g., van Vliet et al. (2006) *Mol. Ther.* 14:809; Padron et al. (2005) *J. Virol.* 79:5047; and Shen et al. (2007) *Mol. Ther.* 15:1955. For example, the insertion site is within amino acids 570-611 of AAV2, within amino acids 571-612 of AAV1, within amino acids 560-601 of AAV5, within amino acids 571 to 612 of AAV6, within amino acids 572 to 613 of AAV7, within amino acids 573 to 614 of AAV8, within amino acids 571 to 612 of AAV9, or within amino acids 573 to 614 of AAV10.

From about 5 amino acids to about 11 amino acids are inserted in an insertion site in the GH loop or loop IV of the capsid protein relative to a corresponding parental AAV capsid protein. For example, the insertion site can be between amino acids 587 and 588 of AAV2, or the corresponding positions of the capsid subunit of another AAV serotype. It should be noted that the insertion site 587/588 is based on an AAV2 capsid protein. From about 5 amino acids to about 11 amino acids can be inserted in a corresponding site in an AAV serotype other than AAV2 (e.g., AAV8, AAV9, etc.). Those skilled in the art would know, based on a comparison of the amino acid sequences of capsid proteins of various AAV serotypes, where an insertion site "corresponding to amino acids 587-588 of AAV2" would be in a capsid protein of any given AAV serotype. Sequences corresponding to amino acids 570-611 of capsid protein VP1 of AAV2 (see FIG. 5) in various AAV serotypes are shown in FIG. 6.

In some embodiments, the insertion site is a single insertion site between two adjacent amino acids located between amino acids 570-614 of VP1 of any AAV serotype, e.g., the insertion site is between two adjacent amino acids located in amino acids 570-614, amino acids 580-600, amino acids 570-575, amino acids 575-580, amino acids 580-585, amino acids 585-590, amino acids 590-600, or amino acids 600-610, of VP1 of any AAV serotype or variant. For example, the insertion site can be between amino acids 580 and 581, amino acids 581 and 582, amino acids 583 and 584, amino acids 584 and 585, amino acids 585 and 586, amino acids 586 and 587, amino acids 587 and 588, amino acids 588 and 589, or amino acids 589 and 590. The insertion site can be between amino acids 575 and 576, amino acids 576 and 577, amino acids 577 and 578, amino acids 578 and 579, or amino acids 579 and 580. The insertion site can be between amino acids 590 and 591, amino acids 591 and 592, amino acids 592 and 593, amino acids 593 and 594, amino acids 594 and 595, amino acids 595 and 596, amino acids 596 and 597, amino acids 597 and 598, amino acids 598 and 599, or amino acids 599 and 600.

For example, the insertion site can be between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 589 and 590 of AAV10.

Insertion Peptides

As noted above, a subject rAAV virion comprises a peptide of from about 5 amino acids to about 11 amino acids in length inserted into the GH loop of the AAV capsid. The insertion peptide has a length of 5 amino acids, 6 amino acids, 7 amino acids, 8 amino acids, 9 amino acids, 10 amino acids, or 11 amino acids.

The insertion peptide can comprise an amino acid sequence of any one of the formulas set forth below.

For example, an insertion peptide can be a peptide of from 5 to 11 amino acids in length, where the insertion peptide is of Formula I:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is selected from Leu, Asn, and Lys;
$X_2$ is selected from Gly, Glu, Ala, and Asp;
$X_3$ is selected from Glu, Thr, Gly, and Pro;
$X_4$ is selected from Thr, Ile, Gln, and Lys;
$X_5$ is selected from Thr and Ala;
$X_6$ is selected from Arg, Asn, and Thr;
$X_7$, if present, is selected from Pro and Asn.

As another example, an insertion peptide can be a peptide of from 5 to 11 amino acids in length, where the insertion peptide is of Formula IIa:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
each of $X_1$-$X_4$ is any amino acid;
$X_5$ is Thr;
$X_6$ is Arg; and
$X_7$ is Pro.

As another example, an insertion peptide can be a peptide of from 5 to 11 amino acids in length, where the insertion peptide is of Formula IIb:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is selected from Leu and Asn;
$X_2$, if present, is selected from Gly and Glu;
$X_3$ is selected from Glu and Thr;
$X_4$ is selected from Thr and Ile;
$X_5$ is Thr;
$X_6$ is Arg; and
$X_7$ is Pro.

As another example, an insertion peptide can be a peptide of from 5 to 11 amino acids in length, where the insertion peptide is of Formula III:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;

$X_1$, if present, is Lys;
$X_2$ is selected from Ala and Asp;
$X_3$ is selected from Gly and Pro;
$X_4$ is selected from Gln and Lys;
$X_5$ is selected from Thr and Ala;
$X_6$ is selected from Asn and Thr;
$X_7$, if present, is Asn.

As another example, an insertion peptide can be a peptide of from 5 to 11 amino acids in length, where the insertion peptide is of Formula IV:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is a positively charged amino acid or an uncharged amino acid; or is selected from Leu, Asn, Arg, Ala, Ser, and Lys;
$X_2$ is a negatively charged amino acid or an uncharged amino acid; or is selected from Gly, Glu, Ala, Val, Thr, and Asp;
$X_3$ is a negatively charged amino acid or an uncharged amino acid; or is selected from Glu, Thr, Gly, Asp, or Pro;
$X_4$ is selected from Thr, Ile, Gly, Lys, Asp, and Gln;
$X_5$ is a polar amino acid, an alcohol (an amino acid having a free hydroxyl group), or a hydrophobic amino acid; or is selected from Thr, Ser, Val, and Ala;
$X_6$ is a positively charged amino acid or an uncharged amino acid; or is selected from Arg, Val, Lys, Pro, Thr, and Asn; and
$X_7$, if present, is a positively charged amino acid or an uncharged amino acid; or is selected from Pro, Gly, Phe, Asn, and Arg.

As non-limiting examples, the insertion peptide can comprise an amino acid sequence selected from LGETTRP (SEQ ID NO:13), NETITRP (SEQ ID NO:14), KAGQANN (SEQ ID NO:15), KDPKTTN (SEQ ID NO:16), KDTDTTR (SEQ ID NO:57), RAGGSVG (SEQ ID NO:58), AVDTTKF (SEQ ID NO:59), and STGKVPN (SEQ ID NO:60).

In some cases, the insertion peptide has from 1 to 4 spacer amino acids ($Y_1$-$Y_4$) at the amino terminus and/or at the carboxyl terminus of any one of LGETTRP (SEQ ID NO:13), NETITRP (SEQ ID NO:14), KAGQANN (SEQ ID NO:15), KDPKTTN (SEQ ID NO:16), KDTDTTR (SEQ ID NO:57), RAGGSVG (SEQ ID NO:58), AVDTTKF (SEQ ID NO:59), and STGKVPN (SEQ ID NO:60). Suitable spacer amino acids include, but are not limited to, leucine, alanine, glycine, and serine.

For example, in some cases, an insertion peptide has one of the following amino acid sequences: LALGETTRPA (SEQ ID NO:45); LANETITRPA (SEQ ID NO:46), LAKAGQANNA (SEQ ID NO:47), LAKDPKTTNA (SEQ ID NO:48), LAKDTDTTRA (SEQ ID NO:61), LARAGGSVGA (SEQ ID NO:62), LAAVDTTKFA (SEQ ID NO:63), and LASTGKVPNA (SEQ ID NO:64). As another example, in some cases, an insertion peptide has one of the following amino acid sequences: AALGETTRPA (SEQ ID NO:49); AANETITRPA (SEQ ID NO:50), AAKAGQANNA (SEQ ID NO:51), and AAKDPKTTNA (SEQ ID NO:52). As yet another example, in some cases, an insertion peptide has one of the following amino acid sequences: GLGETTRPA (SEQ ID NO:53); GNETITRPA (SEQ ID NO:54), GKAGQANNA (SEQ ID NO:55), and GKDPKTTNA (SEQ ID NO:56). As another example, in some cases, an insertion peptide comprises one of KDTDTTR (SEQ ID NO:57), RAGGSVG (SEQ ID NO:58), AVDTTKF (SEQ ID NO:59), and STGKVPN (SEQ ID NO:60), flanked on the C-terminus by AA and on the N-terminus by A; or comprises one of KDT- DTTR (SEQ ID NO:57), RAGGSVG (SEQ ID NO:58), AVDTTKF (SEQ ID NO:59), and STGKVPN (SEQ ID NO:60) flanked on the C-terminus by G and on the N-terminus by A.

In some embodiments, a subject rAAV virion capsid does not include any other amino acid substitutions, insertions, or deletions, other than an insertion of from about 7 amino acids to about 10 amino acids in the GH loop or loop IV relative to a corresponding parental AAV capsid protein. In other embodiments, a subject rAAV virion capsid includes from 1 to about 25 amino acid insertions, deletions, or substitutions, compared to the parental AAV capsid protein, in addition to an insertion of from about 7 amino acids to about 10 amino acids in the GH loop or loop IV relative to a corresponding parental AAV capsid protein. For example, in some embodiments, a subject rAAV virion capsid includes from 1 to about 5, from about 5 to about 10, from about 10 to about 15, from about 15 to about 20, or from about 20 to about 25 amino acid insertions, deletions, or substitutions, compared to the parental AAV capsid protein, in addition to an insertion of from about 7 amino acids to about 10 amino acids in the GH loop or loop IV relative to a corresponding parental AAV capsid protein.

In some embodiments, a subject rAAV virion capsid does not include one, two, three, or four, of the following amino acid substitutions: Y273F, Y444F, Y500F, and Y730F.

In some embodiments, a subject variant capsid polypeptide comprises, in addition to an insertion peptide as described above, one, two, three, or four, of the following amino acid substitutions: Y273F, Y444F, Y500F, and Y730F.

In some embodiments, a subject rAAV virion capsid is a chimeric capsid, e.g., the capsid comprises a portion of an AAV capsid of a first AAV serotype and a portion of an AAV capsid of a second serotype; and comprises an insertion of from about 5 amino acids to about 11 amino acids in the GH loop or loop IV relative to a corresponding parental AAV capsid protein.

In some embodiments, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 5; and an insertion of from about 5 amino acids to about 11 amino acids in the GH loop or loop IV relative to a corresponding parental AAV capsid protein.

In some embodiments, a subject rAAV virion comprises a capsid protein that includes a GH loop comprising an amino acid sequence having at least about 85%, at least about 90%, at least about 95%, at least about 98%, at least about 99%, or 100%, amino acid sequence identity to an amino acid sequence set forth in FIG. 18A-C.

A subject rAAV virion exhibits at least 10-fold, at least 15-fold, at least 20-fold, at least 25-fold, at least 50-fold, or more than 50-fold, increased infectivity of a retinal cell, compared to the infectivity of the retinal cell by an AAV virion comprising the corresponding parental AAV capsid protein.

In some cases, a subject rAAV virion exhibits at least 10-fold, at least 15-fold, at least 20-fold, at least 25-fold, at least 50-fold, or more than 50-fold, increased infectivity of a retinal cell, when administered via intravitreal injection, compared to the infectivity of the retinal cell by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of a photoreceptor (rod or cone) cell, compared to the infectivity of the photoreceptor cell by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of a photoreceptor (rod or cone) cell, when administered via intravitreal injection, compared to the infectivity of the photoreceptor cell by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of an RGC, compared to the infectivity of the RGC by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of an RGC, when administered via intravitreal injection, compared to the infectivity of the RGC by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of an RPE cell, compared to the infectivity of the RPE cell by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of an RPE cell, when administered via intravitreal injection, compared to the infectivity of the RPE cell by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of a Müller cell, compared to the infectivity of the Müller cell by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of a Müller cell, when administered via intravitreal injection, compared to the infectivity of the Müller cell by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of a bipolar cell, compared to the infectivity of the bipolar cell by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of a bipolar cell, when administered via intravitreal injection, compared to the infectivity of the bipolar cell by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of an amacrine cell, compared to the infectivity of the amacrine cell by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of an amacrine cell, when administered via intravitreal injection, compared to the infectivity of the amacrine cell by an AAV virion comprising the corresponding parental AAV capsid protein, when administered via intravitreal injection.

In some embodiments, a subject rAAV virion exhibits at least 10-fold, at least 15-fold, at least 20-fold, at least 25-fold, at least 50-fold, or more than 50-fold, increased infectivity of a horizontal cell, compared to the infectivity of the horizontal cell by an AAV virion comprising the corresponding parental AAV capsid protein.

In some embodiments, a subject rAAV virion exhibits at least 10-fold, at least 15-fold, at least 20-fold, at least 25-fold, at least 50-fold, or more than 50-fold, increased infectivity of a horizontal cell, when administered via intravitreal injection, compared to the infectivity of the horizontal cell by an AAV virion comprising the corresponding parental AAV capsid protein, when administered via intravitreal injection.

In some cases, a subject rAAV virion exhibits at least 10-fold, at least 15-fold, at least 20-fold, at least 25-fold, at least 50-fold, or more than 50-fold, increased ability to cross the internal limiting membrane (ILM), compared to the ability of an AAV virion comprising the corresponding parental AAV capsid protein to cross the ILM.

In some cases, a subject rAAV virion exhibits at least 10-fold, at least 15-fold, at least 20-fold, at least 25-fold, at least 50-fold, or more than 50-fold, increased ability, when administered via intravitreal injection, to cross the internal limiting membrane (ILM), compared to the ability of an AAV virion comprising the corresponding parental AAV capsid protein to cross the ILM when administered via intravitreal injection.

A subject rAAV virion can cross the ILM, and can also traverse cell layers, including Müller cells, amacrine cells, etc., to reach the photoreceptor cells and or RPE cells. For example, a subject rAAV virion, when administered via intravitreal injection, can cross the ILM, and can also traverse cell layers, including Müller cells, amacrine cells, etc., to reach the photoreceptor cells and or RPE cells.

In some embodiments, a subject rAAV virion selectively infects a retinal cell, e.g., a subject rAAV virion infects a retinal cell with 10-fold, 15-fold, 20-fold, 25-fold, 50-fold, or more than 50-fold, specificity than a non-retinal cell, e.g., a cell outside the eye. For example, in some embodiments, a subject rAAV virion selectively infects a retinal cell, e.g., a subject rAAV virion infects a photoreceptor cell with 10-fold, 15-fold, 20-fold, 25-fold, 50-fold, or more than 50-fold, specificity than a non-retinal cell, e.g., a cell outside the eye.

In some embodiments, a subject rAAV virion selectively infects a photoreceptor cell, e.g., a subject rAAV virion infects a photoreceptor cell with 10-fold, 15-fold, 20-fold, 25-fold, 50-fold, or more than 50-fold, specificity than a non-photoreceptor cell present in the eye, e.g., a retinal ganglion cell, a Müller cell, etc.

In some embodiments, a subject rAAV virion exhibits at least 10-fold, at least 15-fold, at least 20-fold, at least 25-fold, at least 50-fold, or more than 50-fold, increased infectivity of a photoreceptor cell, when administered via intravitreal injection, compared to the infectivity of the photoreceptor cell by an AAV virion comprising the corresponding parental AAV capsid protein, when administered via intravitreal injection.

Gene Products

A subject rAAV virion comprises a heterologous nucleic acid comprising a nucleotide sequence encoding a gene product. In some embodiments, the gene product is an interfering RNA. In some embodiments, the gene product is an aptamer. In some embodiments, the gene product is a polypeptide. In some embodiments, the gene product is a site-specific nuclease that provide for site-specific knock-down of gene function.

Interfering RNA

Where the gene product is an interfering RNA (RNAi), suitable RNAi include RNAi that decrease the level of an apoptotic or angiogenic factor in a cell. For example, an RNAi can be an shRNA or siRNA that reduces the level of a gene product that induces or promotes apoptosis in a cell. Genes whose gene products induce or promote apoptosis are referred to herein as "pro-apoptotic genes" and the products of those genes (mRNA; protein) are referred to as "pro-apoptotic gene products." Pro-apoptotic gene products include, e.g., Bax, Bid, Bak, and Bad gene products. See, e.g., U.S. Pat. No. 7,846,730.

Interfering RNAs could also be against an angiogenic product, for example VEGF (e.g., Cand5; see, e.g., U.S. Patent Publication No. 2011/0143400; U.S. Patent Publication No. 2008/0188437; and Reich et al. (2003) Mol. Vis. 9:210), VEGFR1 (e.g., Sirna-027; see, e.g., Kaiser et al. (2010) Am. J. Ophthalmol. 150:33; and Shen et al. (2006) Gene Ther. 13:225), or VEGFR2 (Kou et al. (2005) Biochem. 44:15064). See also, U.S. Pat. Nos. 6,649,596, 6,399,586, 5,661,135, 5,639,872, and 5,639,736; and U.S. Pat. Nos. 7,947,659 and 7,919,473.

Aptamers

Where the gene product is an aptamer, exemplary aptamers of interest include an aptamer against vascular endothelial growth factor (VEGF). See, e.g., Ng et al. (2006) Nat. Rev. Drug Discovery 5:123; and Lee et al. (2005) Proc. Natl. Acad. Sci. USA 102:18902. For example, a VEGF aptamer can comprise the nucleotide sequence 5'-cgcaaucagugaaugcuuauacauccg-3' (SEQ ID NO:17). Also suitable for use is a PDGF-specific aptamer, e.g., E10030; see, e.g., Ni and Hui (2009) Ophthalmologica 223:401; and Akiyama et al. (2006) J. Cell Physiol. 207:407).

Polypeptides

Where the gene product is a polypeptide, the polypeptide is generally a polypeptide that enhances function of a retinal cell, e.g., the function of a rod or cone photoreceptor cell, a retinal ganglion cell, a Müller cell, a bipolar cell, an amacrine cell, a horizontal cell, or a retinal pigmented epithelial cell. Exemplary polypeptides include neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) Mol. Ther. 12:659); an Fc fusion protein comprising a soluble Flt polypeptide (see, e.g., Pechan et al. (2009) Gene Ther. 16:10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-Xl); and the like. Suitable polypeptides include, but are not limited to, glial derived neurotrophic factor (GDNF); fibroblast growth factor 2; neurturin (NTN); ciliary neurotrophic factor (CNTF); nerve growth factor (NGF); neurotrophin-4 (NT4); brain derived neurotrophic factor (BDNF; e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 11 (SEQ ID NO:11)); epidermal growth factor; rhodopsin; X-linked inhibitor of apoptosis; and Sonic hedgehog.

Suitable light-responsive opsins include, e.g., a light-responsive opsin as described in U.S. Patent Publication No. 2007/0261127 (e.g., ChR2; Chop2); U.S. Patent Publication No. 2001/0086421; U.S. Patent Publication No. 2010/0015095; and Diester et al. (2011) Nat. Neurosci. 14:387.

Suitable polypeptides also include retinoschisin (e.g., a polypeptide comprising an amino acid sequence having at least about 90%, at least about 95%, at least about 98%, at least about 99%, or 100%, amino acid sequence identity to a contiguous stretch of from about 200 amino acids to 224 amino acids of the amino acid sequence depicted in FIG. 10 (SEQ ID NO:10). Suitable polypeptides include, e.g., retinitis pigmentosa GTPase regulator (RGPR)-interacting protein-1 (see, e.g., GenBank Accession Nos. Q96KN7, Q9EPQ2, and Q9GLM3) (e.g., a polypeptide comprising an amino acid sequence having at least about 90%, at least about 95%, at least about 98%, at least about 99%, or 100%, amino acid sequence identity to a contiguous stretch of from about 1150 amino acids to about 1200 amino acids, or from about 1200 amino acids to 1286 amino acids, of the amino acid sequence depicted in FIG. 16 (SEQ ID NO:21); peripherin-2 (Prph2) (see, e.g., GenBank Accession No. NP_000313 (e.g., a polypeptide comprising an amino acid sequence having at least about 90%, at least about 95%, at least about 98%, at least about 99%, or 100%, amino acid sequence identity to a contiguous stretch of from about 300 amino acids to 346 amino acids of the amino acid sequence depicted in FIG. 14 (SEQ ID NO:19); and Travis et al. (1991) Genomics 10:733); peripherin (e.g., a polypeptide comprising an amino acid sequence having at least about 90%, at least about 95%, at least about 98%, at least about 99%, or 100%, amino acid sequence identity to a contiguous stretch of from about 400 amino acids to about 470 amino acids of the amino acid sequence depicted in FIG. 15 (SEQ ID NO:20); a retinal pigment epithelium-specific protein (RPE65), (e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 12 (SEQ ID NO:12)) (see, e.g., GenBank AAC39660; and Morimura et al. (1998) Proc. Natl. Acad. Sci. USA 95:3088); and the like.

Suitable polypeptides also include: CHM (choroidermia (Rab escort protein 1)), a polypeptide that, when defective or missing, causes choroideremia (see, e.g., Donnelly et al. (1994) Hum. Mol. Genet. 3:1017; and van Bokhoven et al. (1994) Hum. Mol. Genet. 3:1041); and Crumbs homolog 1 (CRB1), a polypeptide that, when defective or missing, causes Leber congenital amaurosis and retinitis pigmentosa (see, e.g., den Hollander et al. (1999) Nat. Genet. 23:217; and GenBank Accession No. CAM23328).

Suitable polypeptides also include polypeptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) Ophthalmology 118:160-167); cone photoreceptor cGMP-gated cation channel beta-subunit (CNGB3) (see, e.g., Kohl et al. (2005) Eur J Hum Genet. 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) Nature 461(7265):784-787.

Site-Specific Endonucleases

In some cases, a gene product of interest is a site-specific endonuclease that provide for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease can be targeted to the defective allele and knock out the defective allele.

In addition to knocking out a defective allele, a site-specific nuclease can also be used to stimulate homologous recombination with a donor DNA that encodes a functional copy of the protein encoded by the defective allele. Thus, e.g., a subject rAAV virion can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) Nature 475:217. In some embodiments, a subject rAAV virion comprises a heterologous nucleotide sequence that encodes a site-specific endonuclease; and a heterologous nucleotide sequence that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, and the like.

Site-specific endonucleases that are suitable for use include, e.g., zinc finger nucleases (ZFNs); and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

Regulatory Sequences

In some embodiments, a nucleotide sequence encoding a gene product of interest is operably linked to a constitutive promoter. In other embodiments, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225).

Pharmaceutical Compositions

The present disclosure provides a pharmaceutical composition comprising: a) a subject rAAV virion, as described above; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Methods of Delivering a Gene Product to a Retinal Cell and Treatment Methods

The present disclosure provides a method of delivering a gene product to a retinal cell in an individual, the method comprising administering to the individual a subject rAAV virion as described above. The gene product can be a polypeptide or an interfering RNA (e.g., an shRNA, an siRNA, and the like), an aptamer, or a site-specific endonuclease, as described above. Delivering a gene product to a retinal cell can provide for treatment of a retinal disease. The retinal cell can be a photoreceptor, a retinal ganglion cell, a Müller cell, a bipolar cell, an amacrine cell, a horizontal cell, or a retinal pigmented epithelial cell. In some cases, the retinal cell is a photoreceptor cell, e.g., a rod or cone cell.

The present disclosure provides a method of treating a retinal disease, the method comprising administering to an individual in need thereof an effective amount of a subject rAAV virion as described above. A subject rAAV virion can be administered via intraocular injection, by intravitreal injection, or by any other convenient mode or route of administration. Other convenient modes or routes of administration include, e.g., intravenous, intranasal, etc.

A "therapeutically effective amount" will fall in a relatively broad range that can be determined through experimentation and/or clinical trials. For example, for in vivo injection, i.e., injection directly into the eye, a therapeutically effective dose will be on the order of from about $10^6$ to about $10^{15}$ of the rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

In some embodiments, more than one administration (e.g., two, three, four or more administrations) may be employed to achieve the desired level of gene expression over a period of various intervals, e.g., daily, weekly, monthly, yearly, etc.

Ocular diseases that can be treated using a subject method include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

Nucleic Acids and Host Cells

The present disclosure provides an isolated nucleic acid comprising a nucleotide sequence that encodes a subject variant adeno-associated virus (AAV) capsid protein as described above, where the variant AAV capsid protein comprises an insertion of from about 5 amino acids to about 11 amino acids in the GH loop or loop IV relative to a corresponding parental AAV capsid protein, and where the variant capsid protein, when present in an AAV virion, provides for increased infectivity of a retinal cell compared to the infectivity of the retinal cell by an AAV virion comprising the corresponding parental AAV capsid protein. A subject isolated nucleic acid can be an AAV vector, e.g., a recombinant AAV vector.

Insertion Peptides

A variant AAV capsid protein encoded by a subject nucleic acid has an insertion peptide of from about 5 amino acids to about 11 amino acids in length is inserted into the GH loop of an AAV capsid. The insertion peptide has a length of 5 amino acids, 6 amino acids, 7 amino acids, 8 amino acids, 9 amino acids, 10 amino acids, or 11 amino acids.

The insertion peptide can comprise an amino acid sequence of any one of the formulas set forth below.

For example, an insertion peptide can be a peptide of from 5 to 11 amino acids in length, where the insertion peptide is of Formula I:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is selected from Leu, Asn, and Lys;
$X_2$ is selected from Gly, Glu, Ala, and Asp;
$X_3$ is selected from Glu, Thr, Gly, and Pro;
$X_4$ is selected from Thr, Ile, Gln, and Lys;
$X_5$ is selected from Thr and Ala;
$X_6$ is selected from Arg, Asn, and Thr;
$X_7$, if present, is selected from Pro and Asn.

As another example, an insertion peptide can be a peptide of from 5 to 11 amino acids in length, where the insertion peptide is of Formula IIa:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
each of $X_1$-$X_4$ is any amino acid;
$X_5$ is Thr;
$X_6$ is Arg; and
$X_7$ is Pro.

As another example, an insertion peptide can be a peptide of from 5 to 11 amino acids in length, where the insertion peptide is of Formula IIb:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is selected from Leu and Asn;
$X_2$, if present, is selected from Gly and Glu;
$X_3$ is selected from Glu and Thr;
$X_4$ is selected from Thr and Ile;
$X_5$ is Thr;
$X_6$ is Arg; and
$X_7$ is Pro.

As another example, an insertion peptide can be a peptide of from 5 to 11 amino acids in length, where the insertion peptide is of Formula III:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is Lys;
$X_2$ is selected from Ala and Asp;
$X_3$ is selected from Gly and Pro;
$X_4$ is selected from Gln and Lys;
$X_5$ is selected from Thr and Ala;
$X_6$ is selected from Asn and Thr;
$X_7$, if present, is Asn.

As another example, an insertion peptide can be a peptide of from 5 to 11 amino acids in length, where the insertion peptide is of Formula IV:

$$Y_1Y_2X_1X_2X_3X_4X_5X_6X_7Y_3Y_4$$

where:
each of $Y_1$-$Y_4$, if present, is independently selected from Ala, Leu, Gly, Ser, and Thr;
$X_1$, if present, is a positively charged amino acid or an uncharged amino acid; or is selected from Leu, Asn, Arg, Ala, Ser, and Lys;
$X_2$ is a negatively charged amino acid or an uncharged amino acid; or is selected from Gly, Glu, Ala, Val, Thr, and Asp;
$X_3$ is a negatively charged amino acid or an uncharged amino acid; or is selected from Glu, Thr, Gly, Asp, or Pro;
$X_4$ is selected from Thr, Ile, Gly, Lys, Asp, and Gln;
$X_5$ is a polar amino acid, an alcohol (an amino acid having a free hydroxyl group), or a hydrophobic amino acid; or is selected from Thr, Ser, Val, and Ala;
$X_6$ is a positively charged amino acid or an uncharged amino acid; or is selected from Arg, Val, Lys, Pro, Thr, and Asn; and
$X_7$, if present, is a positively charged amino acid or an uncharged amino acid; or is selected from Pro, Gly, Phe, Asn, and Arg.

As non-limiting examples, the insertion peptide can comprise an amino acid sequence selected from LGETTRP (SEQ ID NO:13), NETITRP (SEQ ID NO:14), KAGQANN (SEQ ID NO:15), KDPKTTN (SEQ ID NO:16), KDTDTTR (SEQ ID NO:57), RAGGSVG (SEQ ID NO:58), AVDTTKF (SEQ ID NO:59), and STGKVPN (SEQ ID NO:60).

In some cases, the insertion peptide has from 1 to 4 spacer amino acids ($Y_1$-$Y_4$) at the amino terminus and/or at the carboxyl terminus of any one of LGETTRP (SEQ ID NO:13), NETITRP (SEQ ID NO:14), KAGQANN (SEQ ID NO:15), KDPKTTN (SEQ ID NO:16), KDTDTTR (SEQ ID NO:57), RAGGSVG (SEQ ID NO:58), AVDTTKF (SEQ ID NO:59), and STGKVPN (SEQ ID NO:60). Suitable spacer amino acids include, but are not limited to, leucine, alanine, glycine, and serine.

For example, in some cases, an insertion peptide has one of the following amino acid sequences: LALGETTRPA (SEQ ID NO:45); LANETITRPA (SEQ ID NO:46), LAKAGQANNA (SEQ ID NO:47), LAKDPKTTNA (SEQ ID NO:48), LAKDTDTTRA (SEQ ID NO:61), LARAGGSVGA (SEQ ID NO:62), LAAVDTTKFA (SEQ ID NO:63), and LASTGKVPNA (SEQ ID NO:64). As another example, in some cases, an insertion peptide has one of the following amino acid sequences: AALGETTRPA (SEQ ID NO:49); AANETITRPA (SEQ ID NO:50), AAKAGQANNA (SEQ ID NO:51), and AAKDPKTTNA (SEQ ID NO:52). As yet another example, in some cases, an insertion peptide has one of the following amino acid sequences: GLGETTRPA (SEQ ID NO:53); GNETITRPA (SEQ ID NO:54), GKAGQANNA (SEQ ID NO:55), and GKDPKTTNA (SEQ ID NO:56). As another example, in some cases, an insertion peptide comprises one of KDTDTTR (SEQ ID NO:57), RAGGSVG (SEQ ID NO:58), AVDTTKF (SEQ ID NO:59), and STGKVPN (SEQ ID NO:60), flanked on the C-terminus by AA and on the N-terminus by A; or comprises one of KDTDTTR (SEQ ID NO:57), RAGGSVG (SEQ ID NO:58), AVDTTKF (SEQ ID NO:59), and STGKVPN (SEQ ID NO:60) flanked on the C-terminus by G and on the N-terminus by A.

A subject recombinant AAV vector can be used to generate a subject recombinant AAV virion, as described above. Thus, the present disclosure provides a recombinant AAV vector that, when introduced into a suitable cell, can provide for production of a subject recombinant AAV virion.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. A subject host cell can also be made using a baculovirus to infect insect cells such as Sf9 cells, which produce AAV (see, e.g., U.S. Pat. No. 7,271,002; U.S. patent application Ser. No. 12/297,958)

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

AAV Variant with Enhanced Transduction of Retinal Cells

The approach used was to create a peptide display library by introducing a unique AvrII site into the wild type AAV2 genome between amino acid 587 and 588 by polymerase chain reaction (PCR) mutagenesis. A random 21 nucleotide insert, 7mer For, was used to synthesize dsDNA inserts, along with the antisense primer 7mer Rev. The resulting dsDNA inserts were cloned into the AvrII site of the genome after digestion with NheI, producing a diverse 7mer display library which was then packaged (Perabo et al., 2003; Muller et al., 2003). The virus was generated such that each viral genome was packaged or encapsidated within the capsid protein variant that that genome encoded. In this respect, functional improvements identified through selection can be linked to the genome sequence encoding this improved function contained within the viral capsid.

This library was subjected to positive selection within rho-GFP mice (Wensel et al. (2005) *Vision Res.* 45:3445). Briefly, in one round of selection, adult rho-GFP mice were intravitreally injected with 2 µL of phosphate buffered saline (PBS)-dialyzed, iodixanol-purified library with a genomic titer of approximately $1\times10^{12}$ viral genomes (vg)/mL. An ultrafine 30½-gauge disposable needle was passed through the sclera of the animal's eye, at the equator and next to the limbus, into the vitreous cavity. Injection of 2 µl of virus was made with direct observation of the needle in the center of the vitreous cavity. One week post-injection, eyes were enucleated and retinas dissociated using a light, papain protease treatment, followed by fluorescence activated cell sorter (FACS) isolation of photoreceptor populations. Successful virions were then PCR amplified from subsequent genomic extractions and further cloned and repackaged for injection.

Further iterations of this selection were performed, narrowing the pool of variants to a subset with the most permissive mutations. After three iterations, a round of error-prone PCR was performed to create a further generation of variants for selection. In total, this process was repeated for two generations. In this respect, this process of directed evolution created photoreceptor-permissive AAV variants through the application of positive selection and induced mutagenesis, similar to the process of natural evolution.

Subsequently, the cap genes of fifty variants were sequenced to determine the most prominent and successful variants to have permissive mutations for intravitreal photoreceptor transduction. Of the 50 clones, 46 gave readable sequences of a 7mer insert. Remarkably, nearly two thirds of clones contained the same distinct 7mer motif (~$^{588}$LGETTRP~; SEQ ID NO:13). Interestingly, the next most prominent variant (~$^{588}$NETITRP~; SEQ ID NO:14) also contained a similar flanking motif consisting of a positively-charged arginine residue in between a polar threonine and a nonpolar proline residue (TRP).

TABLE 1

| Clone | Appr. Frequency (%) | Frequency |
|---|---|---|
| ~$^{588}$LGETTRP~ (SEQ ID NO: 13) | 64 | 31 |
| ~$^{588}$NETITRP~ (SEQ ID NO: 14) | 12 | 5 |
| ~$^{588}$KAGQANN~ (SEQ ID NO: 15) | 6 | 3 |
| ~$^{588}$KDPKTTN~ (SEQ ID NO: 16) | 4 | 2 |
| ~$^{588}$KDTDTTR (SEQ ID NO: 57) | | 2 |
| ~$^{588}$RAGGSVG (SEQ ID NO: 58) | | 1 |
| ~$^{588}$AVDTTKF (SEQ ID NO: 59) | | 1 |
| ~$^{588}$STGKVPN (SEQ ID NO: 60) | | 1 |

Table 1 Sequencing of isolated variants from directed evolution reveals a high degree of convergence in viral libraries. All variants derived from the AAV2 7mer library, with approximately 64% of variants containing the same 7mer motif (~$^{588}$LGETTRP~ (SEQ ID NO:13)).

Among the 7mer insert sequences, there were moderate preferences at particular positions, e.g., a positively charged amino acid at position 1; a negatively charged amino acid at position 2; an alcohol (e.g., an amino acid having an alcohol group (a free hydroxyl group), such as Thr or Ser) at position 5.

The 7mer inserts were flanked by spacers, as shown in Table 2:

| Clone | | Frequency |
|---|---|---|
| ~588LALGETTRPA~ | (SEQ ID NO: 45) | 31 |
| ~588LANETITRPA~ | (SEQ ID NO: 46) | 5 |
| ~588LAKAGQANNA~ | (SEQ ID NO: 47) | 3 |
| ~588LAKDPKTTNA~ | (SEQ ID NO: 48) | 2 |
| ~588LAKDTDTTRA~ | (SEQ ID NO: 61) | 2 |
| ~588LARAGGSVGA~ | (SEQ ID NO: 62) | 1 |
| ~588LAAVDTTKFA~ | (SEQ ID NO: 63) | 1 |
| ~588LASTGKVPNA~ | (SEQ ID NO: 64) | 1 |

FIG. 1. Representative three-dimensional capsid model of AAV2 containing a random heptamer (shown in orange) following amino acid 587. This area of the AAV2 capsid likely participates in cell-surface receptor binding.

In light of the high degree of library convergence from the above-described selection, a recombinant form of AAV2 ~588LGETTRP~ (SEQ ID NO:13; nick named 7M8) was cloned and packaged the vector with a scCAG-GFP transgene to visualize its transduction profile. Three weeks following intravitreal injection in adult mice, robust expression in numerous cell types, including retinal ganglion cells (RGCs) and Müller cells, was observed. Importantly, transduction of photoreceptors in retinas injected with 7M8, as seen by GFP expression in outer nuclear layer (ONL) nuclei (red arrows) and in outer segments (FIG. 2, blue arrow), was observed, whereas AAV2 showed no discernable photoreceptor expression.

FIG. 2 AAV2 7M8 variant (right) demonstrates greater levels of intravitreal photoreceptor transduction relative to AAV2 (left). Confocal microscopy of transverse retinal sections three weeks after intravitreal injection of 2 μL of $1\times10^{12}$ vg/mL of AAV2 7M8 and AAV2 scCAG GFP in adult mice. Red arrows (top) denote photoreceptor nuclei and blue arrow (top) denote photoreceptor outer segments.

Figure 3:
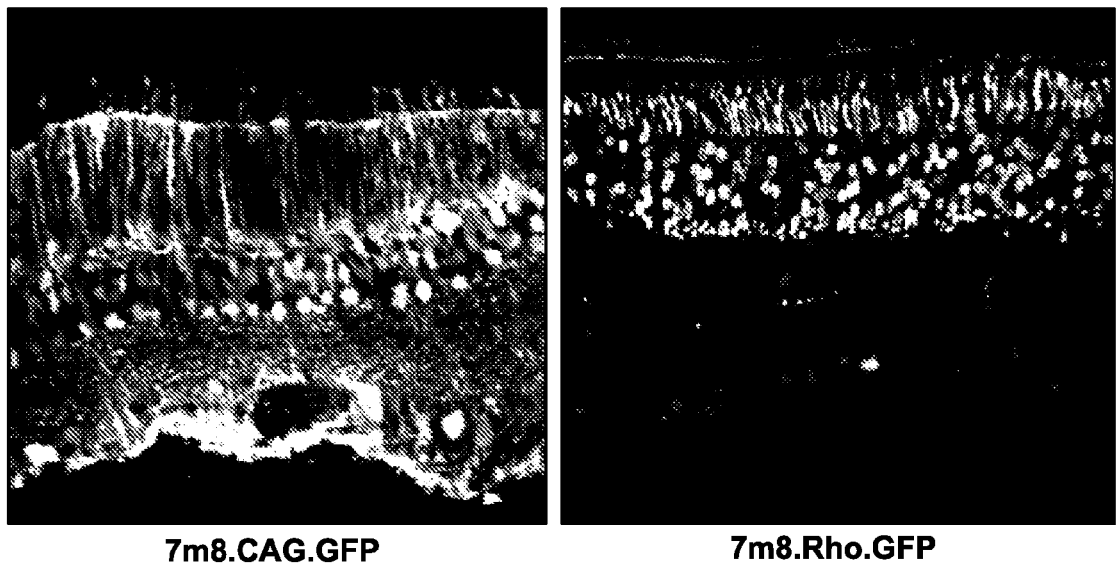
FIG. 3 provides representative fluorescence images of retinal cryoslices showing green fluorescent protein (GFP) expression resulting from 7M8 carrying the GFP gene under the control of the ubiquitous CAG promoter (left) or a photoreceptor-specific Rho promoter (right).

In light of these gains in retinal cell transduction, an attempt was made to increase specificity in expression through the use of a ssRho-eGFP transgene containing a photoreceptor-specific rhodopsin promoter to better resolve transduction efficiencies specifically in photoreceptors (FIG. 3). Indeed the use of a photoreceptor specific Rho promoter limited the GFP expression to the photoreceptors. An attempt was made to improve 7M8 transduction efficiency by combining a rational design approach to the previous directed evolution approach. Therefore, four surface exposed tyrosine residues were mutagenized to phenylalanines on the 7M8 capsid (Y273F, Y444F, Y500F, and Y730F) which has previous been shown to increase photoreceptor infectivity (Petrs-Silva et al., 2009). Interestingly, the addition of mutations decreased number of photoreceptors transduced compared to the original virus as show by FACs sorting of the GFP(+) photoreceptors from 7m8 or 7m8-4YF infected retinas (FIG. 4).

FIG. 3. Representative fluorescence images of retinal cryoslices showing GFP expression resulting from 7m8 carrying the GFP gene under the control of the ubiquitous CAG promoter (left) or a photoreceptor specific Rho promoter (right).

Figure 4:
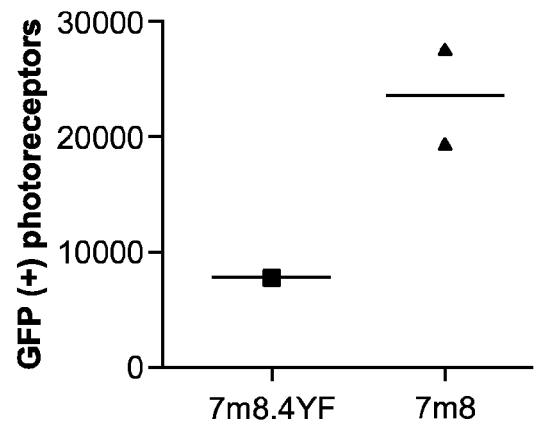
FIG. 4 depicts GFP photoreceptor cells per million retinal cells as counted by flow cytometry, following transduction by 7M8 or by 7M8 bearing 4 tyrosine mutations (7m8.4YF).
Figure 7:
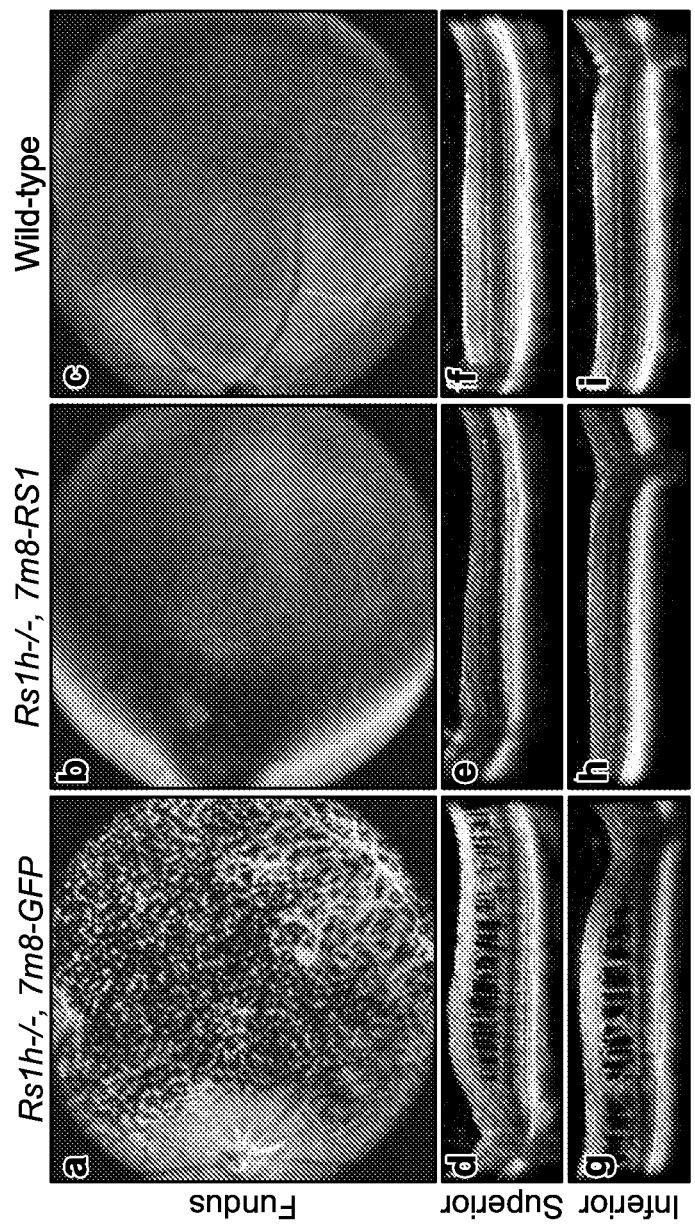
FIGS. 7A-I depict structural improvements in the Rs1h−/− mouse retina after gene transfer.

FIG. 4. GFP(+) photoreceptor cells per million retinal cells as counted by flow cytometry. 7m8 transduces more than 2× the amount of photoreceptors compared 7m8 bearing 4 tyrosine mutations (top).

Example 2

Treatment of Retinoschisis

Using the expression construct 7m8-rho-RS1, a functional retinoschisin (RS1) protein was delivered to retinoschisin-deficient mice (Rs1h-deficient mice; Rs1h is the mouse homolog of human RS1). The vector comprises a nucleotide sequence encoding a functional retinoschisin protein under transcriptional control of a rhodopsin promoter. See FIGS. 13A-C, where the bold and underlined nucleotide sequence (nucleotides 4013-4851) are the rhodopsin promoter; and nucleotides 4866-5540 (with the start atg and stop tga sequences shown in bold) encode a human RS1 protein.

The 7m8-rho-RS1 construct was administered intravitreally to Rs1h–/– mice at P15. Rs1h–/– mice were generated through targeted disruption of exon 3 of the Rs1h gene, as described (Weber et al. (2002) Proc. Natl. Acad. Sci. USA 99:6222). The Rs1h–/– mice are deficient in the Rs1h protein product, have an electronegative ERG (e.g., a reduced b-wave with relative preservation of the a-wave) and splitting of the layers of the retina, similar to what is seen in human retinoschisis patients. Injection of the 7m8-rho-RS1 vector into the Rs1h–/– led to high levels of panretinal RS1 expression from photoreceptors in the retina. RS1 expression led to improved retinal morphology with a decrease in the number and size of cavities in the retina as seen in spectral-domain optical coherence tomography (SD-OCT) imaging (FIGS. 7A-I), a rescue of the ERG b-wave (FIGS. 8A-D), and long-term structural preservation of the retina (FIGS. 9A-E).

FIGS. 7A-I. Representative high-resolution SD-OCT images of retinas injected with 7m8-rho-GFP (left column), 7m8-rho-RS1 (middle column), or uninjected WT animals (right column). Fundus images were taken through the inner nuclear layer of the superior retina and exclude other layers (a-c). Transverse images of the superior (d-f) and inferior (g-i) retina were taken using the optic nerve head as a landmark.

The untreated RS1 retina increases in overall thickness when measured from the inner limiting membrane (ILM) to the photoreceptors, as the pathology progresses due to the schisis splitting the inner retina. This process is distinct from that observed in most retinal degenerative diseases (RDD) which do not form schisis, but exhibit progressive photoreceptor cell death in the INL and concomitant retinal thinning and loss of ERG amplitude. In RS1, the ONL thins as photoreceptors die from the disease, but this is distinct from the overall retinal thickness change. It is generally thought that a successful therapy for RS1 would return the overall retinal thickness to the wildtype and ameliorate the photoreceptor loss in the ONL. In most RDD other than Rs1, the loss of photoreceptors, marked by ONL thinning, is paralleled by a decrease in retinal physiological output as measured by the ERG amplitude. RS1 is one of the very few examples of a retinal disease in which the pathology increases the retinal thickness with concomitant erg amplitude loss. In summary, restoring the RS1 gene product, an extracellular retinal "glue;—thins the retina back to the wildtype thickness and the erg amplitude returns to near normal levels as the schisis resolves.

Figure 8:
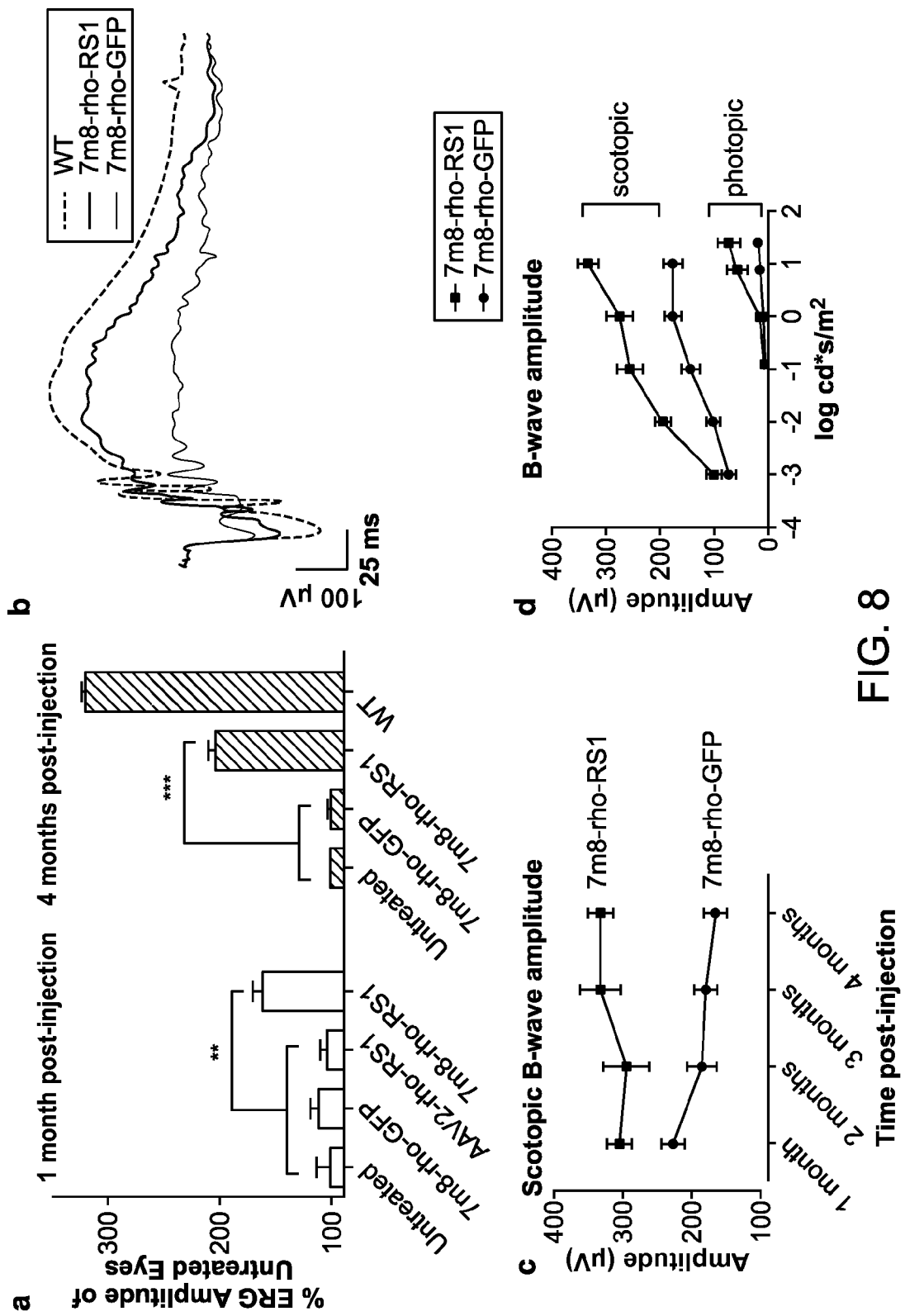
FIGS. 8A-D depict functional rescue of the electroretinogram A and B waves following RS1 gene delivery.
Figure 19:
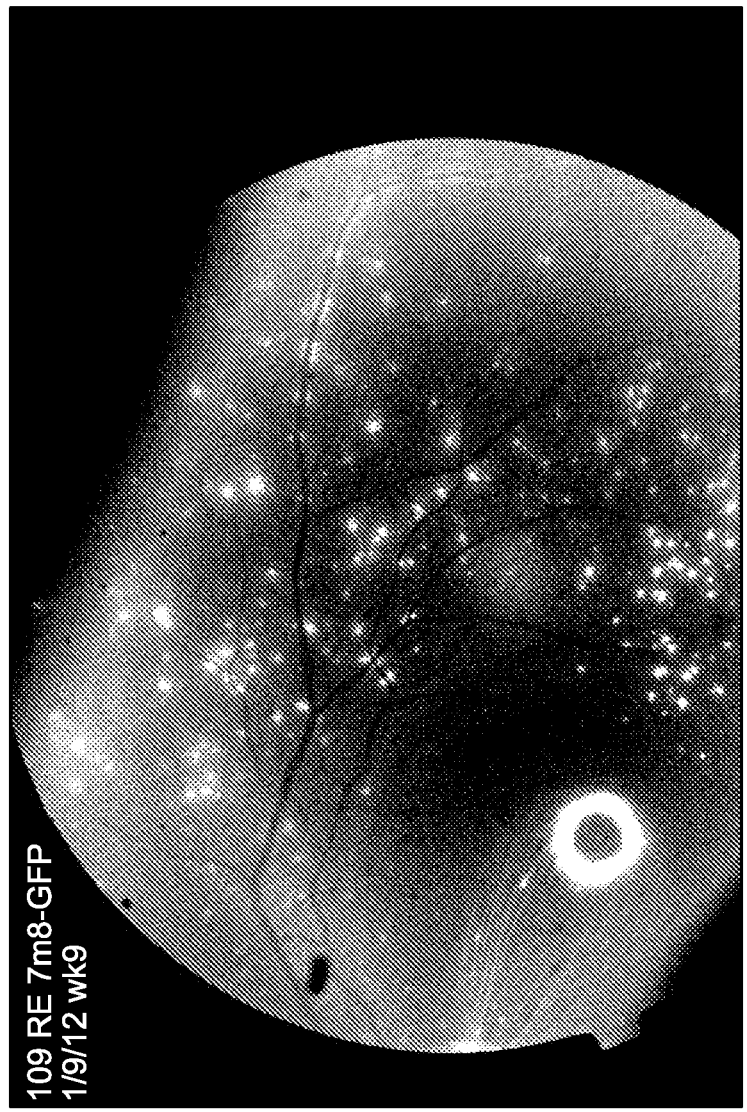
FIG. 19 provides a fluorescence fundus image showing GFP expression in central primate retina 9 weeks after administration of 7m8 carrying GFP under the control of a connexin36 promoter.

FIG. 8a shows a comparison of functional rescue of untreated Rs1–/– eyes to AAV2-rho-RS1, 7m8-rho-GFP, and 7m8-rho-RS1 injected eyes both one month (left) and 4 months (right) after injection. One month post-injection, 7m8-rho-RS1 led to considerable rescue of the ERG b-wave amplitude, whereas AAV2-rho.RS1 was statistically indistinguishable from untreated eyes.

After 4 months, the 7m8-rho-RS1 amplitude further increases toward the wild-type amplitude (right). FIG. 8b shows representative ERG traces from 7m8-rho-RS1-injected eyes show improved amplitude of the a-wave and b-wave and a waveform closer to wild-type eyes, compared to 7m8-rho-GFP-injected eyes. FIG. 8c shows the amplitude of the full-field scotopic b-wave resulting from a high intensity (1 log cdxs/m2) stimulus was recorded on a monthly basis beginning one month after injection at P15 for each condition. Three responses were recorded and averaged for each eye at each time point.

Mean ERG b-wave amplitudes were plotted as a function of time post-injection. n=7 was used for both conditions. FIG. 8d shows an analysis of ERG responses under scotopic (upper traces, stimulus range from −3 to 1 log cdxs/m2) and photopic (lower traces, range from −0.9 to 1.4 log cdxs/m2) conditions indicates improved rod and cone function over a range of stimuli intensities.

FIGS. 9A-E. Sustained improvements in retinal thickness measured at 10 months post 7m8-rho-RS1 treatment. Representative transverse SD-OCT images of a) 7m8-rho-RS1 or b) or 7m8-rho-GFP treated retinas 10 months post-injection centered on the optic nerve head. Measurements of c) retinal thickness, d) ONL thickness, and e) and inner and outer segment thickness are plotted as a function of distance from the optic nerve head.

Example 3

AAV Variant Used to Deliver a Protein to Retinal Cells in the Macaque

A recombinant AAV2 virion (7m8 carrying GFP under the control of a connexin36 promoter) was generated. The recombinant AAV2 virion included an AAV2 capsid variant with an insertion of LALGETTRPA peptide between amino acids 587 and 588 of AAV2 capsid, and GFP under transcriptional control of a connexin36 promoter, which is expressed in interneurons. The rAAV2 virion was injected intravitreally into the eye of a macaque. The data are shown in FIG. 18.

FIG. 18 provides a fluorescence fundus image showing GFP expression at the back of the retina 9 weeks after administration of 7m8 carrying GFP under the control of a connexin36 promoter. Compared to the parental AAV2 serotype (Yin et al, IOVS 52(5); 2775), a higher level of expression was seen in the foveal ring, and visible fluorescence was seen in the central retina outside the fovea.

REFERENCES

Daiger S P, Bowne S J, Sullivan L S (2007) Perspective on genes and mutations causing retinitis pigmentosa. Arch Ophthalmol 125: 151-158.

Dalkara D, Kolstad K D, Caporale N, Visel M, Klimczak R R, et al. (2009) Inner Limiting Membrane Barriers to AAV Mediated Retinal Transduction from the Vitreous. Mol Ther.

den Hollander A I, Roepman R, Koenekoop R K, Cremers F P (2008) Leber congenital amaurosis: genes, proteins and disease mechanisms. Prog Retin Eye Res 27: 391-419.

Gruter O, Kostic C, Crippa S V, Perez M T, Zografos L, et al. (2005) Lentiviral vector-mediated gene transfer in adult mouse photoreceptors is impaired by the presence of a physical barrier. Gene Ther 12: 942-947.

Maguire A M, Simonelli F, Pierce E A, Pugh E N, Jr., Mingozzi F, et al. (2008) Safety and efficacy of gene transfer for Leber's congenital amaurosis. N Engl J Med 358: 2240-2248.

Mancuso K, Hauswirth W W, Li Q, Connor T B, Kuchenbecker J A, et al. (2009) Gene therapy for red-green colour blindness in adult primates. Nature 461: 784-787.

McGee Sanftner L H, Abel H, Hauswirth W W, Flannery J G (2001) Glial cell line derived neurotrophic factor delays photoreceptor degeneration in a transgenic rat model of retinitis pigmentosa. Mol Ther 4: 622-629.

Muller O J, Kaul F, Weitzman M D, Pasqualini R, Arap W, et al. (2003) Random peptide libraries displayed on adeno-associated virus to select for targeted gene therapy vectors. Nat Biotechnol 21: 1040-1046.

Nakazawa T. et al. (2007) Attenuated glial reactions and photoreceptor degeneration after retinal detachment in mice deficient in glial fibrillary acidic protein and vimentin. Invest Ophthamol Vis Sci 48: 2760-8.

Nakazawa T. et al. (2006) Characterization of cytokine responses to retinal detachment in rats. Mol Vis 12: 867-78.

Perabo L, Buning H, Kofler D M, Ried M U, Girod A, et al. (2003) In vitro selection of viral vectors with modified tropism: the adeno-associated virus display. Mol Ther 8: 151-157.

Petrs-Silva H, Dinculescu A, Li Q, Min S H, Chiodo V, et al. (2009) High-efficiency transduction of the mouse retina by tyrosine-mutant AAV serotype vectors. Mol Ther 17: 463-471.

Reme C E, Grimm C, Hafezi F, Wenzel A, Williams T P (2000) Apoptosis in the Retina: The Silent Death of Vision. News Physiol Sci 15: 120-124.

Rolling F (2004) Recombinant AAV-mediated gene transfer to the retina: gene therapy perspectives. Gene Ther 11 Suppl 1: S26-32.

Wensel T G, Gross A K, Chan F, Sykoudis K, Wilson J H (2005) Rhodopsin-EGFP knock-ins for imaging quantal gene alterations. Vision Res 45: 3445-3453.

Zhong L, Li B, Mah C S, Govindasamy L, Agbandje-McKenna M, et al. (2008) Next generation of adeno-associated virus 2 vectors: point mutations in tyrosines lead to high-efficiency transduction at lower doses. Proc Natl Acad Sci USA 105: 7827-7832.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

<160> NUMBER OF SEQ ID NOS: 64

<210> SEQ ID NO 1
<211> LENGTH: 733
<212> TYPE: PRT
<213> ORGANISM: Adeno-associated virus-2

<400> SEQUENCE: 1

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415
```

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg
                725                 730

<210> SEQ ID NO 2
<211> LENGTH: 42
<212> TYPE: PRT
<213> ORGANISM: Adeno-associated virus-2

<400> SEQUENCE: 2

Pro Val Ala Thr Glu Gln Tyr Gly Ser Val Ser Thr Asn Leu Gln Arg
1               5                   10                  15

Gly Asn Arg Gln Ala Ala Thr Ala Asp Val Asn Thr Gln Gly Val Leu
            20                  25                  30

Pro Gly Met Val Trp Gln Asp Arg Asp Val
        35                  40

```
<210> SEQ ID NO 3
<211> LENGTH: 42
<212> TYPE: PRT
<213> ORGANISM: Adeno-associated virus-AAV-1

<400> SEQUENCE: 3

Pro Val Ala Thr Glu Arg Phe Gly Thr Val Ala Val Asn Phe Gln Ser
1               5                   10                  15

Ser Ser Thr Asp Pro Ala Thr Gly Asp Val His Ala Met Gly Ala Leu
            20                  25                  30

Pro Gly Met Val Trp Gln Asp Arg Asp Val
        35                  40

<210> SEQ ID NO 4
<211> LENGTH: 42
<212> TYPE: PRT
<213> ORGANISM: Adeno-associated virus-5

<400> SEQUENCE: 4

Arg Val Ala Tyr Asn Val Gly Gly Gln Met Ala Thr Asn Asn Gln Ser
1               5                   10                  15

Ser Thr Thr Ala Pro Ala Thr Gly Thr Tyr Asn Leu Gln Glu Ile Val
            20                  25                  30

Pro Gly Ser Val Trp Met Glu Arg Asp Val
        35                  40

<210> SEQ ID NO 5
<211> LENGTH: 42
<212> TYPE: PRT
<213> ORGANISM: Adeno-associated virus-AAV-6

<400> SEQUENCE: 5

Pro Val Ala Thr Glu Arg Phe Gly Thr Val Ala Val Asn Leu Gln Ser
1               5                   10                  15

Ser Ser Thr Asp Pro Ala Thr Gly Asp Val His Val Met Gly Ala Leu
            20                  25                  30

Pro Gly Met Val Trp Gln Asp Arg Asp Val
        35                  40

<210> SEQ ID NO 6
<211> LENGTH: 42
<212> TYPE: PRT
<213> ORGANISM: Adeno-associated virus-AAV-

<400> SEQUENCE: 6

Pro Val Ala Thr Glu Glu Tyr Gly Ile Val Ser Ser Asn Leu Gln Ala
1               5                   10                  15

Ala Asn Thr Ala Ala Gln Thr Gln Val Val Asn Asn Gln Gly Ala Leu
            20                  25                  30

Pro Gly Met Val Trp Gln Asn Arg Asp Val
        35                  40

<210> SEQ ID NO 7
<211> LENGTH: 42
<212> TYPE: PRT
<213> ORGANISM: Adeno-associated virus-AAV-8

<400> SEQUENCE: 7

Pro Val Ala Thr Glu Glu Tyr Gly Ile Val Ala Asp Asn Leu Gln Gln
1               5                   10                  15

Gln Asn Thr Ala Pro Gln Ile Gly Thr Val Asn Ser Gln Gly Ala Leu
```

```
                 20                  25                  30

Pro Gly Met Val Trp Gln Asn Arg Asp Val
        35                  40

<210> SEQ ID NO 8
<211> LENGTH: 42
<212> TYPE: PRT
<213> ORGANISM: Adeno-associated virus-AAV-9

<400> SEQUENCE: 8

Pro Val Ala Thr Glu Ser Tyr Gly Gln Val Ala Thr Asn His Gln Ser
1               5                   10                  15

Ala Gln Ala Gln Ala Gln Thr Gly Trp Val Gln Asn Gln Gly Ile Leu
            20                  25                  30

Pro Gly Met Val Trp Gln Asp Arg Asp Val
        35                  40

<210> SEQ ID NO 9
<211> LENGTH: 42
<212> TYPE: PRT
<213> ORGANISM: Adeno-associated virus-AAV-10

<400> SEQUENCE: 9

Pro Val Ala Thr Glu Gln Tyr Gly Val Val Ala Asp Asn Leu Gln Gln
1               5                   10                  15

Ala Asn Thr Gly Pro Ile Val Gly Asn Val Asn Ser Gln Gly Ala Leu
            20                  25                  30

Pro Gly Met Val Trp Gln Asn Arg Asp Val
        35                  40

<210> SEQ ID NO 10
<211> LENGTH: 224
<212> TYPE: PRT
<213> ORGANISM: Homo sapiens

<400> SEQUENCE: 10

Met Ser Arg Lys Ile Glu Gly Phe Leu Leu Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr Gln Lys Ala Cys Lys Cys Asp Cys Gln Gly Gly Pro Asn Ala
        35                  40                  45

Leu Trp Ser Ala Gly Ala Thr Ser Leu Asp Cys Ile Pro Glu Cys Pro
    50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175
```

```
Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
    210                 215                 220

<210> SEQ ID NO 11
<211> LENGTH: 247
<212> TYPE: PRT
<213> ORGANISM: Homo sapiens

<400> SEQUENCE: 11

Met Thr Ile Leu Phe Leu Thr Met Val Ile Ser Tyr Phe Gly Cys Met
1               5                  10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Met Val Leu Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 12
<211> LENGTH: 533
<212> TYPE: PRT
<213> ORGANISM: Homo sapiens

<400> SEQUENCE: 12

Met Ser Ile Gln Val Glu His Pro Ala Gly Gly Tyr Lys Lys Leu Phe
1               5                  10                  15

Glu Thr Val Glu Glu Leu Ser Ser Pro Leu Thr Ala His Val Thr Gly
            20                  25                  30
```

```
Arg Ile Pro Leu Trp Leu Thr Gly Ser Leu Arg Cys Gly Pro Gly
            35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Ser Tyr Phe Arg Gly Val Glu Val
            115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
            195                 200                 205

Ile Pro Pro Leu Gln Ala Asp Lys Glu Asp Pro Ile Ser Lys Ser Glu
            210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
            275                 280                 285

Leu His Ile Ala Asp Lys Arg Lys Lys Tyr Leu Asn Asn Lys Tyr
            290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
            355                 360                 365

Val Leu Pro Leu Asn Ile Asp Lys Ala Asp Thr Gly Lys Asn Leu Val
    370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
            435                 440                 445
```

-continued

```
Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
                515                 520                 525

Leu Phe Lys Lys Ser
    530
```

```
<210> SEQ ID NO 13
<211> LENGTH: 7
<212> TYPE: PRT
<213> ORGANISM: Artificial sequence
<220> FEATURE:
<223> OTHER INFORMATION: Synthetic peptide

<400> SEQUENCE: 13

Leu Gly Glu Thr Thr Arg Pro
1               5
```

```
<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Asn Glu Thr Ile Thr Arg Pro
1               5
```

```
<210> SEQ ID NO 15
<211> LENGTH: 7
<212> TYPE: PRT
<213> ORGANISM: Artificial sequence
<220> FEATURE:
<223> OTHER INFORMATION: Synthetic peptide

<400> SEQUENCE: 15

Lys Ala Gly Gln Ala Asn Asn
1               5
```

```
<210> SEQ ID NO 16
<211> LENGTH: 7
<212> TYPE: PRT
<213> ORGANISM: Artificial sequence
<220> FEATURE:
<223> OTHER INFORMATION: Synthetic peptide

<400> SEQUENCE: 16

Lys Asp Pro Lys Thr Thr Asn
1               5
```

```
<210> SEQ ID NO 17
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 17
```

```
cgcaaucagu gaaugcuuau acauccg                                        27
```

<210> SEQ ID NO 18
<211> LENGTH: 5541
<212> TYPE: DNA
<213> ORGANISM: Artificial sequence
<220> FEATURE:
<223> OTHER INFORMATION: Synthetic construct

<400> SEQUENCE: 18

```
agcttggatc caatcaacct ctggattaca aaatttgtga agattgact ggtattctta      60
actatgttgc tccttttacg ctatgtggat acgctgcttt aatgcctttg tatcatgcta    120
ttgcttcccg tatggctttc attttctcct ccttgtataa atcctggttg ctgtctcttt    180
atgaggagtt gtggcccgtt gtcaggcaac gtggcgtggt gtgcactgtg tttgctgacg    240
caaccccac tggttggggc attgccacca cctgtcagct cctttccggg actttcgctt    300
tcccccctccc tattgccacg gcggaactca tcgccgcctg ccttgcccgc tgctggacag    360
gggctcggct gttgggcact gacaattccg tggtgttgtc ggggaagctg acgtccttc    420
catggctgct cgcctgtgtt gccacctgga ttctgcgcgg gacgtccttc tgctacgtcc    480
cttcggccct caatccagcg gaccttcctt cccgcggcct gctgccggct ctgcggcctc    540
ttccgcgtct tcgagatctg cctcgactgt gccttctagt tgccagccat ctgttgtttg    600
ccctcccc gtgccttcct tgaccctgga aggtgccact cccactgtcc tttcctaata    660
aaatgaggaa attgcatcgc attgtctgag taggtgtcat tctattctgg ggggtggggt    720
ggggcaggac agcaagggggg aggattggga agacaatagc aggcatgctg gggactcgag    780
ttaagggcga attcccgatt aggatcttcc tagagcatgg ctacgtagat aagtagcatg    840
gcgggttaat cattaactac aaggaacccc tagtgatgga gttggccact ccctctctgc    900
gcgctcgctc gctcactgag gccgggcgac caaaggtcgc ccgacgcccg gctttgccc    960
gggcggcctc agtgagcgag cgagcgcgca gccttaatta acctaattca ctggccgtcg   1020
ttttacaacg tcgtgactgg gaaaaccctg gcgttaccca acttaatcgc cttgcagcac   1080
atccccctt cgccagctgg cgtaatagcg aagaggcccg caccgatcgc ccttcccaac   1140
agttgcgcag cctgaatggc gaatgggacg cgccctgtag cggcgcatta agcgcggcgg   1200
gtgtggtggt tacgcgcagc gtgaccgcta cacttgccag cgccctagcg cccgctcctt   1260
tcgctttctt cccttccttt ctcgccacgt tcgccggctt tccccgtcaa gctctaaatc   1320
gggggctccc tttagggttc cgatttagtg ctttacggca cctcgacccc aaaaaacttg   1380
attagggtga tggttcacgt agtgggccat cgccccgata cggtttt cgccctttga     1440
cgctggagtt cacgttcctc aatagtggac tcttgttcca aactggaaca acactcaacc    1500
ctatctcggt ctattctttt gatttataag ggattttcc gatttcggcc tattggttaa    1560
aaaatgagct gatttaacaa aaatttaacg cgaattttaa caaaatatta cgtttataa    1620
tttcaggtgg catctttcgg ggaaatgtgc gcggaacccc tatttgttta ttttctaaa    1680
tacattcaaa tatgtatccg ctcatgagac aataaccctg ataaatgctt caataatatt    1740
gaaaaggaa gagtatgagt attcaacatt tccgtgtcgc ccttattccc ttttttgcgg    1800
cattttgcct tcctgttttt gctcacccag aaacgctggt gaaagtaaaa gatgctgaag    1860
atcagttggg tgcacgagtg ggttacatcg aactggatct caatagtggt aagatccttg    1920
agagttttcg ccccgaagaa cgttttccaa tgatgagcac ttttaaagtt ctgctatgtg    1980
```

```
gcgcggtatt atcccgtatt gacgccgggc aagagcaact cggtcgccgc atacactatt    2040
ctcagaatga cttggttgag tactcaccag tcacagaaaa gcatcttacg gatggcatga    2100
cagtaagaga attatgcagt gctgccataa ccatgagtga taacactgcg gccaacttac    2160
ttctgacaac gatcggagga ccgaaggagc taaccgcttt tttgcacaac atggggggatc    2220 atgtaactcg ccttgatcgt tgggaaccgg agctgaatga agccatacca aacgacgagc    2280
gtgacaccac gatgcctgta gtaatggtaa caacgttgcg caaactatta actggcgaac    2340
tacttactct agcttcccgg caacaattaa tagactggat ggaggcggat aaagttgcag    2400
gaccacttct cgcgctcggc cttccggctg gctggtttat tgctgataaa tctggagccg    2460
gtgagcgtgg gtctcgcggt atcattgcag cactggggcc agatggtaag ccctcccgta    2520
tcgtagttat ctacacgacg gggagtcagg caactatgga tgaacgaaat agacagatcg    2580
ctgagatagg tgcctcactg attaagcatt ggtaactgtc agaccaagtt tactcatata    2640
tactttagat tgatttaaaa cttcattttt aatttaaaag gatctaggtg aagatccttt    2700
ttgataatct catgaccaaa atcccttaac gtgagttttc gttccactga gcgtcagacc    2760
ccgtagaaaa gatcaaagga tcttcttgag atcctttttt tctgcgcgta atctgctgct    2820
tgcaaacaaa aaaaccaccg ctaccagcgg tggtttgttt gccggatcaa gagctaccaa    2880 ctcttttttcc gaaggtaact ggcttcagca gagcgcagat accaaatact gtccttctag    2940
tgtagccgta gttaggccac cacttcaaga actctgtagc accgcctaca tacctcgctc    3000
tgctaatcct gttaccagtg gctgctgcca gtggcgataa gtcgtgtctt accgggttgg    3060
actcaagacg atagttaccg gataaggcgc agcggtcggg ctgaacgggg ggttcgtgca    3120
cacagcccag cttggagcga acgacctaca ccgaactgag atacctacag cgtgagctat    3180
gagaaagcgc cacgcttccc gaagggagaa aggcggacag gtatccggta agcggcaggg    3240
tcggaacagg agagcgcacg agggagcttc caggggggaaa cgcctggtat ctttatagtc    3300
ctgtcgggtt tcgccacctc tgacttgagc gtcgattttt gtgatgctcg tcagggggggc    3360 ggagcctatg gaaaaacgcc agcaacgcgg cctttttacg gttcctggcc ttttgctgcg    3420
gttttgctca catgttcttt cctgcgttat cccctgattc tgtggataac cgtattaccg    3480
cctttgagtg agctgatacc gctcgccgca gccgaacgac cgagcgcagc gagtcagtga    3540
gcgaggaagc ggaagagcgc ccaatacgca aaccgcctct ccccgcgcgt tggccgattc    3600
attaatgcag ctggcacgac aggtttcccg actggaaagc gggcagtgag cgcaacgcaa    3660
ttaatgtgag ttagctcact cattaggcac cccaggcttt acactttatg cttccggctc    3720
gtatgttgtg tggaattgtg agcggataac aatttcacac aggaaacagc tatgaccatg    3780
attacgccag atttaattaa ggctgcgcgc tcgctcgctc actgaggccg cccgggcaaa    3840
gcccgggcgt cgggcgacct ttggtcgccc ggcctcagtg agcgagcgag cgcgcagaga    3900
gggagtggcc aactccatca ctaggggttc cttgtagtta atgattaacc cgccatgcta    3960
cttatctacg tagccatgct ctaggaagat cggaattcgc ccttaagcta gcagatcttc    4020
cccacctagc cacctggcaa actgctcctt ctctcaaagg cccaaacatg gcctcccaga    4080
ctgcaacccc caggcagtca ggccctgtct ccacaacctc acagccaccc tggacggaat    4140
ctgcttcttc ccacatttga gtcctcctca gcccctgagc tcctctgggc agggctgttt    4200 cttctccatct ttgtattccc aggggcctgc aaataaatgt ttaatgaacg aacaagagag    4260
tgaattccaa ttccatgcaa caaggattgg gctcctgggc cctaggctat gtgtctggca    4320
ccagaaacgg aagctgcagg ttgcagcccc tgccctcatg gagctcctcc tgtcagagga    4380
```

-continued

```
gtgtggggac tggatgactc cagaggtaac ttgtggggga acgaacaggt aaggggctgt   4440
gtgacgagat gagagactgg gagaataaac cagaaagtct ctagctgtcc agaggacata   4500
gcacagaggc ccatggtccc tatttcaaac ccaggccacc agactgagct gggaccttgg   4560
gacagacaag tcatgcagaa gttaggggac cttctcctcc cttttcctgg atggatcctg   4620
agtaccttct cctccctgac ctcaggcttc ctcctagtgt caccttggcc cctcttagaa   4680
gccaattagg ccctcagttt ctgcagcggg gattaatatg attatgaaca cccccaatct   4740
cccagatgct gattcagcca ggagcttagg agggggaggt cactttataa gggtctgggg   4800
gggtcagaac ccagagtcat cccctgaatt ctgcagatat ccatcacact ggcggccgcg   4860
ccaccatgtc acgcaagata aaggcttttt tgttattact tctctttggc tatgaagcca   4920
cattgggatt atcgtctacc gaggatgaag gcgaggaccc ctggtaccaa aaagcatgca   4980
agtgcgattg ccaaggagga cccaatgctc tgtggtctgc aggtgccacc tccttggact   5040
gtataccaga atgcccatat cacaagcctc tgggtttcga gtcaggggag gtcacaccgg   5100
accagatcac ctgctctaac ccggagcagt atgtgggctg gtattcttcg tggactgcaa   5160
acaaggcccg gctcaacagt caaggctttg ggtgtgcctg gctctccaag ttccaggaca   5220
gtagccagtg gttacagata gatctgaagg agatcaaagt gatttcaggg atcctcaccc   5280
aggggcgctg tgacatcgat gagtggatga ccaagtacag cgtgcagtac aggaccgatg   5340
agcgcctgaa ctgggattac tacaaggacc agactggaaa caaccgggtc ttctatggca   5400
actcggaccg cacctccacg gttcagaacc tgctgcggcc ccccatcatc tcccgcttca   5460
tccgcctcat cccgctgggc tggcacgtcc gcattgccat ccggatggag ctgctggagt   5520
gcgtcagcaa gtgtgcctga a                                              5541
```

<210> SEQ ID NO 19
<211> LENGTH: 346
<212> TYPE: PRT
<213> ORGANISM: Homo sapiens

<400> SEQUENCE: 19

```
Met Ala Leu Leu Lys Val Lys Phe Asp Gln Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
        35                  40                  45

Ser Asp Val Met Asn Asn Ser Glu Ser His Phe Val Pro Asn Ser Leu
    50                  55                  60

Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110

Phe Leu Val Ala Leu Cys Cys Phe Leu Leu Arg Gly Ser Leu Glu Asn
        115                 120                 125

Thr Leu Gly Gln Gly Leu Lys Asn Gly Met Lys Tyr Tyr Arg Asp Thr
    130                 135                 140

Asp Thr Pro Gly Arg Cys Phe Met Lys Lys Thr Ile Asp Met Leu Gln
145                 150                 155                 160
```

```
Ile Glu Phe Lys Cys Cys Gly Asn Asn Gly Phe Arg Asp Trp Phe Glu
            165                 170                 175

Ile Gln Trp Ile Ser Asn Arg Tyr Leu Asp Phe Ser Ser Lys Glu Val
        180                 185                 190

Lys Asp Arg Ile Lys Ser Asn Val Asp Gly Arg Tyr Leu Val Asp Gly
            195                 200                 205

Val Pro Phe Ser Cys Cys Asn Pro Ser Ser Pro Arg Pro Cys Ile Gln
210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
                260                 265                 270

Trp Leu Phe Glu Val Thr Ile Thr Ile Gly Leu Arg Tyr Leu Gln Thr
            275                 280                 285

Ser Leu Asp Gly Val Ser Asn Pro Glu Glu Ser Glu Ser Glu Ser Gln
        290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
                340                 345

<210> SEQ ID NO 20
<211> LENGTH: 470
<212> TYPE: PRT
<213> ORGANISM: Homo sapiens

<400> SEQUENCE: 20

Met Ser His His Pro Ser Gly Leu Arg Ala Gly Phe Ser Ser Thr Ser
1               5                   10                  15

Tyr Arg Arg Thr Phe Gly Pro Pro Ser Leu Ser Pro Gly Ala Phe
            20                  25                  30

Ser Tyr Ser Ser Ser Ser Arg Phe Ser Ser Ser Arg Leu Leu Gly Ser
        35                  40                  45

Ala Ser Pro Ser Ser Ser Val Arg Leu Gly Ser Phe Arg Ser Pro Arg
50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
            100                 105                 110

Glu Lys Val Arg Phe Leu Glu Gln Gln Asn Ala Ala Leu Arg Gly Glu
        115                 120                 125

Leu Ser Gln Ala Arg Gly Gln Glu Pro Ala Arg Ala Asp Gln Leu Cys
130                 135                 140

Gln Gln Glu Leu Arg Glu Leu Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
            180                 185                 190
```

```
Ala Glu His Asn Leu Val Leu Phe Arg Lys Asp Val Asp Ala Thr
            195                 200                 205

Leu Ser Arg Leu Glu Leu Arg Lys Ile Glu Ser Leu Met Asp Glu
    210                 215                 220

Ile Glu Phe Leu Lys Lys Leu His Glu Glu Leu Arg Asp Leu Gln
225                 230                 235                 240

Val Ser Val Glu Ser Gln Gln Val Gln Gln Val Glu Val Ala Thr
                245                 250                 255

Val Lys Pro Glu Leu Thr Ala Ala Leu Arg Asp Ile Arg Ala Gln Tyr
            260                 265                 270

Glu Ser Ile Ala Ala Lys Asn Leu Gln Glu Ala Glu Trp Tyr Lys
            275                 280                 285

Ser Lys Tyr Ala Asp Leu Ser Asp Ala Ala Asn Arg Asn His Glu Ala
            290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335

Leu Arg Gln Leu Arg Glu Leu Glu Glu Gln Phe Ala Leu Glu Ala Gly
            340                 345                 350

Gly Tyr Gln Ala Gly Ala Ala Arg Leu Glu Glu Glu Leu Arg Gln Leu
            355                 360                 365

Lys Glu Glu Met Ala Arg His Leu Arg Glu Tyr Gln Glu Leu Leu Asn
370                 375                 380

Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                405                 410                 415

Leu Asn Ile Lys Thr Thr Val Pro Glu Val Glu Pro Pro Gln Asp Ser
            420                 425                 430

His Ser Arg Lys Thr Val Leu Ile Lys Thr Ile Glu Thr Arg Asn Gly
            435                 440                 445

Glu Val Val Thr Glu Ser Gln Lys Glu Gln Arg Ser Glu Leu Asp Lys
    450                 455                 460

Ser Ser Ala His Ser Tyr
465                 470

<210> SEQ ID NO 21
<211> LENGTH: 1286
<212> TYPE: PRT
<213> ORGANISM: Homo sapiens

<400> SEQUENCE: 21

Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
            20                  25                  30

Lys Thr Gln Pro Pro Leu Ser Arg Met Asn Arg Glu Glu Leu Glu Asp
        35                  40                  45

Ser Phe Phe Arg Leu Arg Glu Asp His Met Leu Val Lys Glu Leu Ser
    50                  55                  60

Trp Lys Gln Gln Asp Glu Ile Lys Arg Leu Arg Thr Thr Leu Leu Arg
65                  70                  75                  80

Leu Thr Ala Ala Gly Arg Asp Leu Arg Val Ala Glu Glu Ala Ala Pro
```

-continued

```
                85                  90                  95
Leu Ser Glu Thr Ala Arg Arg Gly Gln Lys Ala Gly Trp Arg Gln Arg
            100                 105                 110
Leu Ser Met His Gln Arg Pro Gln Met His Arg Leu Gln Gly His Phe
        115                 120                 125
His Cys Val Gly Pro Ala Ser Pro Arg Arg Ala Gln Pro Arg Val Gln
    130                 135                 140
Val Gly His Arg Gln Leu His Thr Ala Gly Ala Pro Val Pro Glu Lys
145                 150                 155                 160
Pro Lys Arg Gly Pro Arg Asp Arg Leu Ser Tyr Thr Ala Pro Pro Ser
                165                 170                 175
Phe Lys Glu His Ala Thr Asn Glu Asn Arg Gly Glu Val Ala Ser Lys
            180                 185                 190
Pro Ser Glu Leu Val Ser Gly Ser Asn Ser Ile Ile Ser Phe Ser Ser
        195                 200                 205
Val Ile Ser Met Ala Lys Pro Ile Gly Leu Cys Met Pro Asn Ser Ala
    210                 215                 220
His Ile Met Ala Ser Asn Thr Met Gln Val Glu Glu Pro Pro Lys Ser
225                 230                 235                 240
Pro Glu Lys Met Trp Pro Lys Asp Glu Asn Phe Glu Gln Arg Ser Ser
                245                 250                 255
Leu Glu Cys Ala Gln Lys Ala Ala Glu Leu Arg Ala Ser Ile Lys Glu
            260                 265                 270
Lys Val Glu Leu Ile Arg Leu Lys Lys Leu Leu His Glu Arg Asn Ala
        275                 280                 285
Ser Leu Val Met Thr Lys Ala Gln Leu Thr Glu Val Gln Glu Ala Tyr
    290                 295                 300
Glu Thr Leu Leu Gln Lys Asn Gln Gly Ile Leu Ser Ala Ala His Glu
305                 310                 315                 320
Ala Leu Leu Lys Gln Val Asn Glu Leu Arg Ala Glu Leu Lys Glu Glu
                325                 330                 335
Ser Lys Lys Ala Val Ser Leu Lys Ser Gln Leu Glu Asp Val Ser Ile
            340                 345                 350
Leu Gln Met Thr Leu Lys Glu Phe Gln Glu Arg Val Glu Asp Leu Glu
        355                 360                 365
Lys Glu Arg Lys Leu Leu Asn Asp Asn Tyr Asp Lys Leu Leu Glu Ser
    370                 375                 380
Met Leu Asp Ser Ser Asp Ser Ser Gln Pro His Trp Ser Asn Glu
385                 390                 395                 400
Leu Ile Ala Glu Gln Leu Gln Gln Val Ser Gln Leu Gln Asp Gln
                405                 410                 415
Leu Asp Ala Glu Leu Glu Asp Lys Arg Lys Val Leu Leu Glu Leu Ser
            420                 425                 430
Arg Glu Lys Ala Gln Asn Glu Asp Leu Lys Leu Glu Val Thr Asn Ile
        435                 440                 445
Leu Gln Lys His Lys Gln Glu Val Glu Leu Leu Gln Asn Ala Ala Thr
    450                 455                 460
Ile Ser Gln Pro Pro Asp Arg Gln Ser Glu Pro Ala Thr His Pro Ala
465                 470                 475                 480
Val Leu Gln Glu Asn Thr Gln Ile Glu Pro Ser Glu Pro Lys Asn Gln
                485                 490                 495
Glu Glu Lys Lys Leu Ser Gln Val Leu Asn Glu Leu Gln Val Ser His
            500                 505                 510
```

```
Ala Glu Thr Thr Leu Glu Leu Glu Lys Thr Arg Asp Met Leu Ile Leu
            515                 520                 525

Gln Arg Lys Ile Asn Val Cys Tyr Gln Glu Leu Glu Ala Met Met
530                 535                 540

Thr Lys Ala Asp Asn Asp Asn Arg Asp His Lys Glu Lys Leu Glu Arg
545                 550                 555                 560

Leu Thr Arg Leu Leu Asp Leu Lys Asn Arg Ile Lys Gln Leu Glu
            565                 570                 575

Gly Ile Leu Arg Ser His Asp Leu Pro Thr Glu Gln Leu Lys Asp
            580                 585                 590

Val Ala Tyr Gly Thr Arg Pro Leu Ser Leu Cys Leu Thr Leu Pro
            595                 600                 605

Ala His Gly Asp Glu Asp Lys Val Asp Ile Ser Leu Leu His Gln Gly
610                 615                 620

Glu Asn Leu Phe Glu Leu His Ile His Gln Ala Phe Leu Thr Ser Ala
625                 630                 635                 640

Ala Leu Ala Gln Ala Gly Asp Thr Gln Pro Thr Thr Phe Cys Thr Tyr
                645                 650                 655

Ser Phe Tyr Asp Phe Glu Thr His Cys Thr Pro Leu Ser Val Gly Pro
                660                 665                 670

Gln Pro Leu Tyr Asp Phe Thr Ser Gln Tyr Val Met Glu Thr Asp Ser
            675                 680                 685

Leu Phe Leu His Tyr Leu Gln Glu Ala Ser Ala Arg Leu Asp Ile His
            690                 695                 700

Gln Ala Met Ala Ser Glu His Ser Thr Leu Ala Ala Gly Trp Ile Cys
705                 710                 715                 720

Phe Asp Arg Val Leu Glu Thr Val Glu Lys Val His Gly Leu Ala Thr
                725                 730                 735

Leu Ile Gly Ala Gly Gly Glu Glu Phe Gly Val Leu Glu Tyr Trp Met
                740                 745                 750

Arg Leu Arg Phe Pro Ile Lys Pro Ser Leu Gln Ala Cys Asn Lys Arg
            755                 760                 765

Lys Lys Ala Gln Val Tyr Leu Ser Thr Asp Val Leu Gly Gly Arg Lys
770                 775                 780

Ala Gln Glu Glu Glu Phe Arg Ser Glu Ser Trp Glu Pro Gln Asn Glu
785                 790                 795                 800

Leu Trp Ile Glu Ile Thr Lys Cys Cys Gly Leu Arg Ser Arg Trp Leu
                805                 810                 815

Gly Thr Gln Pro Ser Pro Tyr Ala Val Tyr Arg Phe Phe Thr Phe Ser
            820                 825                 830

Asp His Asp Thr Ala Ile Ile Pro Ala Ser Asn Asn Pro Tyr Phe Arg
            835                 840                 845

Asp Gln Ala Arg Phe Pro Val Leu Val Thr Ser Asp Leu Asp His Tyr
850                 855                 860

Leu Arg Arg Glu Ala Leu Ser Ile His Val Phe Asp Asp Glu Asp Leu
865                 870                 875                 880

Glu Pro Gly Ser Tyr Leu Gly Arg Ala Arg Val Pro Leu Leu Pro Leu
                885                 890                 895

Ala Lys Asn Glu Ser Ile Lys Gly Asp Phe Asn Leu Thr Asp Pro Ala
                900                 905                 910

Glu Lys Pro Asn Gly Ser Ile Gln Val Gln Leu Asp Trp Lys Phe Pro
            915                 920                 925
```

Tyr Ile Pro Pro Glu Ser Phe Leu Lys Pro Glu Ala Gln Thr Lys Gly
930             935                 940

Lys Asp Thr Lys Asp Ser Ser Lys Ile Ser Glu Glu Lys Ala
945                 950                 955                 960

Ser Phe Pro Ser Gln Asp Gln Met Ala Ser Pro Glu Val Pro Ile Glu
                965                 970                 975

Ala Gly Gln Tyr Arg Ser Lys Arg Lys Pro Pro His Gly Gly Glu Arg
            980                 985                 990

Lys Glu Lys Glu His Gln Val Val Ser Tyr Ser Arg Arg Lys His Gly
        995                 1000                1005

Lys Arg Ile Gly Val Gln Gly Lys Asn Arg Met Glu Tyr Leu Ser
    1010                1015                1020

Leu Asn Ile Leu Asn Gly Asn Thr Pro Glu Gln Val Asn Tyr Thr
    1025                1030                1035

Glu Trp Lys Phe Ser Glu Thr Asn Ser Phe Ile Gly Asp Gly Phe
    1040                1045                1050

Lys Asn Gln His Glu Glu Glu Met Thr Leu Ser His Ser Ala
    1055                1060                1065

Leu Lys Gln Lys Glu Pro Leu His Pro Val Asn Asp Lys Glu Ser
    1070                1075                1080

Ser Glu Gln Gly Ser Glu Val Ser Glu Ala Gln Thr Thr Asp Ser
    1085                1090                1095

Asp Asp Val Ile Val Pro Pro Met Ser Gln Lys Tyr Pro Lys Ala
    1100                1105                1110

Asp Ser Glu Lys Met Cys Ile Glu Ile Val Ser Leu Ala Phe Tyr
    1115                1120                1125

Pro Glu Ala Glu Val Met Ser Asp Glu Asn Ile Lys Gln Val Tyr
    1130                1135                1140

Val Glu Tyr Lys Phe Tyr Asp Leu Pro Leu Ser Glu Thr Glu Thr
    1145                1150                1155

Pro Val Ser Leu Arg Lys Pro Arg Ala Gly Glu Glu Ile His Phe
    1160                1165                1170

His Phe Ser Lys Val Ile Asp Leu Asp Pro Gln Glu Gln Gln Gly
    1175                1180                1185

Arg Arg Arg Phe Leu Phe Asp Met Leu Asn Gly Gln Asp Pro Asp
    1190                1195                1200

Gln Gly His Leu Lys Phe Thr Val Val Ser Asp Pro Leu Asp Glu
    1205                1210                1215

Glu Lys Lys Glu Cys Glu Glu Val Gly Tyr Ala Tyr Leu Gln Leu
    1220                1225                1230

Trp Gln Ile Leu Glu Ser Gly Arg Asp Ile Leu Glu Gln Glu Leu
    1235                1240                1245

Asp Ile Val Ser Pro Glu Asp Leu Ala Thr Pro Ile Gly Arg Leu
    1250                1255                1260

Lys Val Ser Leu Gln Ala Ala Val Leu His Ala Ile Tyr Lys
    1265                1270                1275

Glu Met Thr Glu Asp Leu Phe Ser
    1280                1285

<210> SEQ ID NO 22
<211> LENGTH: 240
<212> TYPE: PRT
<213> ORGANISM: Adeno-associated virus-1

<400> SEQUENCE: 22

```
Thr Phe Ser Tyr Thr Phe Glu Glu Val Pro Phe His Ser Ser Tyr Ala
1               5                   10                  15

His Ser Gln Ser Leu Asp Arg Leu Met Asn Pro Leu Ile Asp Gln Tyr
                20                  25                  30

Leu Tyr Tyr Leu Asn Arg Thr Gln Asn Gln Ser Gly Ser Ala Gln Asn
            35                  40                  45

Lys Asp Leu Leu Phe Ser Arg Gly Ser Pro Ala Gly Met Ser Val Gln
    50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
            100                 105                 110

Ala Met Ala Ser His Lys Asp Asp Glu Asp Lys Phe Phe Pro Met Ser
        115                 120                 125

Gly Val Met Ile Phe Gly Lys Glu Ser Ala Gly Ala Ser Asn Thr Ala
    130                 135                 140

Leu Asp Asn Val Met Ile Thr Asp Glu Glu Ile Lys Ala Thr Asn
145                 150                 155                 160

Pro Val Ala Thr Glu Arg Phe Gly Thr Val Ala Val Asn Phe Gln Ser
                165                 170                 175

Ser Ser Thr Asp Pro Ala Thr Gly Asp Val His Ala Met Gly Ala Leu
            180                 185                 190

Pro Gly Met Val Trp Gln Asp Arg Asp Val Tyr Leu Gln Gly Pro Ile
        195                 200                 205

Trp Ala Lys Ile Pro His Thr Asp Gly His Phe His Pro Ser Pro Leu
210                 215                 220

Met Gly Gly Phe Gly Leu Lys Asn Pro Pro Pro Gln Ile Leu Ile Lys
225                 230                 235                 240

<210> SEQ ID NO 23
<211> LENGTH: 240
<212> TYPE: PRT
<213> ORGANISM: Adeno-associated virus-6

<400> SEQUENCE: 23

Thr Phe Ser Tyr Thr Phe Glu Asp Val Pro Phe His Ser Ser Tyr Ala
1               5                   10                  15

His Ser Gln Ser Leu Asp Arg Leu Met Asn Pro Leu Ile Asp Gln Tyr
                20                  25                  30

Leu Tyr Tyr Leu Asn Arg Thr Gln Asn Gln Ser Gly Ser Ala Gln Asn
            35                  40                  45

Lys Asp Leu Leu Phe Ser Arg Gly Ser Pro Ala Gly Met Ser Val Gln
    50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
            100                 105                 110

Ala Met Ala Ser His Lys Asp Asp Lys Asp Lys Phe Phe Pro Met Ser
        115                 120                 125

Gly Val Met Ile Phe Gly Lys Glu Ser Ala Gly Ala Ser Asn Thr Ala
```

```
                130                135                140
Leu Asp Asn Val Met Ile Thr Asp Glu Glu Glu Ile Lys Ala Thr Asn
145                150                155                160

Pro Val Ala Thr Glu Arg Phe Gly Thr Val Ala Val Asn Leu Gln Ser
                165                170                175

Ser Ser Thr Asp Pro Ala Thr Gly Asp Val His Val Met Gly Ala Leu
                180                185                190

Pro Gly Met Val Trp Gln Asp Arg Asp Val Tyr Leu Gln Gly Pro Ile
                195                200                205

Trp Ala Lys Ile Pro His Thr Asp Gly His Phe His Pro Ser Pro Leu
                210                215                220

Met Gly Gly Phe Gly Leu Lys His Pro Pro Pro Gln Ile Leu Ile Lys
225                230                235                240

<210> SEQ ID NO 24
<211> LENGTH: 240
<212> TYPE: PRT
<213> ORGANISM: Adeno-associated virus-3

<400> SEQUENCE: 24

Phe Ser Tyr Thr Phe Glu Asp Val Pro Phe His Ser Ser Tyr Ala His
1                5                  10                 15

Ser Gln Ser Leu Asp Arg Leu Met Asn Pro Leu Ile Asp Gln Tyr Leu
                20                 25                 30

Tyr Tyr Leu Asn Arg Thr Gln Gly Thr Thr Ser Gly Thr Thr Asn Gln
                35                 40                 45

Ser Arg Leu Leu Phe Ser Gln Ala Gly Pro Gln Ser Met Ser Leu Gln
50                 55                 60

Ala Arg Asn Trp Leu Pro Gly Pro Cys Tyr Arg Gln Gln Arg Leu Ser
65                 70                 75                 80

Lys Thr Ala Asn Asp Asn Asn Asn Ser Asn Phe Pro Trp Thr Ala Ala
                85                 90                 95

Ser Lys Tyr His Leu Asn Gly Arg Asp Ser Leu Val Asn Pro Gly Pro
                100                105                110

Ala Met Ala Ser His Lys Asp Asp Glu Glu Lys Phe Phe Pro Met His
                115                120                125

Gly Asn Leu Ile Phe Gly Lys Glu Gly Thr Thr Ala Ser Asn Ala Glu
130                135                140

Leu Asp Asn Val Met Ile Thr Asp Glu Glu Glu Ile Arg Thr Thr Asn
145                150                155                160

Pro Val Ala Thr Glu Gln Tyr Gly Thr Val Ala Asn Asn Leu Gln Ser
                165                170                175

Ser Asn Thr Ala Pro Thr Thr Gly Thr Val Asn His Gln Gly Ala Leu
                180                185                190

Pro Gly Met Val Trp Gln Asp Arg Asp Val Tyr Leu Gln Gly Pro Ile
                195                200                205

Trp Ala Lys Ile Pro His Thr Asp Gly His Phe His Pro Ser Pro Leu
                210                215                220

Met Gly Gly Phe Gly Leu Lys His Pro Pro Pro Gln Ile Met Ile Lys
225                230                235                240

<210> SEQ ID NO 25
<211> LENGTH: 240
<212> TYPE: PRT
<213> ORGANISM: Adeno-associated virus-2
```

-continued

<400> SEQUENCE: 25

Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
            20                  25                  30

Tyr Tyr Leu Ser Arg Thr Asn Thr Pro Ser Gly Thr Thr Thr Gln Ser
        35                  40                  45

Arg Leu Gln Phe Ser Gln Ala Gly Ala Ser Asp Ile Arg Asp Gln Ser
    50                  55                  60

Arg Asn Trp Leu Pro Gly Pro Cys Tyr Arg Gln Gln Arg Val Ser Lys
65                  70                  75                  80

Thr Ser Ala Asp Asn Asn Asn Ser Glu Tyr Ser Trp Thr Gly Ala Thr
                85                  90                  95

Lys Tyr His Leu Asn Gly Arg Asp Ser Leu Val Asn Pro Gly Pro Ala
            100                 105                 110

Met Ala Ser His Lys Asp Asp Glu Glu Lys Phe Phe Pro Gln Ser Gly
        115                 120                 125

Val Leu Ile Phe Gly Lys Gln Gly Ser Glu Lys Thr Asn Val Asp Ile
    130                 135                 140

Glu Lys Val Met Ile Thr Asp Glu Glu Ile Arg Thr Thr Asn Pro
145                 150                 155                 160

Val Ala Thr Glu Gln Tyr Gly Ser Val Ser Thr Asn Leu Gln Arg Gly
                165                 170                 175

Asn Arg Gln Ala Ala Thr Ala Asp Val Asn Thr Gln Gly Val Leu Pro
            180                 185                 190

Gly Met Val Trp Gln Asp Arg Asp Val Tyr Leu Gln Gly Pro Ile Trp
        195                 200                 205

Ala Lys Ile Pro His Thr Asp Gly His Phe His Pro Ser Pro Leu Met
    210                 215                 220

Gly Gly Phe Gly Leu Lys His Pro Pro Pro Gln Ile Leu Ile Lys Asn
225                 230                 235                 240

<210> SEQ ID NO 26
<211> LENGTH: 243
<212> TYPE: PRT
<213> ORGANISM: Adeno-associated virus-8

<400> SEQUENCE: 26

Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
    50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

```
Ser Asn Gly Ile Leu Ile Phe Gly Lys Gln Asn Ala Ala Arg Asp Asn
    130                 135                 140

Ala Asp Tyr Ser Asp Val Met Leu Thr Ser Glu Glu Ile Lys Thr
145                 150                 155                 160

Thr Asn Pro Val Ala Thr Glu Glu Tyr Gly Ile Val Ala Asp Asn Leu
                165                 170                 175

Gln Gln Gln Asn Thr Ala Pro Gln Ile Gly Thr Val Asn Ser Gln Gly
            180                 185                 190

Ala Leu Pro Gly Met Val Trp Gln Asn Arg Asp Val Tyr Leu Gln Gly
        195                 200                 205

Pro Ile Trp Ala Lys Ile Pro His Thr Asp Gly Asn Phe His Pro Ser
210                 215                 220

Pro Leu Met Gly Gly Phe Gly Leu Lys His Pro Pro Gln Ile Leu
225                 230                 235                 240

Ile Lys Asn

<210> SEQ ID NO 27
<211> LENGTH: 243
<212> TYPE: PRT
<213> ORGANISM: Artificial sequence
<220> FEATURE:
<223> OTHER INFORMATION: Synthetic polypeptide

<400> SEQUENCE: 27

Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
    50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
    130                 135                 140

Ala Asp Tyr Ser Asp Val Met Leu Thr Ser Glu Glu Ile Lys Thr
145                 150                 155                 160

Thr Asn Pro Val Ala Thr Glu Glu Tyr Gly Ile Val Ala Asp Asn Leu
                165                 170                 175

Gln Gly Gln Arg Gln Ala Ala Gln Ile Gly Thr Val Asn Ser Gln Gly
            180                 185                 190

Ala Leu Pro Gly Met Val Trp Gln Asn Arg Asp Val Tyr Leu Gln Gly
        195                 200                 205

Pro Ile Trp Ala Lys Ile Pro His Thr Asp Gly Asn Phe His Pro Ser
210                 215                 220

Pro Leu Met Gly Gly Phe Gly Leu Lys His Pro Pro Gln Ile Leu
225                 230                 235                 240

Ile Lys Asn
```

<210> SEQ ID NO 28
<211> LENGTH: 241
<212> TYPE: PRT
<213> ORGANISM: Adeno-associated virus-rh8

<400> SEQUENCE: 28

```
Phe Gln Phe Ser Tyr Thr Phe Glu Asp Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Val Arg Thr Gln Thr Thr Gly Thr Gly Gly Thr
        35                  40                  45

Gln Thr Leu Ala Phe Ser Gln Ala Gly Pro Ser Ser Met Ala Asn Gln
    50                  55                  60

Ala Arg Asn Trp Val Pro Gly Pro Cys Tyr Arg Gln Gln Arg Val Ser
65                  70                  75                  80

Thr Thr Thr Asn Gln Asn Asn Asn Ser Asn Phe Ala Trp Thr Gly Ala
                85                  90                  95

Ala Lys Phe Lys Leu Asn Gly Arg Asp Ser Leu Met Asn Pro Gly Val
            100                 105                 110

Ala Met Ala Ser His Lys Asp Asp Asp Arg Phe Phe Pro Ser Ser
        115                 120                 125

Gly Val Leu Ile Phe Gly Lys Gln Gly Ala Gly Asn Asp Gly Val Asp
    130                 135                 140

Tyr Ser Gln Val Leu Ile Thr Asp Glu Glu Ile Lys Ala Thr Asn
145                 150                 155                 160

Pro Val Ala Thr Glu Glu Tyr Gly Ala Val Ala Ile Asn Asn Gln Ala
                165                 170                 175

Ala Asn Thr Gln Ala Gln Thr Gly Leu Val His Asn Gln Gly Val Ile
            180                 185                 190

Pro Gly Met Val Trp Gln Asn Arg Asp Val Tyr Leu Gln Gly Pro Ile
        195                 200                 205

Trp Ala Lys Ile Pro His Thr Asp Gly Asn Phe His Pro Ser Pro Leu
    210                 215                 220

Met Gly Gly Phe Gly Leu Lys His Pro Pro Pro Gln Ile Leu Ile Lys
225                 230                 235                 240

Asn
```

<210> SEQ ID NO 29
<211> LENGTH: 243
<212> TYPE: PRT
<213> ORGANISM: Adeno-associated virus-10

<400> SEQUENCE: 29

```
Asn Phe Glu Phe Ser Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Ser Thr Gly Gly Thr Gln
        35                  40                  45

Gly Thr Gln Gln Leu Leu Phe Ser Gln Ala Gly Pro Ala Asn Met Ser
    50                  55                  60

Ala Gln Ala Lys Asn Trp Leu Pro Gly Pro Cys Tyr Arg Gln Gln Arg
65                  70                  75                  80
```

```
Val Ser Thr Thr Leu Ser Gln Asn Asn Asn Ser Asn Phe Ala Trp Thr
                85                  90                  95
Gly Ala Thr Lys Tyr His Leu Asn Gly Arg Asp Ser Leu Val Asn Pro
           100                 105                 110
Gly Val Ala Met Ala Thr His Lys Asp Asp Glu Glu Arg Phe Phe Pro
       115                 120                 125
Ser Ser Gly Val Leu Met Phe Gly Lys Gln Gly Ala Gly Arg Asp Asn
130                 135                 140
Val Asp Tyr Ser Ser Val Met Leu Thr Ser Glu Glu Ile Lys Thr
145                 150                 155                 160
Thr Asn Pro Val Ala Thr Glu Gln Tyr Gly Val Val Ala Asp Asn Leu
                165                 170                 175
Gln Gln Ala Asn Thr Gly Pro Ile Val Gly Asn Val Asn Ser Gln Gly
           180                 185                 190
Ala Leu Pro Gly Met Val Trp Gln Asn Arg Asp Val Tyr Leu Gln Gly
       195                 200                 205
Pro Ile Trp Ala Lys Ile Pro His Thr Asp Gly Asn Phe His Pro Ser
   210                 215                 220
Pro Leu Met Gly Gly Phe Gly Leu Lys His Pro Pro Gln Ile Leu
225                 230                 235                 240
Ile Lys Asn

<210> SEQ ID NO 30
<211> LENGTH: 242
<212> TYPE: PRT
<213> ORGANISM: Adeno-associated virus-7

<400> SEQUENCE: 30

Phe Glu Phe Ser Tyr Ser Phe Glu Asp Val Pro Phe His Ser Ser Tyr
1               5                   10                  15
Ala His Ser Gln Ser Leu Asp Arg Leu Met Asn Pro Leu Ile Asp Gln
            20                  25                  30
Tyr Leu Tyr Tyr Leu Ala Arg Thr Gln Ser Asn Pro Gly Gly Thr Ala
        35                  40                  45
Gly Asn Arg Glu Leu Gln Phe Tyr Gln Gly Gly Pro Ser Thr Met Ala
    50                  55                  60
Glu Gln Ala Lys Asn Trp Leu Pro Gly Pro Cys Phe Arg Gln Arg
65                  70                  75                  80
Val Ser Lys Thr Leu Asp Gln Asn Asn Asn Ser Asn Phe Ala Trp Thr
                85                  90                  95
Gly Ala Thr Lys Tyr His Leu Asn Gly Arg Asn Ser Leu Val Asn Pro
           100                 105                 110
Gly Val Ala Met Ala Thr His Lys Asp Asp Glu Asp Arg Phe Phe Pro
       115                 120                 125
Ser Ser Gly Val Leu Ile Phe Gly Lys Thr Gly Ala Thr Asn Lys Thr
130                 135                 140
Thr Leu Glu Asn Val Leu Met Thr Asn Glu Glu Ile Arg Pro Thr
145                 150                 155                 160
Asn Pro Val Ala Thr Glu Glu Tyr Gly Ile Val Ser Ser Asn Leu Gln
                165                 170                 175
Ala Ala Asn Thr Ala Ala Gln Thr Gln Val Val Asn Asn Gln Gly Ala
           180                 185                 190
Leu Pro Gly Met Val Trp Gln Asn Arg Asp Val Tyr Leu Gln Gly Pro
       195                 200                 205
```

Ile Trp Ala Lys Ile Pro His Thr Asp Gly Asn Phe His Pro Ser Pro
210                 215                 220

Leu Met Gly Gly Phe Gly Leu Lys His Pro Pro Gln Ile Leu Ile
225                 230                 235                 240

Lys Asn

<210> SEQ ID NO 31
<211> LENGTH: 240
<212> TYPE: PRT
<213> ORGANISM: Adeno-associated virus-9

<400> SEQUENCE: 31

Phe Gln Phe Ser Tyr Glu Phe Glu Asn Val Pro Phe His Ser Ser Tyr
1               5                   10                  15

Ala His Ser Gln Ser Leu Asp Arg Leu Met Asn Pro Leu Ile Asp Gln
                20                  25                  30

Tyr Leu Tyr Tyr Leu Ser Lys Thr Ile Asn Gly Ser Gly Gln Asn Gln
            35                  40                  45

Gln Thr Leu Lys Phe Ser Val Ala Gly Pro Ser Asn Met Ala Val Gln
50                  55                  60

Gly Arg Asn Tyr Ile Pro Gly Pro Ser Tyr Arg Gln Gln Arg Val Ser
65                  70                  75                  80

Thr Thr Val Thr Gln Asn Asn Asn Ser Glu Phe Ala Trp Pro Gly Ala
                85                  90                  95

Ser Ser Trp Ala Leu Asn Gly Arg Asn Ser Leu Met Asn Pro Gly Pro
            100                 105                 110

Ala Met Ala Ser His Lys Glu Gly Glu Asp Arg Phe Phe Pro Leu Ser
        115                 120                 125

Gly Ser Leu Ile Phe Gly Lys Gln Gly Thr Gly Arg Asp Asn Val Asp
130                 135                 140

Ala Asp Lys Val Met Ile Thr Asn Glu Glu Glu Ile Lys Thr Thr Asn
145                 150                 155                 160

Pro Val Ala Thr Glu Ser Tyr Gly Gln Val Ala Thr Asn His Gln Ser
                165                 170                 175

Ala Gln Ala Gln Ala Gln Thr Gly Trp Val Gln Asn Gln Gly Ile Leu
            180                 185                 190

Pro Gly Met Val Trp Gln Asp Arg Asp Val Tyr Leu Gln Gly Pro Ile
        195                 200                 205

Trp Ala Lys Ile Pro His Thr Asp Gly Asn Phe His Pro Ser Pro Leu
210                 215                 220

Met Gly Gly Phe Gly Met Lys His Pro Pro Pro Gln Ile Leu Ile Lys
225                 230                 235                 240

<210> SEQ ID NO 32
<211> LENGTH: 239
<212> TYPE: PRT
<213> ORGANISM: Artificial sequence
<220> FEATURE:
<223> OTHER INFORMATION: Synthetic polypeptide

<400> SEQUENCE: 32

Gln Phe Ser Tyr Glu Phe Glu Asn Val Pro Phe His Ser Ser Tyr Ala
1               5                   10                  15

His Ser Gln Ser Leu Asp Arg Leu Met Asn Pro Leu Ile Asp Gln Tyr
                20                  25                  30

Leu Tyr Tyr Leu Ser Lys Thr Ile Asn Gly Ser Gly Gln Asn Gln Gln
            35                  40                  45

```
Thr Leu Lys Phe Ser Val Ala Gly Pro Ser Asn Met Ala Val Gln Gly
         50                  55                  60

Arg Asn Tyr Ile Pro Gly Pro Ser Tyr Arg Gln Gln Arg Val Ser Thr
 65                  70                  75                  80

Thr Val Thr Gln Asn Asn Asn Ser Glu Phe Ala Trp Pro Gly Ala Ser
                 85                  90                  95

Ser Trp Ala Leu Asn Gly Arg Asn Ser Leu Met Asn Pro Gly Pro Ala
            100                 105                 110

Met Ala Ser His Lys Glu Gly Glu Asp Arg Phe Phe Pro Leu Ser Gly
            115                 120                 125

Ser Leu Ile Phe Gly Lys Gln Gly Thr Gly Arg Asp Asn Val Asp Ala
        130                 135                 140

Asp Lys Val Met Ile Thr Asn Glu Glu Glu Ile Lys Thr Thr Asn Pro
145                 150                 155                 160

Val Ala Thr Glu Ser Tyr Gly Gln Val Ala Thr Asn His Gln Ser Gly
                165                 170                 175

Gln Ala Gln Ala Ala Thr Gly Trp Val Gln Asn Gln Gly Ile Leu Pro
            180                 185                 190

Gly Met Val Trp Gln Asp Arg Asp Val Tyr Leu Gln Gly Pro Ile Trp
        195                 200                 205

Ala Lys Ile Pro His Thr Asp Gly Asn Phe His Pro Ser Pro Leu Met
    210                 215                 220

Gly Gly Phe Gly Met Lys His Pro Pro Gln Ile Leu Ile Lys
225                 230                 235

<210> SEQ ID NO 33
<211> LENGTH: 240
<212> TYPE: PRT
<213> ORGANISM: Adeno-associated virus-5

<400> SEQUENCE: 33

Asn Phe Glu Phe Thr Tyr Asn Phe Glu Glu Val Pro Phe His Ser Ser
  1               5                  10                  15

Phe Ala Pro Ser Gln Asn Leu Phe Lys Leu Ala Asn Pro Leu Val Asp
             20                  25                  30

Gln Tyr Leu Tyr Arg Phe Val Ser Thr Asn Asn Thr Gly Gly Val Gln
         35                  40                  45

Phe Asn Lys Asn Leu Ala Gly Arg Tyr Ala Asn Thr Tyr Lys Asn Trp
 50                  55                  60

Phe Pro Gly Pro Met Gly Arg Thr Gln Gly Trp Asn Leu Gly Ser Gly
 65                  70                  75                  80

Val Asn Arg Ala Ser Val Ser Ala Phe Ala Thr Thr Asn Arg Met Glu
                 85                  90                  95

Leu Glu Gly Ala Ser Tyr Gln Val Pro Pro Gln Pro Asn Gly Met Thr
            100                 105                 110

Asn Asn Leu Gln Gly Ser Asn Thr Tyr Ala Leu Glu Asn Thr Met Ile
        115                 120                 125

Phe Asn Ser Gln Pro Ala Asn Pro Gly Thr Thr Ala Thr Tyr Leu Glu
    130                 135                 140

Gly Asn Met Leu Ile Thr Ser Glu Ser Glu Thr Gln Pro Val Asn Arg
145                 150                 155                 160

Val Ala Tyr Asn Val Gly Gly Gln Met Ala Thr Asn Asn Gln Ser Ser
                165                 170                 175

Thr Thr Ala Pro Ala Thr Gly Thr Tyr Asn Leu Gln Glu Ile Val Pro
```

```
                      180                 185                 190
Gly Ser Val Trp Met Glu Arg Asp Val Tyr Leu Gln Gly Pro Ile Trp
            195                 200                 205

Ala Lys Ile Pro Glu Thr Gly Ala His Phe His Pro Ser Pro Ala Met
        210                 215                 220

Gly Gly Phe Gly Leu Lys His Pro Pro Met Met Leu Ile Lys Asn
225                 230                 235                 240

<210> SEQ ID NO 34
<211> LENGTH: 250
<212> TYPE: PRT
<213> ORGANISM: Artificial sequence
<220> FEATURE:
<223> OTHER INFORMATION: Synthetic polypeptide

<400> SEQUENCE: 34

Thr Phe Ser Tyr Thr Phe Glu Glu Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Asn Arg Thr Gln Asn Gln Ser Gly Ser Ala Gln Asn
        35                  40                  45

Lys Asp Leu Leu Phe Ser Arg Gly Ser Pro Ala Gly Met Ser Val Gln
50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
            100                 105                 110

Ala Met Ala Ser His Lys Asp Asp Glu Asp Lys Phe Phe Pro Met Ser
        115                 120                 125

Gly Val Met Ile Phe Gly Lys Glu Ser Ala Gly Ala Ser Asn Thr Ala
    130                 135                 140

Leu Asp Asn Val Met Ile Thr Asp Glu Glu Glu Ile Lys Ala Thr Asn
145                 150                 155                 160

Pro Val Ala Thr Glu Arg Phe Gly Thr Val Ala Val Asn Phe Gln Ser
                165                 170                 175

Ser Ser Thr Asp Leu Ala Leu Gly Glu Thr Thr Arg Pro Ala Pro Ala
            180                 185                 190

Thr Gly Asp Val His Ala Met Gly Ala Leu Pro Gly Met Val Trp Gln
        195                 200                 205

Asp Arg Asp Val Tyr Leu Gln Gly Pro Ile Trp Ala Lys Ile Pro His
    210                 215                 220

Thr Asp Gly His Phe His Pro Ser Pro Leu Met Gly Gly Phe Gly Leu
225                 230                 235                 240

Lys Asn Pro Pro Gln Ile Leu Ile Lys
                245                 250

<210> SEQ ID NO 35
<211> LENGTH: 250
<212> TYPE: PRT
<213> ORGANISM: Artificial sequence
<220> FEATURE:
<223> OTHER INFORMATION: Synthetic polypeptide

<400> SEQUENCE: 35
```

```
Thr Phe Ser Tyr Thr Phe Glu Asp Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Asn Arg Thr Gln Asn Gln Ser Gly Ser Ala Gln Asn
        35                  40                  45

Lys Asp Leu Leu Phe Ser Arg Gly Ser Pro Ala Gly Met Ser Val Gln
50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
                100                 105                 110

Ala Met Ala Ser His Lys Asp Lys Asp Lys Phe Phe Pro Met Ser
                115                 120                 125

Gly Val Met Ile Phe Gly Lys Glu Ser Ala Gly Ala Ser Asn Thr Ala
        130                 135                 140

Leu Asp Asn Val Met Ile Thr Asp Glu Glu Ile Lys Ala Thr Asn
145                 150                 155                 160

Pro Val Ala Thr Glu Arg Phe Gly Thr Val Ala Val Asn Leu Gln Ser
                165                 170                 175

Ser Ser Thr Asp Leu Ala Leu Gly Glu Thr Thr Arg Pro Ala Pro Ala
                180                 185                 190

Thr Gly Asp Val His Val Met Gly Ala Leu Pro Gly Met Val Trp Gln
            195                 200                 205

Asp Arg Asp Val Tyr Leu Gln Gly Pro Ile Trp Ala Lys Ile Pro His
            210                 215                 220

Thr Asp Gly His Phe His Pro Ser Pro Leu Met Gly Gly Phe Gly Leu
225                 230                 235                 240

Lys His Pro Pro Gln Ile Leu Ile Lys
                245                 250

<210> SEQ ID NO 36
<211> LENGTH: 250
<212> TYPE: PRT
<213> ORGANISM: Artificial sequence
<220> FEATURE:
<223> OTHER INFORMATION: Synthetic polypeptide

<400> SEQUENCE: 36

Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
            20                  25                  30

Tyr Tyr Leu Ser Arg Thr Asn Thr Pro Ser Gly Thr Thr Thr Gln Ser
        35                  40                  45

Arg Leu Gln Phe Ser Gln Ala Gly Ala Ser Asp Ile Arg Asp Gln Ser
    50                  55                  60

Arg Asn Trp Leu Pro Gly Pro Cys Tyr Arg Gln Gln Arg Val Ser Lys
65                  70                  75                  80

Thr Ser Ala Asp Asn Asn Asn Ser Glu Tyr Ser Trp Thr Gly Ala Thr
                85                  90                  95

Lys Tyr His Leu Asn Gly Arg Asp Ser Leu Val Asn Pro Gly Pro Ala
                100                 105                 110
```

```
Met Ala Ser His Lys Asp Asp Glu Lys Phe Phe Pro Gln Ser Gly
            115                 120                 125

Val Leu Ile Phe Gly Lys Gln Gly Ser Glu Lys Thr Asn Val Asp Ile
        130                 135                 140

Glu Lys Val Met Ile Thr Asp Glu Glu Ile Arg Thr Thr Asn Pro
145                 150                 155                 160

Val Ala Thr Glu Gln Tyr Gly Ser Val Ser Thr Asn Leu Gln Arg Gly
                165                 170                 175

Asn Leu Ala Leu Gly Glu Thr Thr Arg Pro Ala Arg Gln Ala Ala Thr
            180                 185                 190

Ala Asp Val Asn Thr Gln Gly Val Leu Pro Gly Met Val Trp Gln Asp
        195                 200                 205

Arg Asp Val Tyr Leu Gln Gly Pro Ile Trp Ala Lys Ile Pro His Thr
    210                 215                 220

Asp Gly His Phe His Pro Ser Pro Leu Met Gly Gly Phe Gly Leu Lys
225                 230                 235                 240

His Pro Pro Pro Gln Ile Leu Ile Lys Asn
                245                 250

<210> SEQ ID NO 37
<211> LENGTH: 253
<212> TYPE: PRT
<213> ORGANISM: Artificial sequence
<220> FEATURE:
<223> OTHER INFORMATION: Synthetic polypeptide

<400> SEQUENCE: 37

Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
    50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
    130                 135                 140

Ala Asp Tyr Ser Asp Val Met Leu Thr Ser Glu Glu Ile Lys Thr
145                 150                 155                 160

Thr Asn Pro Val Ala Thr Glu Glu Tyr Gly Ile Val Ala Asp Asn Leu
                165                 170                 175

Gln Gln Gln Asn Leu Ala Leu Gly Glu Thr Thr Arg Pro Ala Thr Ala
            180                 185                 190

Pro Gln Ile Gly Thr Val Asn Ser Gln Gly Ala Leu Pro Gly Met Val
        195                 200                 205

Trp Gln Asn Arg Asp Val Tyr Leu Gln Gly Pro Ile Trp Ala Lys Ile
    210                 215                 220
```

```
Pro His Thr Asp Gly Asn Phe His Pro Ser Pro Leu Met Gly Gly Phe
225                 230                 235                 240

Gly Leu Lys His Pro Pro Gln Ile Leu Ile Lys Asn
            245                 250
```

<210> SEQ ID NO 38
<211> LENGTH: 252
<212> TYPE: PRT
<213> ORGANISM: Artificial sequence
<220> FEATURE:
<223> OTHER INFORMATION: Synthetic polypeptide

<400> SEQUENCE: 38

```
Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
                20                  25                  30

Gln Tyr Leu Tyr Tyr Leu Ser Arg Thr Gln Thr Thr Gly Gly Thr Ala
            35                  40                  45

Asn Thr Gln Thr Leu Gly Phe Ser Gln Gly Gly Pro Asn Thr Met Ala
        50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
130                 135                 140

Ala Asp Tyr Ser Asp Val Met Leu Thr Ser Glu Glu Glu Ile Lys Thr
145                 150                 155                 160

Thr Asn Pro Val Ala Thr Glu Glu Tyr Gly Ile Val Ala Asp Asn Leu
                165                 170                 175

Gln Gly Gln Arg Gly Leu Gly Glu Thr Thr Arg Pro Ala Gln Ala Ala
            180                 185                 190

Gln Ile Gly Thr Val Asn Ser Gln Gly Ala Leu Pro Gly Met Val Trp
        195                 200                 205

Gln Asn Arg Asp Val Tyr Leu Gln Gly Pro Ile Trp Ala Lys Ile Pro
210                 215                 220

His Thr Asp Gly Asn Phe His Pro Ser Pro Leu Met Gly Gly Phe Gly
225                 230                 235                 240

Leu Lys His Pro Pro Gln Ile Leu Ile Lys Asn
                245                 250
```

<210> SEQ ID NO 39
<211> LENGTH: 251
<212> TYPE: PRT
<213> ORGANISM: Artificial sequence
<220> FEATURE:
<223> OTHER INFORMATION: Synthetic polypeptide

<400> SEQUENCE: 39

```
Phe Gln Phe Ser Tyr Thr Phe Glu Asp Val Pro Phe His Ser Ser Tyr
1               5                   10                  15

Ala His Ser Gln Ser Leu Asp Arg Leu Met Asn Pro Leu Ile Asp Gln
                20                  25                  30
```

```
Tyr Leu Tyr Tyr Leu Val Arg Thr Gln Thr Thr Gly Thr Gly Gly Thr
             35                  40                  45

Gln Thr Leu Ala Phe Ser Gln Ala Gly Pro Ser Ser Met Ala Asn Gln
     50                  55                  60

Ala Arg Asn Trp Val Pro Gly Pro Cys Tyr Arg Gln Gln Arg Val Ser
 65                  70                  75                  80

Thr Thr Thr Asn Gln Asn Asn Ser Asn Phe Ala Trp Thr Gly Ala
                 85                  90                  95

Ala Lys Phe Lys Leu Asn Gly Arg Asp Ser Leu Met Asn Pro Gly Val
             100                 105                 110

Ala Met Ala Ser His Lys Asp Asp Asp Arg Phe Phe Pro Ser Ser
             115                 120                 125

Gly Val Leu Ile Phe Gly Lys Gln Gly Ala Gly Asn Asp Gly Val Asp
             130                 135                 140

Tyr Ser Gln Val Leu Ile Thr Asp Glu Glu Ile Lys Ala Thr Asn
145                 150                 155                 160

Pro Val Ala Thr Glu Glu Tyr Gly Ala Val Ala Ile Asn Asn Gln Ala
                 165                 170                 175

Ala Asn Leu Ala Leu Gly Glu Thr Thr Arg Pro Ala Thr Gln Ala Gln
             180                 185                 190

Thr Gly Leu Val His Asn Gln Gly Val Ile Pro Gly Met Val Trp Gln
             195                 200                 205

Asn Arg Asp Val Tyr Leu Gln Gly Pro Ile Trp Ala Lys Ile Pro His
             210                 215                 220

Thr Asp Gly Asn Phe His Pro Ser Pro Leu Met Gly Gly Phe Gly Leu
225                 230                 235                 240

Lys His Pro Pro Pro Gln Ile Leu Ile Lys Asn
                 245                 250

<210> SEQ ID NO 40
<211> LENGTH: 253
<212> TYPE: PRT
<213> ORGANISM: Artificial sequence
<220> FEATURE:
<223> OTHER INFORMATION: Synthetic polypeptide

<400> SEQUENCE: 40

Asn Phe Glu Phe Ser Tyr Thr Phe Glu Asp Val Pro Phe His Ser Ser
 1               5                  10                  15

Tyr Ala His Ser Gln Ser Leu Asp Arg Leu Met Asn Pro Leu Ile Asp
                 20                  25                  30

Gln Tyr Leu Tyr Tyr Leu Ser Arg Thr Gln Ser Thr Gly Gly Thr Gln
             35                  40                  45

Gly Thr Gln Gln Leu Leu Phe Ser Gln Ala Gly Pro Ala Asn Met Ser
     50                  55                  60

Ala Gln Ala Lys Asn Trp Leu Pro Gly Pro Cys Tyr Arg Gln Gln Arg
 65                  70                  75                  80

Val Ser Thr Thr Leu Ser Gln Asn Asn Asn Ser Asn Phe Ala Trp Thr
                 85                  90                  95

Gly Ala Thr Lys Tyr His Leu Asn Gly Arg Asp Ser Leu Val Asn Pro
             100                 105                 110

Gly Val Ala Met Ala Thr His Lys Asp Asp Glu Glu Arg Phe Phe Pro
             115                 120                 125

Ser Ser Gly Val Leu Met Phe Gly Lys Gln Gly Ala Gly Arg Asp Asn
             130                 135                 140
```

```
Val Asp Tyr Ser Ser Val Met Leu Thr Ser Glu Glu Ile Lys Thr
145                 150                 155                 160

Thr Asn Pro Val Ala Thr Glu Gln Tyr Gly Val Val Ala Asp Asn Leu
                165                 170                 175

Gln Gln Leu Ala Leu Gly Glu Thr Thr Arg Pro Ala Ala Asn Thr Gly
            180                 185                 190

Pro Ile Val Gly Asn Val Asn Ser Gln Gly Ala Leu Pro Gly Met Val
            195                 200                 205

Trp Gln Asn Arg Asp Val Tyr Leu Gln Gly Pro Ile Trp Ala Lys Ile
210                 215                 220

Pro His Thr Asp Gly Asn Phe His Pro Ser Pro Leu Met Gly Gly Phe
225                 230                 235                 240

Gly Leu Lys His Pro Pro Gln Ile Leu Ile Lys Asn
                245                 250
```

<210> SEQ ID NO 41
<211> LENGTH: 252
<212> TYPE: PRT
<213> ORGANISM: Artificial sequence
<220> FEATURE:
<223> OTHER INFORMATION: Synthetic polypeptide

<400> SEQUENCE: 41

```
Phe Glu Phe Ser Tyr Ser Phe Glu Asp Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Ala Arg Thr Gln Ser Asn Pro Gly Gly Thr Ala
        35                  40                  45

Gly Asn Arg Glu Leu Gln Phe Tyr Gln Gly Gly Pro Ser Thr Met Ala
    50                  55                  60

Glu Gln Ala Lys Asn Trp Leu Pro Gly Pro Cys Phe Arg Gln Gln Arg
65                  70                  75                  80

Val Ser Lys Thr Leu Asp Gln Asn Asn Asn Ser Asn Phe Ala Trp Thr
                85                  90                  95

Gly Ala Thr Lys Tyr His Leu Asn Gly Arg Asn Ser Leu Val Asn Pro
            100                 105                 110

Gly Val Ala Met Ala Thr His Lys Asp Asp Glu Asp Arg Phe Phe Pro
        115                 120                 125

Ser Ser Gly Val Leu Ile Phe Gly Lys Thr Gly Ala Thr Asn Lys Thr
    130                 135                 140

Thr Leu Glu Asn Val Leu Met Thr Asn Glu Glu Glu Ile Arg Pro Thr
145                 150                 155                 160

Asn Pro Val Ala Thr Glu Glu Tyr Gly Ile Val Ser Ser Asn Leu Gln
                165                 170                 175

Ala Ala Asn Leu Ala Leu Gly Glu Thr Thr Arg Pro Ala Thr Ala Ala
            180                 185                 190

Gln Thr Gln Val Val Asn Asn Gln Gly Ala Leu Pro Gly Met Val Trp
        195                 200                 205

Gln Asn Arg Asp Val Tyr Leu Gln Gly Pro Ile Trp Ala Lys Ile Pro
    210                 215                 220

His Thr Asp Gly Asn Phe His Pro Ser Pro Leu Met Gly Gly Phe Gly
225                 230                 235                 240

Leu Lys His Pro Pro Pro Gln Ile Leu Ile Lys Asn
                245                 250
```

<210> SEQ ID NO 42
<211> LENGTH: 249
<212> TYPE: PRT
<213> ORGANISM: Artificial sequence
<220> FEATURE:
<223> OTHER INFORMATION: Synthetic polypeptide

<400> SEQUENCE: 42

```
Phe Gln Phe Ser Tyr Glu Phe Glu Asn Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Ser Lys Thr Ile Asn Gly Ser Gly Gln Asn Gln
        35                  40                  45

Gln Thr Leu Lys Phe Ser Val Ala Gly Pro Ser Asn Met Ala Val Gln
    50                  55                  60

Gly Arg Asn Tyr Ile Pro Gly Pro Ser Tyr Arg Gln Gln Arg Val Ser
65                  70                  75                  80

Thr Thr Val Thr Gln Asn Asn Asn Ser Glu Phe Ala Trp Pro Gly Ala
                85                  90                  95

Ser Ser Trp Ala Leu Asn Gly Arg Asn Ser Leu Met Asn Pro Gly Pro
            100                 105                 110

Ala Met Ala Ser His Lys Glu Gly Glu Asp Arg Phe Phe Pro Leu Ser
        115                 120                 125

Gly Ser Leu Ile Phe Gly Lys Gln Gly Thr Gly Arg Asp Asn Val Asp
    130                 135                 140

Ala Asp Lys Val Met Ile Thr Asn Glu Glu Glu Ile Lys Thr Thr Asn
145                 150                 155                 160

Pro Val Ala Thr Glu Ser Tyr Gly Gln Val Ala Thr Asn His Gln Ser
                165                 170                 175

Ala Gln Leu Ala Leu Gly Glu Thr Thr Arg Pro Ala Gln Ala Gln Thr
            180                 185                 190

Gly Trp Val Gln Asn Gln Gly Ile Leu Pro Gly Met Val Trp Gln Asp
        195                 200                 205

Arg Asp Val Tyr Leu Gln Gly Pro Ile Trp Ala Lys Ile Pro His Thr
    210                 215                 220

Asp Gly Asn Phe His Pro Ser Pro Leu Met Gly Gly Phe Gly Met Lys
225                 230                 235                 240

His Pro Pro Pro Gln Ile Leu Ile Lys
                245
```

<210> SEQ ID NO 43
<211> LENGTH: 248
<212> TYPE: PRT
<213> ORGANISM: Artificial sequence
<220> FEATURE:
<223> OTHER INFORMATION: Synthetic polypeptide

<400> SEQUENCE: 43

```
Gln Phe Ser Tyr Glu Phe Glu Asn Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Ser Lys Thr Ile Asn Gly Ser Gly Gln Asn Gln Gln
        35                  40                  45

Thr Leu Lys Phe Ser Val Ala Gly Pro Ser Asn Met Ala Val Gln Gly
```

Arg Asn Tyr Ile Pro Gly Pro Ser Tyr Arg Gln Gln Arg Val Ser Thr
65                  70                  75                  80

Thr Val Thr Gln Asn Asn Ser Glu Phe Ala Trp Pro Gly Ala Ser
                85                  90                  95

Ser Trp Ala Leu Asn Gly Arg Asn Ser Leu Met Asn Pro Gly Pro Ala
            100                 105                 110

Met Ala Ser His Lys Glu Gly Glu Asp Arg Phe Phe Pro Leu Ser Gly
            115                 120                 125

Ser Leu Ile Phe Gly Lys Gln Gly Thr Gly Arg Asp Asn Val Asp Ala
            130                 135                 140

Asp Lys Val Met Ile Thr Asn Glu Glu Glu Ile Lys Thr Thr Asn Pro
145                 150                 155                 160

Val Ala Thr Glu Ser Tyr Gly Gln Val Ala Thr Asn His Gln Ser Gly
            165                 170                 175

Gln Ala Ala Leu Gly Glu Thr Thr Arg Pro Ala Gln Ala Ala Thr Gly
            180                 185                 190

Trp Val Gln Asn Gln Gly Ile Leu Pro Gly Met Val Trp Gln Asp Arg
            195                 200                 205

Asp Val Tyr Leu Gln Gly Pro Ile Trp Ala Lys Ile Pro His Thr Asp
            210                 215                 220

Gly Asn Phe His Pro Ser Pro Leu Met Gly Gly Phe Gly Met Lys His
225                 230                 235                 240

Pro Pro Pro Gln Ile Leu Ile Lys
                245

<210> SEQ ID NO 44
<211> LENGTH: 250
<212> TYPE: PRT
<213> ORGANISM: Artificial sequence
<220> FEATURE:
<223> OTHER INFORMATION: Synthetic peptide

<400> SEQUENCE: 44

Asn Phe Glu Phe Thr Tyr Asn Phe Glu Glu Val Pro Phe His Ser Ser
1               5                   10                  15

Phe Ala Pro Ser Gln Asn Leu Phe Lys Leu Ala Asn Pro Leu Val Asp
                20                  25                  30

Gln Tyr Leu Tyr Arg Phe Val Ser Thr Asn Asn Thr Gly Gly Val Gln
            35                  40                  45

Phe Asn Lys Asn Leu Ala Gly Arg Tyr Ala Asn Thr Tyr Lys Asn Trp
50                  55                  60

Phe Pro Gly Pro Met Gly Arg Thr Gln Gly Trp Asn Leu Gly Ser Gly
65                  70                  75                  80

Val Asn Arg Ala Ser Val Ser Ala Phe Ala Thr Thr Asn Arg Met Glu
                85                  90                  95

Leu Glu Gly Ala Ser Tyr Gln Val Pro Pro Gln Pro Asn Gly Met Thr
            100                 105                 110

Asn Asn Leu Gln Gly Ser Asn Thr Tyr Ala Leu Glu Asn Thr Met Ile
            115                 120                 125

Phe Asn Ser Gln Pro Ala Asn Pro Gly Thr Thr Ala Thr Tyr Leu Glu
            130                 135                 140

Gly Asn Met Leu Ile Thr Ser Glu Ser Glu Thr Gln Pro Val Asn Arg
145                 150                 155                 160

Val Ala Tyr Asn Val Gly Gly Gln Met Ala Thr Asn Asn Gln Ser Leu

```
              165                 170                 175
Ala Leu Gly Glu Thr Thr Arg Pro Ala Ser Thr Thr Ala Pro Ala Thr
            180                 185                 190

Gly Thr Tyr Asn Leu Gln Glu Ile Val Pro Gly Ser Val Trp Met Glu
        195                 200                 205

Arg Asp Val Tyr Leu Gln Gly Pro Ile Trp Ala Lys Ile Pro Glu Thr
    210                 215                 220

Gly Ala His Phe His Pro Ser Pro Ala Met Gly Gly Phe Gly Leu Lys
225                 230                 235                 240

His Pro Pro Pro Met Met Leu Ile Lys Asn
                245                 250

<210> SEQ ID NO 45
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 45

Leu Ala Leu Gly Glu Thr Thr Arg Pro Ala
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 46

Leu Ala Asn Glu Thr Ile Thr Arg Pro Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 47

Leu Ala Lys Ala Gly Gln Ala Asn Asn Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 48

Leu Ala Lys Asp Pro Lys Thr Thr Asn Ala
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 49
```

Ala Ala Leu Gly Glu Thr Thr Arg Pro Ala
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Ala Ala Asn Glu Thr Ile Thr Arg Pro Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 51

Ala Ala Lys Ala Gly Gln Ala Asn Asn Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 52

Ala Ala Lys Asp Pro Lys Thr Thr Asn Ala
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 53

Gly Leu Gly Glu Thr Thr Arg Pro Ala
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 54

Gly Asn Glu Thr Ile Thr Arg Pro Ala
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 55

Gly Lys Ala Gly Gln Ala Asn Asn Ala 1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Gly Lys Asp Pro Lys Thr Thr Asn Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 57

Lys Asp Thr Asp Thr Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 58

Arg Ala Gly Gly Ser Val Gly
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 59

Ala Val Asp Thr Thr Lys Phe
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 60

Ser Thr Gly Lys Val Pro Asn
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 61

Leu Ala Lys Asp Thr Asp Thr Thr Arg Ala
1               5                   10

```
<210> SEQ ID NO 62
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 62

Leu Ala Arg Ala Gly Gly Ser Val Gly Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 63

Leu Ala Ala Val Asp Thr Thr Lys Phe Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 64

Leu Ala Ser Thr Gly Lys Val Pro Asn Ala
1               5                   10
```

What is claimed is:

1. A recombinant adeno-associated virus (rAAV) virion comprising:
   a) a variant AAV capsid protein, wherein the variant AAV capsid protein comprises a peptide insertion relative to a corresponding parental AAV capsid protein, wherein the peptide insertion comprises the amino acid sequence LGETTRP (SEQ ID NO:13), wherein the insertion site is located between two adjacent amino acids at a position between amino acids corresponding to amino acids 570 and 611 of VP1 of AAV2 or the corresponding position in the capsid protein of another AAV serotype, and wherein the variant capsid protein confers increased infectivity of a retinal cell compared to the infectivity of the retinal cell by an AAV virion comprising the corresponding parental AAV capsid protein, wherein the retinal cell is a photoreceptor, a retinal ganglion cell, a Müller cell, a bipolar cell, an amacrine cell, a horizontal cell, or a retinal pigmented epithelium cell; and
   b) a heterologous nucleic acid comprising a nucleotide sequence encoding a gene product.

2. The rAAV virion of claim 1, wherein the insertion site is located between amino acids corresponding to amino acids 587 and 588 of VP1 of AAV2 or the corresponding position in the capsid protein of another AAV serotype.

3. The rAAV virion of claim 1, wherein the rAAV virion exhibits at least 10-fold increased infectivity of a retinal cell compared to the infectivity of the retinal cell by an AAV virion comprising the corresponding parental AAV capsid protein.

4. The rAAV virion of claim 1, wherein the rAAV virion exhibits at least 50-fold increased infectivity of a retinal cell compared to the infectivity of the retinal cell by an AAV virion comprising the corresponding parental AAV capsid protein.

5. The rAAV virion of claim 1, wherein gene product is an interfering RNA or an aptamer.

6. The rAAV virion of claim 1, wherein the gene product is a polypeptide.

7. The rAAV virion of claim 6, wherein the polypeptide is a neuroprotective polypeptide, an anti-angiogenic polypeptide, or a polypeptide that enhances function of a retinal cell.

8. A pharmaceutical composition comprising:
   a) a recombinant adeno-associated virus virion of claim 1; and
   b) a pharmaceutically acceptable excipient.

9. A method of delivering a gene product to a retinal cell in an individual, the method comprising administering to the individual a recombinant adeno-associated virus (rAAV) virion according to claim 1.

10. The method of claim 9, wherein the gene product is a polypeptide.

11. The method of claim 9, wherein the gene product is a short interfering RNA or an aptamer.

12. The method of claim 10, wherein the polypeptide is a neuroprotective factor, an anti-angiogenic polypeptide, an anti-apoptotic factor, or a polypeptide that enhances function of a retinal cell.

13. The method of claim 10, wherein the polypeptide is glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, or Sonic hedgehog.

14. A method of treating an ocular disease, the method comprising administering to an individual in need thereof an effective amount of a recombinant adeno-associated virus (rAAV) virion according to claim 1.

15. The method of claim 14, wherein said administering is by intraocular injection.

16. The method of claim 14, wherein said administering is by intravitreal injection.

17. The method of claim 14, wherein the ocular disease is glaucoma, retinitis pigmentosa, macular degeneration, retinoschisis, Leber's Congenital Amaurosis, diabetic retinopathy, achromotopsia, or color blindness.

18. An isolated nucleic acid comprising a nucleotide sequence that encodes a variant adeno-associated virus (AAV) capsid protein, wherein the variant AAV capsid protein comprises a peptide insertion relative to a corresponding parental AAV capsid protein, wherein the peptide insertion comprises the amino acid sequence LGETTRP (SEQ ID NO:13), wherein the insertion site is located between two adjacent amino acids at a position between amino acids corresponding to amino acids 570 and 611 of VP1 of AAV2 or the corresponding position in the capsid protein of another AAV serotype, and wherein the variant capsid protein, when present in an AAV virion, provides for increased infectivity of the AAV virion of a retinal cell, wherein the retinal cell is a photoreceptor, a retinal ganglion cell, a Müller cell, a bipolar cell, an amacrine cell, a horizontal cell, or a retinal pigmented epithelium cell.

19. The isolated nucleic acid of claim 18, wherein the insertion site is located between amino acids corresponding to amino acids 587 and 588 of VP1 of AAV2 or the corresponding position in the capsid protein of another AAV serotype.

20. An isolated, genetically modified host cell comprising the nucleic acid of claim 18.

21. A variant adeno-associated virus (AAV) capsid protein, wherein the variant AAV capsid protein comprises a peptide insertion relative to a corresponding parental AAV capsid protein, wherein the peptide insertion comprises the amino acid sequence LGETTRP (SEQ ID NO:13), wherein the insertion site is located between two adjacent amino acids at a position between amino acids corresponding to amino acids 570 and 611 of VP1 of AAV2 or the corresponding position in the capsid protein of another AAV serotype, and wherein the variant AAV capsid protein, when present in an AAV virion, confers increased infectivity of a retinal cell compared to the infectivity of the retinal cell by an AAV virion comprising the corresponding parental AAV capsid protein, wherein the retinal cell is a photoreceptor, a retinal ganglion cell, a Muller cell, a bipolar cell, an amacrine cell, a horizontal cell, or a retinal pigmented epithelium cell.

22. The variant AAV capsid protein of claim 21, wherein the insertion site is located between amino acids corresponding to amino acids 587 and 588 of VP1 of AAV2 or the corresponding position in the capsid protein of another AAV serotype.

23. The rAAV virion of claim 1, wherein the parental capsid protein is an AAV2 capsid protein and the insertion site is between amino acids 570 and 611 of the parental AAV2 capsid protein.

24. The isolated nucleic acid of claim 18, wherein the parental capsid protein is an AAV2 capsid protein and the insertion site is between amino acids 570 and 611 of the parental AAV2 capsid protein.

25. The variant AAV capsid protein of claim 21, wherein the parental capsid protein is an AAV2 capsid protein and the insertion site is between amino acids 570 and 611 of the parental AAV2 capsid protein.

* * * * *

(12) EX PARTE REEXAMINATION CERTIFICATE (212th)
Ex Parte Reexamination Ordered under 35 U.S.C. 257

United States Patent
Schaffer et al.

(10) Number: US 9,193,956 C1
(45) Certificate Issued: Apr. 4, 2022

(54) ADENO-ASSOCIATED VIRUS VIRIONS WITH VARIANT CAPSID AND METHODS OF USE THEREOF

(75) Inventors: David V. Schaffer, Danville, CA (US); Ryan R. Klimczak, San Francisco, CA (US); James T. Koerber, San Francisco, CA (US); John G. Flannery, Berkeley, CA (US); Deniz Dalkara Mourot, Berkeley, CA (US); Meike Visel, El Cerrito, CA (US); Leah C. T. Byrne, Berkeley, CA (US)

(73) Assignee: THE REGENTS OF THE UNIVERSITY OF CALIFORNIA, Oakland, CA (US)

Supplemental Examination Request:
No. 96/000,373, Sep. 28, 2021

Reexamination Certificate for:
Patent No.: 9,193,956
Issued: Nov. 24, 2015
Appl. No.: 14/113,205
PCT Filed: Apr. 20, 2012
PCT No.: PCT/US2012/034413
§ 371 (c)(1),
(2), (4) Date: Jan. 22, 2014
PCT Pub. No.: WO2012/145601
PCT Pub. Date: Oct. 26, 2012

Related U.S. Application Data

(60) Provisional application No. 61/478,355, filed on Apr. 22, 2011.

(51) Int. Cl.
*C12Q 1/70* (2006.01)
*A61K 9/00* (2006.01)
*A61K 38/17* (2006.01)
*A61K 48/00* (2006.01)
*C07K 14/005* (2006.01)
*C12N 15/113* (2010.01)
*C12N 15/115* (2010.01)
*C12N 15/86* (2006.01)
*G01N 33/50* (2006.01)
*C12N 7/00* (2006.01)

(52) U.S. Cl.
CPC ............ *C12Q 1/701* (2013.01); *A61K 9/0019* (2013.01); *A61K 9/0048* (2013.01); *A61K 38/1709* (2013.01); *A61K 48/0008* (2013.01); *A61K 48/0025* (2013.01); *A61K 48/0075* (2013.01); *C07K 14/005* (2013.01); *C12N 7/00* (2013.01); *C12N 15/113* (2013.01); *C12N 15/115* (2013.01); *C12N 15/86* (2013.01); *C12Q 1/70* (2013.01); *G01N 33/5008* (2013.01); *G01N 33/5058* (2013.01); *C07K 2319/33* (2013.01); *C12N 2310/14* (2013.01); *C12N 2310/16* (2013.01); *C12N 2320/32* (2013.01); *C12N 2750/14021* (2013.01); *C12N 2750/14121* (2013.01); *C12N 2750/14122* (2013.01); *C12N 2750/14142* (2013.01); *C12N 2750/14143* (2013.01); *C12N 2750/14145* (2013.01); *C12N 2750/14152* (2013.01); *C12N 2810/40* (2013.01); *C12Q 2600/158* (2013.01); *C12Q 2600/16* (2013.01)

(58) Field of Classification Search
CPC ..... C07K 14/005; C12Q 1/70; G01N 33/5058
See application file for complete search history.

(56) References Cited

To view the complete listing of prior art documents cited during the supplemental examination proceeding and the resulting reexamination proceeding for Control Number 96/000,373, please refer to the USPTO's public Patent Application Information Retrieval (PAIR) system under the Display References tab.

*Primary Examiner* — Sharon Turner

(57) ABSTRACT

The present disclosure provides adeno-associated virus (AAV) virions with altered capsid protein, where the AAV virions exhibit greater infectivity of retinal cells, when administered via intravitreal injection, compared to wild-type AAV. The present disclosure further provides methods of delivering a gene product to a retinal cell in an individual, and methods of treating ocular disease.

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3-5, 7, 9, 11-13, 17-18, 21 and 23-25 are determined to be patentable as amended.

Claims 2, 6, 8, 10, 14-16, 19-20 and 22, dependent on an amended claim, are determined to be patentable.

1. A recombinant adeno-associated virus (rAAV) virion comprising:
   a) a variant AAV capsid protein, wherein the variant AAV capsid protein comprises a peptide insertion relative to a corresponding parental AAV capsid protein, wherein the peptide insertion comprises the amino acid sequence LGETTRP (SEQ ID NO:13), wherein the insertion site is located between two adjacent amino acids at a position between amino acids corresponding to amino acids 570 and [611] *610* of VP1 of AAV2 or the corresponding position in the capsid protein of another AAV serotype, and wherein the variant capsid protein confers increased infectivity of a [retinal] *photoreceptor* cell compared to the infectivity of the [retinal] *photoreceptor* cell by an AAV virion comprising the corresponding parental AAV capsid protein[, wherein the retinal cell is a photoreceptor, a retinal ganglion cell, a Müller cell, a bipolar cell, an amacrine cell, a horizontal cell, or a retinal pigmented epithelium cell]; and
   b) a heterologous nucleic acid comprising a nucleotide sequence encoding a gene product.

3. The rAAV virion of claim 1, wherein the rAAV virion exhibits at least 10-fold increased infectivity of a [retinal] *photoreceptor* cell compared to the infectivity of the [retinal] *photoreceptor* cell by an AAV virion comprising the corresponding parental AAV capsid protein.

4. The rAAV virion of claim 1, wherein the rAAV virion exhibits at least 50-fold increased infectivity of a [retinal] *photoreceptor* cell compared to the infectivity of the [retinal] *photoreceptor* cell by an AAV virion comprising the corresponding parental AAV capsid protein.

5. The rAAV virion of claim 1, wherein gene product is an interfering RNA [or an aptamer].

7. The rAAV virion of claim 6, wherein the polypeptide is a neuroprotective polypeptide, an anti-angiogenic polypeptide, or [a] *an anti-apoptotic* polypeptide [that enhances function of a retinal cell].

9. A method of delivering a gene product to a [retinal] *photoreceptor* cell in an individual, the method comprising administering to the individual a recombinant adeno-associated virus (rAAV) virion according to claim 1.

11. The method of claim 9, wherein the gene product is a short interfering RNA [or an aptamer].

12. The method of claim 10, wherein the polypeptide is a neuroprotective factor, an anti-angiogenic polypeptide, *or an* anti-apoptotic factor[, or a polypeptide that enhances function of a retinal cell].

13. The method of claim 10, wherein the polypeptide is glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, [retinoschisin, RPE65, retinitis pigmentosa GTPase-interacting protein-1, peripherin, peripherin-2, a rhodopsin,] or Sonic hedgehog.

17. The method of claim 14, wherein the ocular disease is glaucoma, retinitis pigmentosa, macular degeneration, retinoschisis, [Leber's Congenital Amaurosis,] *or* diabetic retinopathy[, achromotopsia, or color blindness].

18. An isolated nucleic acid comprising a nucleotide sequence that encodes a variant adeno-associated virus (AAV) capsid protein, wherein the variant AAV capsid protein comprises a peptide insertion relative to a corresponding parental AAV capsid protein, wherein the peptide insertion comprises the amino acid sequence LGETTRP (SEQ ID NO:13), wherein the insertion site is located between two adjacent amino acids at a position between amino acids corresponding to amino acids 570 and [611] *610* of VP1 of AAV2 or the corresponding position in the capsid protein of another AAV serotype, and wherein the variant capsid protein, when present in an AAV virion, provides for increased infectivity of the AAV virion of a [retinal] *photoreceptor* cell[, wherein the retinal cell is a photoreceptor, a retinal ganglion cell, a Müller cell, a bipolar cell, an amacrine cell, a horizontal cell, or a retinal pigmented epithelium cell].

21. A variant adeno-associated virus (AAV) capsid protein, wherein the variant AAV capsid protein comprises a peptide insertion relative to a corresponding parental AAV capsid protein, wherein the peptide insertion comprises the amino acid sequence LGETTRP (SEQ ID NO:13), wherein the insertion site is located between two adjacent amino acids at a position between amino acids corresponding to amino acids 570 and [611] *610* of VP1 of AAV2 or the corresponding position in the capsid protein of another AAV serotype, and wherein the variant capsid protein, when present in an AAV virion, confers increased infectivity of a [retinal] *photoreceptor* cell compared to the infectivity of the [retinal] *photoreceptor* cell by an AAV virion comprising the corresponding parental AAV capsid protein[, wherein the retinal cell is a photoreceptor, a retinal ganglion cell, a Muller cell, a bipolar cell, an amacrine cell, a horizontal cell, or a retinal pigmented epithelium cell].

23. The rAAV virion of claim 1, wherein the parental capsid protein is an AAV2 capsid protein and the insertion site is between amino acids 570 and [611] *610* of the parental AAV2 capsid protein.

24. The isolated nucleic acid of claim 18, wherein the parental capsid protein is an AAV2 capsid protein and the insertion site is between amino acids 570 and [611] *610* of the parental AAV2 capsid protein.

25. The variant AAV capsid protein of claim 21, wherein the parental capsid protein is an AAV2 capsid protein and the insertion site is between amino acids 570 and [611] *610* of the parental AAV2 capsid protein.

\* \* \* \* \*